United States Patent
Takahashi et al.

(10) Patent No.: US 9,783,844 B2
(45) Date of Patent: Oct. 10, 2017

(54) METHOD FOR AMPLIFYING NUCLEIC ACID AND METHOD FOR DETECTING AMPLIFIED NUCLEIC ACID

(71) Applicant: Kaneka Corporation, Osaka (JP)

(72) Inventors: Koji Takahashi, Takasago (JP); Shigehiko Miyamoto, Takasago (JP); Takaaki Jikihara, Takasago (JP); Sotaro Sano, Takasago (JP); Jun Tomono, Takasago (JP)

(73) Assignee: Kaneka Corporation, Oasaka (JP)

( * ) Notice: Subject to any disclaimer, the term of this patent is extended or adjusted under 35 U.S.C. 154(b) by 0 days.

(21) Appl. No.: 14/396,466

(22) PCT Filed: Apr. 26, 2013

(86) PCT No.: PCT/JP2013/062488
§ 371 (c)(1),
(2) Date: Oct. 23, 2014

(87) PCT Pub. No.: WO2013/162026
PCT Pub. Date: Oct. 31, 2013

(65) Prior Publication Data
US 2015/0203905 A1 Jul. 23, 2015

(30) Foreign Application Priority Data
Apr. 27, 2012 (JP) .................... 2012-103691

(51) Int. Cl.
*C12Q 1/68* (2006.01)
(52) U.S. Cl.
CPC ......... *C12Q 1/6853* (2013.01); *C12Q 1/6834* (2013.01)
(58) Field of Classification Search
None
See application file for complete search history.

(56) References Cited

U.S. PATENT DOCUMENTS

| | | |
|---|---|---|
| 5,310,650 A | 5/1994 | McMahon et al. |
| 5,475,098 A | 12/1995 | Hall et al. |
| 5,525,494 A * | 6/1996 | Newton ............... 435/91.2 |
| 5,629,158 A | 5/1997 | Uhlen |
| 5,874,216 A | 2/1999 | Mapes |
| 7,932,060 B2 | 4/2011 | Nadeau |
| 2003/0108913 A1 | 6/2003 | Schouten |
| 2005/0142559 A1* | 6/2005 | Makrigiorgos ............ 435/6 |
| 2006/0134802 A1 | 6/2006 | Donati et al. |
| 2008/0274464 A1 | 11/2008 | Goto et al. |
| 2009/0136956 A1 | 5/2009 | Merante et al. |
| 2010/0291666 A1* | 11/2010 | Collier et al. ............. 435/287.2 |
| 2010/0330564 A1 | 12/2010 | Tomono |
| 2010/0330574 A1* | 12/2010 | Whitman et al. ................. 435/6 |
| 2012/0053063 A1 | 3/2012 | Rigatti et al. |
| 2013/0052652 A1* | 2/2013 | Schneider et al. ........... 435/6.12 |
| 2014/0065725 A1* | 3/2014 | Takahashi et al. ............ 436/501 |

FOREIGN PATENT DOCUMENTS

| | | |
|---|---|---|
| CN | 1459506 A | 12/2003 |
| CN | 1697883 A | 11/2005 |
| CN | 1891832 A | 1/2007 |
| CN | 1982325 A | 8/2007 |
| CN | 101137759 A | 3/2008 |
| CN | 101845511 A | 9/2010 |
| EP | 0416817 A2 | 3/1991 |
| EP | 1634962 A1 | 3/2006 |
| EP | 2410063 A1 | 1/2012 |
| EP | 2762562 A1 | 8/2014 |
| EP | 2789689 A1 | 10/2014 |
| JP | H02-283299 A | 11/1990 |
| JP | H02283299 A | 11/1990 |
| JP | 03-272686 | 4/1991 |
| JP | H03-272686 A | 12/1991 |
| JP | 05-252998 A | 5/1993 |
| JP | 05-252998 A | 10/1993 |
| JP | 2001157598 A | 6/2001 |
| JP | 2002-530677 A | 9/2002 |
| JP | 2002-534434 A | 10/2002 |
| JP | 2003-504018 A | 2/2003 |
| JP | 2004-502464 A | 1/2004 |
| JP | 2006-201062 A | 8/2006 |
| JP | 2007-111048 A | 5/2007 |
| JP | 2007-526443 A | 9/2007 |
| JP | 2008-525037 A | 7/2008 |
| JP | 2008525037 A * | 7/2008 |

(Continued)

OTHER PUBLICATIONS

Newton et al. (The production of PCR products with 5' single-stranded tails using primers that incorporate novel phosphoramidite intermediates, Nucleic Acids Res. Mar. 11, 1993; 21(5): 1155-1162).*
Liang et al. (Nick Sealing by T4 DNA Ligase on a Modified DNA Template: Tethering a Functional Molecule on d-Threoninol, Chemistry. Sep. 5, 2011;17(37):10388-96. Epub Aug. 4, 2011).*
Hyashi et al. (Application of L-DNA as a molecular tag, Nucleic Acids Symp Ser (Sep. 2005) 49 (1): 261-262).*
Hauser et al. (Utilising the left-helical conformation of L-DNA for analysing different marker types on a single universal microarray platform, Nucleic Acids Res. Oct. 2006; 34(18): 5101-5111. Published online Sep. 20, 2006).*
Carter et al. (Lateral flow microarrays: a novel platform for rapid nucleic acid detection based on miniaturized lateral flow chromatography, Nucleic Acids Res. 2007;35(10):e74. Epub May 3, 2007).*
Liu et al. (A universal biosensor for multiplex DNA detection based on hairpin probe assisted cascade signal amplification, Chem Commun (Camb) Jun. 2013;49(45):5165-7, published online Apr. 10, 2013).*

(Continued)

*Primary Examiner* — Aaron Priest
(74) *Attorney, Agent, or Firm* — Polsinelli PC

(57) ABSTRACT

An object of the present invention is to provide methods for amplifying and detecting a nucleic acid that allow efficient hybridization, and devices and kits for use in the methods. The present invention includes amplifying a target nucleic acid into a double-stranded nucleic acid having a single-stranded region at each end, and detecting this nucleic acid. The present invention also provides detection devices and kits that make use of these methods.

21 Claims, 8 Drawing Sheets

(56) References Cited

FOREIGN PATENT DOCUMENTS

| | | |
|---|---|---|
| JP | 2009-521924 A | 6/2009 |
| JP | 2009-296948 A | 12/2009 |
| JP | 2010-513854 A | 4/2010 |
| WO | WO-96/36733 A1 | 11/1996 |
| WO | WO-98/14610 A2 | 4/1998 |
| WO | WO-00/31539 A1 | 6/2000 |
| WO | WO 0040592 A1 * | 7/2000 |
| WO | WO-01/02559 A1 | 1/2001 |
| WO | WO-0121637 A1 | 3/2001 |
| WO | WO-02/04668 A2 | 1/2002 |
| WO | WO-0224944 A2 | 3/2002 |
| WO | WO-2004/109285 A1 | 12/2004 |
| WO | WO-2006/071770 A2 | 7/2006 |
| WO | WO-2006/095550 A1 | 9/2006 |
| WO | WO-2008/075213 A2 | 6/2008 |
| WO | WO-2009/034842 A1 | 3/2009 |
| WO | WO-2010/106997 A1 | 9/2010 |
| WO | WO-2011-137911 A2 | 11/2011 |
| WO | WO-2012/070618 A1 | 5/2012 |
| WO | WO-2013/038534 A1 | 3/2013 |
| WO | WO-2013/039228 A1 | 3/2013 |
| WO | WO-2013-040491 A2 | 3/2013 |

OTHER PUBLICATIONS

Brownie et al. (The elimination of primer-dimer accumulation in PCR, Nucleic Acids Res. Aug. 15, 1997; 25(16): 3235-3241).*
Liang et al., "Nick Sealing by T4 DNA Ligase on a Modified DNA Template: Tethering a Functional Molecule on D-Threoninol", Chem. Eur. J., 2011, vol. 17, pp. 10388-10396.
International Preliminary Report on Patentability issued Oct. 28, 2014 in PCT/JP2013/062488.
Bindon et al., Nucleic Acids Research. 26, 3305-3308, 1998.
International Preliminary Report on Patentability issued Jun. 12, 2013 in Appl. No. PCT/JP2011/077050.
Jung et al., "Fabrication of single-walled carbon nanotubes dotted with Au nanocrystals: Potential DNA delivery nanocarriers", Carbon, vol. 48, No. 4, 2010, pp. 1070-1078, XP026859548.
Liang et al., "Construction of a photo-switchable gene for turning on and off gene expression with light irradiation", Nucleic Acids Symposium Series, vol. 52, 2008, pp. 19-20, XP002721990.
Reinhartz, et al., "A novel rapid hybridization technique: paper chromatography hybridization assay (PACHA)", Gene, vol. 136, No. 1-2, 1993, pp. 221-226, XP023797207.
Highlighting Japan Online Magazine, "Easy Detection of Multiple Genes", [Series] Science & Technology, Mar. 2013, XP002721991.
Corstjens et al., "Lateral-flow and up-converting phosphor reporters to detect single-straded nucleic acids in a sandwich-hybridization assay", Analytical biochemistry, 312 (2003) 191-200.
Vircell, Speed-oligo Informative Dossier (the second edition), Jun. 2010.
Jusus de la Calle I. et al., 19th European Congress of Clinical Microbiology and Infectious Diseases, May 2009.
Yoshinao Wada, "Separate Analysis of Complementary Strands of Restriction Enzyme-digested DNA. An Application of Restriction Fragment Mass Mapping by Matrix-assisted Laser Desorption/Ionization Mass Spectrometry", Journal of Mass Spectrometry, vol. 33, pp. 187-192 (1998).
Kaluz et al., "Ligation-independent cloning of PCR products with primers containing nonbase residues", Nucleic Acids Research, 1994, vol. 22 No. 22, p. 4845.
Preceedings, The 77th Annual Meeting of The Chemical Society of Japan, Union of Chemistry-Related Societies Research Workshop, Sep. 10, 1999, p. 229.
Asanuma et al., "Photo-Responsive Oligonucleotides Carrying Azobenzene in the Side-Chains", Tetrahedron Letters, vol. 39, No. 49, pp. 9015-9018.
Journal of Synthetic Organic Chemistry, Japan, 2005, vol. 63, pp. 63-75.
Yamazawa et al., "Photoregulation of the DNA Polymerase Reaction by Oligonucleotides Bearing an Azobenzene", Angew. Chem. Int. Ed., 2000, 39, No. 13, 2356-2357.
Yamazawa et al., Supporting Information n-Supplemental Figure 1-3, Agnew. Chem. 2000 (Supporting Information for Cite No. CA).
Takeshi Ujilye, "Useful Method Nucleic Acid-Chromatography for genetic testing", Clinical Chemistry, vol. 36, 2007, pp. 19-24 (Partial Translation).

* cited by examiner

SEQUENCE LISTING

<160> NUMBER OF SEQ ID NOS: 121

<210> SEQ ID NO 1
<211> LENGTH: 20
<212> TYPE: DNA
<213> ORGANISM: Artificial
<220> FEATURE:
<223> OTHER INFORMATION: Primer F

<400> SEQUENCE: 1
ggaaacagct atgaccatga                    20

```
<210> SEQ ID NO 2
<211> LENGTH: 19
<212> TYPE: DNA
<213> ORGANISM: Artificial
<220> FEATURE:
<223> OTHER INFORMATION: Primer R

<400> SEQUENCE: 2
ctatgcggca tcagagcag                                                19

<210> SEQ ID NO 3
<211> LENGTH: 27
<212> TYPE: DNA
<213> ORGANISM: Artificial
<220> FEATURE:
<223> OTHER INFORMATION: Tag sequence Ta

<400> SEQUENCE: 3
tggcaacatt tttcactggg tttatag                                       27

<210> SEQ ID NO 4
<211> LENGTH: 47
<212> TYPE: DNA
<213> ORGANISM: Artificial
<220> FEATURE:
<223> OTHER INFORMATION: Primer Ta-Sx-F
<220> FEATURE:
<221> NAME/KEY: misc_feature
<222> LOCATION: (27)..(28)
<223> OTHER INFORMATION: g at position 27 is jointed to g at position 28
      by the Sx (Spacer) represented by Formula (1)-(31) of the
      specification.

<400> SEQUENCE: 4
tggcaacatt tttcactggg tttataggga aacagctatg accatga                 47

<210> SEQ ID NO 5
<211> LENGTH: 47
<212> TYPE: DNA
<213> ORGANISM: Artificial
<220> FEATURE:
<223> OTHER INFORMATION: Primer Ta-F

<400> SEQUENCE: 5
tggcaacatt tttcactggg tttataggga aacagctatg accatga                 47

<210> SEQ ID NO 6
<211> LENGTH: 47
<212> TYPE: DNA
<213> ORGANISM: Artificial
<220> FEATURE:
<223> OTHER INFORMATION: Primer mTa-F
<220> FEATURE:
<221> NAME/KEY: misc_feature
<222> LOCATION: (1)..(1)
<223> OTHER INFORMATION: modified with biotin.

<400> SEQUENCE: 6
tggcaacatt tttcactggg tttataggga aacagctatg accatga                 47

<210> SEQ ID NO 7
<211> LENGTH: 47
<212> TYPE: DNA
<213> ORGANISM: Artificial
<220> FEATURE:
<223> OTHER INFORMATION: Primer Ta-Fm
<220> FEATURE:
```

<221> NAME/KEY: misc_feature
<222> LOCATION: (47)..(47)
<223> OTHER INFORMATION: modified with FITC.

<400> SEQUENCE: 7
tggcaacatt tttcactggg tttataggga aacagctatg accatga           47

<210> SEQ ID NO 8
<211> LENGTH: 27
<212> TYPE: DNA
<213> ORGANISM: Artificial
<220> FEATURE:
<223> OTHER INFORMATION: Tag sequence Tm

<400> SEQUENCE: 8
ggttagcttc caaccacgtg tagatca                                 27

<210> SEQ ID NO 9
<211> LENGTH: 46
<212> TYPE: DNA
<213> ORGANISM: Artificial
<220> FEATURE:
<223> OTHER INFORMATION: Primer Tm-S1-R
<220> FEATURE:
<221> NAME/KEY: misc_feature
<222> LOCATION: (27)..(28)
<223> OTHER INFORMATION: a at position 27 is jointed to c at position 28
      by the S1 (Spacer) represented by Formula (1) of the
      specification.

<400> SEQUENCE: 9
ggttagcttc caaccacgtg tagatcacta tgcggcatca gagcag            46

<210> SEQ ID NO 10
<211> LENGTH: 27
<212> TYPE: DNA
<213> ORGANISM: Artificial
<220> FEATURE:
<223> OTHER INFORMATION: Probe
<220> FEATURE:
<221> NAME/KEY: modified_base
<222> LOCATION: (27)..(27)
<223> OTHER INFORMATION: modified with thiol group.

<400> SEQUENCE: 10
ctataaaccc agtgaaaaat gttgcca                                 27

<210> SEQ ID NO 11
<211> LENGTH: 27
<212> TYPE: DNA
<213> ORGANISM: Artificial
<220> FEATURE:
<223> OTHER INFORMATION: Probe
<220> FEATURE:
<221> NAME/KEY: modified_base
<222> LOCATION: (27)..(27)
<223> OTHER INFORMATION: modified with biotin.

<400> SEQUENCE: 11
gatcatacac gtggttggaa gctaacc                                 27

<210> SEQ ID NO 12
<211> LENGTH: 20
<212> TYPE: DNA
<213> ORGANISM: Artificial
<220> FEATURE:
<223> OTHER INFORMATION: Tag sequence T1
<220> FEATURE:
<221> NAME/KEY: misc_feature

```
<222> LOCATION: (1)..(20)
<223> OTHER INFORMATION: L-form DNA

<400> SEQUENCE: 12
gacaacggag acagagccaa                                               20

<210> SEQ ID NO 13
<211> LENGTH: 20
<212> TYPE: DNA
<213> ORGANISM: Artificial
<220> FEATURE:
<223> OTHER INFORMATION: Tag sequence T2
<220> FEATURE:
<221> NAME/KEY: misc_feature
<222> LOCATION: (1)..(20)
<223> OTHER INFORMATION: L-form DNA

<400> SEQUENCE: 13
atgctaccgt atgcccagtg                                               20

<210> SEQ ID NO 14
<211> LENGTH: 40
<212> TYPE: DNA
<213> ORGANISM: Artificial
<220> FEATURE:
<223> OTHER INFORMATION: Primer T1-F
<220> FEATURE:
<221> NAME/KEY: misc_feature
<222> LOCATION: (1)..(20)
<223> OTHER INFORMATION: L-form DNA

<400> SEQUENCE: 14
gacaacggag acagagccaa ggaaacagct atgaccatga                         40

<210> SEQ ID NO 15
<211> LENGTH: 39
<212> TYPE: DNA
<213> ORGANISM: Artificial
<220> FEATURE:
<223> OTHER INFORMATION: Primer T2-R
<220> FEATURE:
<221> NAME/KEY: misc_feature
<222> LOCATION: (1)..(20)
<223> OTHER INFORMATION: L-form DNA

<400> SEQUENCE: 15
atgctaccgt atgcccagtg ctatgcggca tcagagcag                          39

<210> SEQ ID NO 16
<211> LENGTH: 20
<212> TYPE: DNA
<213> ORGANISM: Artificial
<220> FEATURE:
<223> OTHER INFORMATION: Probe 3
<220> FEATURE:
<221> NAME/KEY: misc_feature
<222> LOCATION: (1)..(20)
<223> OTHER INFORMATION: L-form DNA
<220> FEATURE:
<221> NAME/KEY: modified_base
<222> LOCATION: (20)..(20)
<223> OTHER INFORMATION: modified with amino group.

<400> SEQUENCE: 16
ttggctctgt ctccgttgtc                                               20

<210> SEQ ID NO 17
<211> LENGTH: 20
<212> TYPE: DNA
```

```
<213> ORGANISM: Artificial
<220> FEATURE:
<223> OTHER INFORMATION: Probe 4
<220> FEATURE:
<221> NAME/KEY: misc_feature
<222> LOCATION: (1)..(20)
<223> OTHER INFORMATION: L-form DNA
<220> FEATURE:
<221> NAME/KEY: modified_base
<222> LOCATION: (20)..(20)
<223> OTHER INFORMATION: modified with amino group.

<400> SEQUENCE: 17
cactgggcat acggtagcat                                              20

<210> SEQ ID NO 18
<211> LENGTH: 42
<212> TYPE: DNA
<213> ORGANISM: Artificial
<220> FEATURE:
<223> OTHER INFORMATION: PCR inhibitory sequence H

<400> SEQUENCE: 18
aggcgaggtc gcgagcgcac atgtgcgctc gcgacctcgc ct                     42

<210> SEQ ID NO 19
<211> LENGTH: 25
<212> TYPE: DNA
<213> ORGANISM: Artificial
<220> FEATURE:
<223> OTHER INFORMATION: Tag sequence T3

<400> SEQUENCE: 19
tatgatatgc ttctccacgc ataat                                        25

<210> SEQ ID NO 20
<211> LENGTH: 21
<212> TYPE: DNA
<213> ORGANISM: Artificial
<220> FEATURE:
<223> OTHER INFORMATION: Tag sequence T4

<400> SEQUENCE: 20
tgctctgtac acttgctcaa t                                            21

<210> SEQ ID NO 21
<211> LENGTH: 87
<212> TYPE: DNA
<213> ORGANISM: Artificial
<220> FEATURE:
<223> OTHER INFORMATION: Primer T3-H-F

<400> SEQUENCE: 21
tatgatatgc ttctccacgc ataataggcg aggtcgcgag cgcacatgtg cgctcgcgac  60
ctcgcctgga aacagctatg accatga                                      87

<210> SEQ ID NO 22
<211> LENGTH: 82
<212> TYPE: DNA
<213> ORGANISM: Artificial
<220> FEATURE:
<223> OTHER INFORMATION: Primer T4-H-R

<400> SEQUENCE: 22
tgctctgtac acttgctcaa taggcgaggt cgcgagcgca catgtgcgct cgcgacctcg  60
cctctatgcg gcatcagagc ag                                           82
```

<210> SEQ ID NO 23
<211> LENGTH: 25
<212> TYPE: DNA
<213> ORGANISM: Artificial
<220> FEATURE:
<223> OTHER INFORMATION: Probe 5
<220> FEATURE:
<221> NAME/KEY: modified_base
<222> LOCATION: (25)..(25)
<223> OTHER INFORMATION: modified with amino group.

<400> SEQUENCE: 23
attatgcgtg gagaagcata tcata                                     25

<210> SEQ ID NO 24
<211> LENGTH: 21
<212> TYPE: DNA
<213> ORGANISM: Artificial
<220> FEATURE:
<223> OTHER INFORMATION: Probe 6
<220> FEATURE:
<221> NAME/KEY: modified_base
<222> LOCATION: (21)..(21)
<223> OTHER INFORMATION: modified with amino group.

<400> SEQUENCE: 24
attgagcaag tgtacagagc a                                         21

<210> SEQ ID NO 25
<211> LENGTH: 27
<212> TYPE: DNA
<213> ORGANISM: Artificial
<220> FEATURE:
<223> OTHER INFORMATION: Tag sequence T5

<400> SEQUENCE: 25
tggcaacatt tttcactggg tttatag                                   27

<210> SEQ ID NO 26
<211> LENGTH: 27
<212> TYPE: DNA
<213> ORGANISM: Artificial
<220> FEATURE:
<223> OTHER INFORMATION: Tag sequence T6

<400> SEQUENCE: 26
ggttagcttc caaccacgtg tagatca                                   27

<210> SEQ ID NO 27
<211> LENGTH: 47
<212> TYPE: DNA
<213> ORGANISM: Artificial
<220> FEATURE:
<223> OTHER INFORMATION: Primer T5-X-F
<220> FEATURE:
<221> NAME/KEY: misc_feature
<222> LOCATION: (27)..(28)
<223> OTHER INFORMATION: g at position 27 is jointed to g at position 28
      by azobenzene represented by Formula (23) of the specification.

<400> SEQUENCE: 27
tggcaacatt tttcactggg tttataggga aacagctatg accatga              47

<210> SEQ ID NO 28
<211> LENGTH: 47
<212> TYPE: DNA
<213> ORGANISM: Artificial

<220> FEATURE:
<223> OTHER INFORMATION: Primer T6-X-R
<220> FEATURE:
<221> NAME/KEY: misc_feature
<222> LOCATION: (27)..(28)
<223> OTHER INFORMATION: a at position 27 is jointed to t at position 28 by azobenzene represented by Formula (23) of the specification.

<400> SEQUENCE: 28
ggttagcttc caaccacgtg tagatcatct atgcggcatc agagcag        47

<210> SEQ ID NO 29
<211> LENGTH: 27
<212> TYPE: DNA
<213> ORGANISM: Artificial
<220> FEATURE:
<223> OTHER INFORMATION: Probe 7
<220> FEATURE:
<221> NAME/KEY: modified_base
<222> LOCATION: (27)..(27)
<223> OTHER INFORMATION: modified with amino group.

<400> SEQUENCE: 29
ctataaaccc agtgaaaaat gttgcca        27

<210> SEQ ID NO 30
<211> LENGTH: 27
<212> TYPE: DNA
<213> ORGANISM: Artificial
<220> FEATURE:
<223> OTHER INFORMATION: Probe 8
<220> FEATURE:
<221> NAME/KEY: modified_base
<222> LOCATION: (27)..(27)
<223> OTHER INFORMATION: modified with amino group.

<400> SEQUENCE: 30
gatcatacac gtggttggaa gctaacc        27

<210> SEQ ID NO 31
<211> LENGTH: 27
<212> TYPE: DNA
<213> ORGANISM: Artificial
<220> FEATURE:
<223> OTHER INFORMATION: Probe 9
<220> FEATURE:
<221> NAME/KEY: modified_base
<222> LOCATION: (27)..(27)
<223> OTHER INFORMATION: modified with thiol group.

<400> SEQUENCE: 31
ctataaaccc agtgaaaaat gttgcca        27

<210> SEQ ID NO 32
<211> LENGTH: 27
<212> TYPE: DNA
<213> ORGANISM: Artificial
<220> FEATURE:
<223> OTHER INFORMATION: Probe 10
<220> FEATURE:
<221> NAME/KEY: modified_base
<222> LOCATION: (20)..(20)
<223> OTHER INFORMATION: modified with biotin.

<400> SEQUENCE: 32
gatcatacac gtggttggaa gctaacc        27

<210> SEQ ID NO 33
<211> LENGTH: 27

```
<212> TYPE: DNA
<213> ORGANISM: Artificial
<220> FEATURE:
<223> OTHER INFORMATION: Probe 11

<400> SEQUENCE: 33
gatcatacac gtggttggaa gctaacc                                          27

<210> SEQ ID NO 34
<211> LENGTH: 27
<212> TYPE: DNA
<213> ORGANISM: Artificial
<220> FEATURE:
<223> OTHER INFORMATION: Tag sequence T7

<400> SEQUENCE: 34
tggcaacatt tttcactggg tttatag                                          27

<210> SEQ ID NO 35
<211> LENGTH: 27
<212> TYPE: DNA
<213> ORGANISM: Artificial
<220> FEATURE:
<223> OTHER INFORMATION: Tag sequence T8

<400> SEQUENCE: 35
ggttagcttc caaccacgtg tagatca                                          27

<210> SEQ ID NO 36
<211> LENGTH: 47
<212> TYPE: DNA
<213> ORGANISM: Artificial
<220> FEATURE:
<223> OTHER INFORMATION: Primer T7-X-F1
<220> FEATURE:
<221> NAME/KEY: misc_feature
<222> LOCATION: (27)..(28)
<223> OTHER INFORMATION: g at position 27 is jointed to g at position 28
      by azobenzene represented by Formula (23) of the specification.

<400> SEQUENCE: 36
tggcaacatt tttcactggg tttataggga acagctatg accatga                     47

<210> SEQ ID NO 37
<211> LENGTH: 47
<212> TYPE: DNA
<213> ORGANISM: Artificial
<220> FEATURE:
<223> OTHER INFORMATION: Primer T8-X-R1
<220> FEATURE:
<221> NAME/KEY: misc_feature
<222> LOCATION: (27)..(28)
<223> OTHER INFORMATION: a at position 27 is jointed to t at position 28
      by azobenzene represented by Formula (23) of the specification.

<400> SEQUENCE: 37
ggttagcttc caaccacgtg tagatcatct atgcggcatc agagcag                    47

<210> SEQ ID NO 38
<211> LENGTH: 25
<212> TYPE: DNA
<213> ORGANISM: Artificial
<220> FEATURE:
<223> OTHER INFORMATION: Tag sequence T9

<400> SEQUENCE: 38
cgcattgagc aagtgtacag agcat                                            25
```

<210> SEQ ID NO 39
<211> LENGTH: 25
<212> TYPE: DNA
<213> ORGANISM: Artificial
<220> FEATURE:
<223> OTHER INFORMATION: Tag sequence T10

<400> SEQUENCE: 39
attatgcgtg gagaagcata tcata                                             25

<210> SEQ ID NO 40
<211> LENGTH: 45
<212> TYPE: DNA
<213> ORGANISM: Artificial
<220> FEATURE:
<223> OTHER INFORMATION: Primer T9-X-F2
<220> FEATURE:
<221> NAME/KEY: misc_feature
<222> LOCATION: (25)..(26)
<223> OTHER INFORMATION: t at position 25 is jointed to a at position 26
      by azobenzene represented by Formula (23) of the specification.

<400> SEQUENCE: 40
cgcattgagc aagtgtacag agcatagcat tatgaattat atggt                       45

<210> SEQ ID NO 41
<211> LENGTH: 45
<212> TYPE: DNA
<213> ORGANISM: Artificial
<220> FEATURE:
<223> OTHER INFORMATION: Primer T10-X-R2
<220> FEATURE:
<221> NAME/KEY: misc_feature
<222> LOCATION: (25)..(26)
<223> OTHER INFORMATION: a at position 25 is jointed to t at position 26
      by azobenzene represented by Formula (23) of the specification.

<400> SEQUENCE: 41
attatgcgtg gagaagcata tcatattgtt tacatttata gcatc                       45

<210> SEQ ID NO 42
<211> LENGTH: 22
<212> TYPE: DNA
<213> ORGANISM: Artificial
<220> FEATURE:
<223> OTHER INFORMATION: Tag sequence T11

<400> SEQUENCE: 42
aattgcgcat gtccatgtgt aa                                                22

<210> SEQ ID NO 43
<211> LENGTH: 22
<212> TYPE: DNA
<213> ORGANISM: Artificial
<220> FEATURE:
<223> OTHER INFORMATION: Tag sequence T12

<400> SEQUENCE: 43
tactttagag gaaactgctg ag                                                22

<210> SEQ ID NO 44
<211> LENGTH: 42
<212> TYPE: DNA
<213> ORGANISM: Artificial
<220> FEATURE:
<223> OTHER INFORMATION: Primer T11-X-F3
<220> FEATURE:
<221> NAME/KEY: misc_feature

```
<222> LOCATION: (22)..(23)
<223> OTHER INFORMATION: a at position 22 is jointed to t at position 23
      by azobenzene represented by Formula (23) of the specification.

<400> SEQUENCE: 44
aattgcgcat gtccatgtgt aatggtttta aaactctgat ac                         42

<210> SEQ ID NO 45
<211> LENGTH: 42
<212> TYPE: DNA
<213> ORGANISM: Artificial
<220> FEATURE:
<223> OTHER INFORMATION: Primer T12-X-R3
<220> FEATURE:
<221> NAME/KEY: misc_feature
<222> LOCATION: (22)..(23)
<223> OTHER INFORMATION: g at position 22 is jointed to a at position 23
      by azobenzene represented by Formula (23) of the specification.

<400> SEQUENCE: 45
tactttagag gaaactgctg agagtatgat gagggtgtaa ca                         42

<210> SEQ ID NO 46
<211> LENGTH: 27
<212> TYPE: DNA
<213> ORGANISM: Artificial
<220> FEATURE:
<223> OTHER INFORMATION: Probe 12
<220> FEATURE:
<221> NAME/KEY: modified_base
<222> LOCATION: (27)..(27)
<223> OTHER INFORMATION: modified with amino group.

<400> SEQUENCE: 46
ctataaaccc agtgaaaaat gttgcca                                          27

<210> SEQ ID NO 47
<211> LENGTH: 25
<212> TYPE: DNA
<213> ORGANISM: Artificial
<220> FEATURE:
<223> OTHER INFORMATION: Probe 13
<220> FEATURE:
<221> NAME/KEY: modified_base
<222> LOCATION: (25)..(25)
<223> OTHER INFORMATION: modified with amino group.

<400> SEQUENCE: 47
ttgctctgta cacttgctca atgcg                                            25

<210> SEQ ID NO 48
<211> LENGTH: 22
<212> TYPE: DNA
<213> ORGANISM: Artificial
<220> FEATURE:
<223> OTHER INFORMATION: Probe 14
<220> FEATURE:
<221> NAME/KEY: modified_base
<222> LOCATION: (22)..(22)
<223> OTHER INFORMATION: modified with amino group.

<400> SEQUENCE: 48
ttacacatgg acatgcgcaa tt                                               22

<210> SEQ ID NO 49
<211> LENGTH: 27
<212> TYPE: DNA
<213> ORGANISM: Artificial
<220> FEATURE:
```

<223> OTHER INFORMATION: Probe 15
<220> FEATURE:
<221> NAME/KEY: modified_base
<222> LOCATION: (27)..(27)
<223> OTHER INFORMATION: modified with biotin.

<400> SEQUENCE: 49
gatcatacac gtggttggaa gctaacc                                27

<210> SEQ ID NO 50
<211> LENGTH: 25
<212> TYPE: DNA
<213> ORGANISM: Artificial
<220> FEATURE:
<223> OTHER INFORMATION: Probe 16
<220> FEATURE:
<221> NAME/KEY: modified_base
<222> LOCATION: (25)..(25)
<223> OTHER INFORMATION: modified with biotin.

<400> SEQUENCE: 50
tatgatatgc ttctccacgc ataat                                  25

<210> SEQ ID NO 51
<211> LENGTH: 22
<212> TYPE: DNA
<213> ORGANISM: Artificial
<220> FEATURE:
<223> OTHER INFORMATION: Probe 17
<220> FEATURE:
<221> NAME/KEY: modified_base
<222> LOCATION: (22)..(22)
<223> OTHER INFORMATION: modified with biotin.

<400> SEQUENCE: 51
ctcagcagtt tcctctaaag ta                                     22

<210> SEQ ID NO 52
<211> LENGTH: 20
<212> TYPE: DNA
<213> ORGANISM: Artificial
<220> FEATURE:
<223> OTHER INFORMATION: Common sequence KF1

<400> SEQUENCE: 52
tgggctgacc tagaggtctt                                        20

<210> SEQ ID NO 53
<211> LENGTH: 20
<212> TYPE: DNA
<213> ORGANISM: Artificial
<220> FEATURE:
<223> OTHER INFORMATION: Common sequence KR1

<400> SEQUENCE: 53
atgaaatgca ggccattcgg                                        20

<210> SEQ ID NO 54
<211> LENGTH: 40
<212> TYPE: DNA
<213> ORGANISM: Artificial
<220> FEATURE:
<223> OTHER INFORMATION: Primer KF1-Fj1

<400> SEQUENCE: 54
tgggctgacc tagaggtctt ggaaacagct atgaccatga                  40

<210> SEQ ID NO 55
<211> LENGTH: 40
<212> TYPE: DNA
<213> ORGANISM: Artificial
<220> FEATURE:
<223> OTHER INFORMATION: Primer KR1-Rj1

<400> SEQUENCE: 55
atgaaatgca ggccattcgg tctatgcggc atcagagcag                         40

<210> SEQ ID NO 56
<211> LENGTH: 20
<212> TYPE: DNA
<213> ORGANISM: Artificial
<220> FEATURE:
<223> OTHER INFORMATION: Common sequence KF2

<400> SEQUENCE: 56
ccggaacaga caccaggttt                                              20

<210> SEQ ID NO 57
<211> LENGTH: 20
<212> TYPE: DNA
<213> ORGANISM: Artificial
<220> FEATURE:
<223> OTHER INFORMATION: Common sequence KR2

<400> SEQUENCE: 57
gaagctgtac cgtcacatga                                              20

<210> SEQ ID NO 58
<211> LENGTH: 40
<212> TYPE: DNA
<213> ORGANISM: Artificial
<220> FEATURE:
<223> OTHER INFORMATION: Primer KF2-Fj2

<400> SEQUENCE: 58
ccggaacaga caccaggttt agcattatga attatatggt                         40

<210> SEQ ID NO 59
<211> LENGTH: 40
<212> TYPE: DNA
<213> ORGANISM: Artificial
<220> FEATURE:
<223> OTHER INFORMATION: Primer KR2-Rj2

<400> SEQUENCE: 59
gaagctgtac cgtcacatga ttgtttacat ttatagcatc                         40

<210> SEQ ID NO 60
<211> LENGTH: 20
<212> TYPE: DNA
<213> ORGANISM: Artificial
<220> FEATURE:
<223> OTHER INFORMATION: Common sequence KF3

<400> SEQUENCE: 60
ataccgatga gtgtgctacc                                              20

<210> SEQ ID NO 61
<211> LENGTH: 20
<212> TYPE: DNA
<213> ORGANISM: Artificial
<220> FEATURE:
<223> OTHER INFORMATION: Common sequence KR3

<400> SEQUENCE: 61
tggcctgtgt gacactatgc                                           20

<210> SEQ ID NO 62
<211> LENGTH: 40
<212> TYPE: DNA
<213> ORGANISM: Artificial
<220> FEATURE:
<223> OTHER INFORMATION: Primer KF3-Fj3

<400> SEQUENCE: 62
ataccgatga gtgtgctacc tggttttaaa actctgatac                     40

<210> SEQ ID NO 63
<211> LENGTH: 40
<212> TYPE: DNA
<213> ORGANISM: Artificial
<220> FEATURE:
<223> OTHER INFORMATION: Primer KR3-Rj3

<400> SEQUENCE: 63
tggcctgtgt gacactatgc agtatgatga gggtgtaaca                     40

<210> SEQ ID NO 64
<211> LENGTH: 27
<212> TYPE: DNA
<213> ORGANISM: Artificial
<220> FEATURE:
<223> OTHER INFORMATION: Tag sequence T16

<400> SEQUENCE: 64
tggcaacatt tttcactggg tttatag                                   27

<210> SEQ ID NO 65
<211> LENGTH: 27
<212> TYPE: DNA
<213> ORGANISM: Artificial
<220> FEATURE:
<223> OTHER INFORMATION: Tag sequence T17

<400> SEQUENCE: 65
ggttagcttc caaccacgtg tagatca                                   27

<210> SEQ ID NO 66
<211> LENGTH: 47
<212> TYPE: DNA
<213> ORGANISM: Artificial
<220> FEATURE:
<223> OTHER INFORMATION: Primer T16-X-KF1
<220> FEATURE:
<221> NAME/KEY: misc_feature
<222> LOCATION: (27)..(28)
<223> OTHER INFORMATION: g at position 27 is jointed to t at position 28
      by azobenzene represented by Formula (23) of the specification.

<400> SEQUENCE: 66
tggcaacatt tttcactggg tttatagtgg gctgacctag aggtctt             47

<210> SEQ ID NO 67
<211> LENGTH: 47
<212> TYPE: DNA
<213> ORGANISM: Artificial
<220> FEATURE:
<223> OTHER INFORMATION: Primer T17-X-KR1
<220> FEATURE:
<221> NAME/KEY: misc_feature
<222> LOCATION: (27)..(28)

<223> OTHER INFORMATION: a at position 27 is jointed to a at position 28
      by azobenzene represented by Formula (23) of the specification.

<400> SEQUENCE: 67
ggttagcttc caaccacgtg tagatcaatg aaatgcaggc cattcgg         47

<210> SEQ ID NO 68
<211> LENGTH: 25
<212> TYPE: DNA
<213> ORGANISM: Artificial
<220> FEATURE:
<223> OTHER INFORMATION: Tag sequence T18

<400> SEQUENCE: 68
cgcattgagc aagtgtacag agcat                                25

<210> SEQ ID NO 69
<211> LENGTH: 25
<212> TYPE: DNA
<213> ORGANISM: Artificial
<220> FEATURE:
<223> OTHER INFORMATION: Tag sequence T19

<400> SEQUENCE: 69
attatgcgtg gagaagcata tcata                                25

<210> SEQ ID NO 70
<211> LENGTH: 45
<212> TYPE: DNA
<213> ORGANISM: Artificial
<220> FEATURE:
<223> OTHER INFORMATION: Primer T18-X-KF2
<220> FEATURE:
<221> NAME/KEY: misc_feature
<222> LOCATION: (25)..(26)
<223> OTHER INFORMATION: t at position 25 is jointed to c at position 26
      by azobenzene represented by Formula (23) of the specification.

<400> SEQUENCE: 70
cgcattgagc aagtgtacag agcatccgga acagacacca ggttt          45

<210> SEQ ID NO 71
<211> LENGTH: 45
<212> TYPE: DNA
<213> ORGANISM: Artificial
<220> FEATURE:
<223> OTHER INFORMATION: Primer T19-X-KR2
<220> FEATURE:
<221> NAME/KEY: misc_feature
<222> LOCATION: (25)..(26)
<223> OTHER INFORMATION: a at position 25 is jointed to g at position 26
      by azobenzene represented by Formula (23) of the specification.

<400> SEQUENCE: 71
attatgcgtg gagaagcata tcatagaagc tgtaccgtca catga          45

<210> SEQ ID NO 72
<211> LENGTH: 22
<212> TYPE: DNA
<213> ORGANISM: Artificial
<220> FEATURE:
<223> OTHER INFORMATION: Tag sequence T20

<400> SEQUENCE: 72
aattgcgcat gtccatgtgt aa                                   22

<210> SEQ ID NO 73

```
<211> LENGTH: 22
<212> TYPE: DNA
<213> ORGANISM: Artificial
<220> FEATURE:
<223> OTHER INFORMATION: Tag sequence T21

<400> SEQUENCE: 73
tactttagag gaaactgctg ag                                              22

<210> SEQ ID NO 74
<211> LENGTH: 42
<212> TYPE: DNA
<213> ORGANISM: Artificial
<220> FEATURE:
<223> OTHER INFORMATION: Primer T20-X-KF3
<220> FEATURE:
<221> NAME/KEY: misc_feature
<222> LOCATION: (22)..(23)
<223> OTHER INFORMATION: a at position 22 is jointed to a at position 23
      by azobenzene represented by Formula (23) of the specification.

<400> SEQUENCE: 74
aattgcgcat gtccatgtgt aaataccgat gagtgtgcta cc                        42

<210> SEQ ID NO 75
<211> LENGTH: 42
<212> TYPE: DNA
<213> ORGANISM: Artificial
<220> FEATURE:
<223> OTHER INFORMATION: Primer T21-X-KR3
<220> FEATURE:
<221> NAME/KEY: misc_feature
<222> LOCATION: (22)..(23)
<223> OTHER INFORMATION: g at position 22 is jointed to t at position 23
      by azobenzene represented by Formula (23) of the specification.

<400> SEQUENCE: 75
tactttagag gaaactgctg agtggcctgt gtgacactat gc                        42

<210> SEQ ID NO 76
<211> LENGTH: 27
<212> TYPE: DNA
<213> ORGANISM: Artificial
<220> FEATURE:
<223> OTHER INFORMATION: Probe 18
<220> FEATURE:
<221> NAME/KEY: modified_base
<222> LOCATION: (27)..(27)
<223> OTHER INFORMATION: modified with amino group.

<400> SEQUENCE: 76
ctataaaccc agtgaaaaat gttgcca                                         27

<210> SEQ ID NO 77
<211> LENGTH: 25
<212> TYPE: DNA
<213> ORGANISM: Artificial
<220> FEATURE:
<223> OTHER INFORMATION: Probe 19
<220> FEATURE:
<221> NAME/KEY: modified_base
<222> LOCATION: (25)..(25)
<223> OTHER INFORMATION: modified with amino group.

<400> SEQUENCE: 77
ttgctctgta cacttgctca atgcg                                           25

<210> SEQ ID NO 78
<211> LENGTH: 22
```

```
<212> TYPE: DNA
<213> ORGANISM: Artificial
<220> FEATURE:
<223> OTHER INFORMATION: Probe 20
<220> FEATURE:
<221> NAME/KEY: modified_base
<222> LOCATION: (22)..(22)
<223> OTHER INFORMATION: modified with amino group.

<400> SEQUENCE: 78
ttacacatgg acatgcgcaa tt                                              22

<210> SEQ ID NO 79
<211> LENGTH: 27
<212> TYPE: DNA
<213> ORGANISM: Artificial
<220> FEATURE:
<223> OTHER INFORMATION: Probe 21
<220> FEATURE:
<221> NAME/KEY: modified_base
<222> LOCATION: (27)..(27)
<223> OTHER INFORMATION: modified with biotin.

<400> SEQUENCE: 79
gatcatacac gtggttggaa gctaacc                                         27

<210> SEQ ID NO 80
<211> LENGTH: 25
<212> TYPE: DNA
<213> ORGANISM: Artificial
<220> FEATURE:
<223> OTHER INFORMATION: Probe 22
<220> FEATURE:
<221> NAME/KEY: modified_base
<222> LOCATION: (25)..(25)
<223> OTHER INFORMATION: modified with biotin.

<400> SEQUENCE: 80
tatgatatgc ttctccacgc ataat                                           25

<210> SEQ ID NO 81
<211> LENGTH: 22
<212> TYPE: DNA
<213> ORGANISM: Artificial
<220> FEATURE:
<223> OTHER INFORMATION: Probe 23
<220> FEATURE:
<221> NAME/KEY: modified_base
<222> LOCATION: (22)..(22)
<223> OTHER INFORMATION: modified with biotin.

<400> SEQUENCE: 81
ctcagcagtt tcctctaaag ta                                              22

<210> SEQ ID NO 82
<211> LENGTH: 27
<212> TYPE: DNA
<213> ORGANISM: Artificial
<220> FEATURE:
<223> OTHER INFORMATION: Tag sequence T25

<400> SEQUENCE: 82
tggcaacatt tttcactggg tttatag                                         27

<210> SEQ ID NO 83
<211> LENGTH: 27
<212> TYPE: DNA
<213> ORGANISM: Artificial
<220> FEATURE:
```

<223> OTHER INFORMATION: Tag sequence T26

<400> SEQUENCE: 83
ggttagcttc caaccacgtg tagatca    27

<210> SEQ ID NO 84
<211> LENGTH: 20
<212> TYPE: DNA
<213> ORGANISM: Artificial
<220> FEATURE:
<223> OTHER INFORMATION: Primer F

<400> SEQUENCE: 84
ggaaacagct atgaccatga    20

<210> SEQ ID NO 85
<211> LENGTH: 20
<212> TYPE: DNA
<213> ORGANISM: Artificial
<220> FEATURE:
<223> OTHER INFORMATION: Primer R

<400> SEQUENCE: 85
tctatgcggc atcagagcag    20

<210> SEQ ID NO 86
<211> LENGTH: 47
<212> TYPE: DNA
<213> ORGANISM: Artificial
<220> FEATURE:
<223> OTHER INFORMATION: Primer T25-X-F
<220> FEATURE:
<221> NAME/KEY: misc_feature
<222> LOCATION: (27)..(28)
<223> OTHER INFORMATION: g at position 27 is jointed to g at position 28
      by azobenzene represented by Formula (23) of the specification.

<400> SEQUENCE: 86
tggcaacatt tttcactggg tttataggga aacagctatg accatga    47

<210> SEQ ID NO 87
<211> LENGTH: 47
<212> TYPE: DNA
<213> ORGANISM: Artificial
<220> FEATURE:
<223> OTHER INFORMATION: Primer T26-X-R
<220> FEATURE:
<221> NAME/KEY: misc_feature
<222> LOCATION: (27)..(28)
<223> OTHER INFORMATION: a at position 27 is jointed to t at position 28
      by azobenzene represented by Formula (23) of the specification.

<400> SEQUENCE: 87
ggttagcttc caaccacgtg tagatcatct atgcggcatc agagcag    47

<210> SEQ ID NO 88
<211> LENGTH: 27
<212> TYPE: DNA
<213> ORGANISM: Artificial
<220> FEATURE:
<223> OTHER INFORMATION: Probe 24
<220> FEATURE:
<221> NAME/KEY: modified_base
<222> LOCATION: (27)..(27)
<223> OTHER INFORMATION: modified with FITC.

<400> SEQUENCE: 88
ctataaaccc agtgaaaaat gttgcca    27

<210> SEQ ID NO 89
<211> LENGTH: 27
<212> TYPE: DNA
<213> ORGANISM: Artificial
<220> FEATURE:
<223> OTHER INFORMATION: Probe 25
<220> FEATURE:
<221> NAME/KEY: modified_base
<222> LOCATION: (27)..(27)
<223> OTHER INFORMATION: modified with biotin.

<400> SEQUENCE: 89
gatcatacac gtggttggaa gctaacc                                       27

<210> SEQ ID NO 90
<211> LENGTH: 50
<212> TYPE: DNA
<213> ORGANISM: Artificial
<220> FEATURE:
<223> OTHER INFORMATION: Target 1 (WT)

<400> SEQUENCE: 90
cacaccgcat atggtgcact ctcagtacaa tctgctctga tgccgcatag              50

<210> SEQ ID NO 91
<211> LENGTH: 50
<212> TYPE: DNA
<213> ORGANISM: Artificial
<220> FEATURE:
<223> OTHER INFORMATION: Target 2 (MT)

<400> SEQUENCE: 91
cacaccgcat atggtgcact ctcagtacaa gctgctctga tgccgcatag              50

<210> SEQ ID NO 92
<211> LENGTH: 27
<212> TYPE: DNA
<213> ORGANISM: Artificial
<220> FEATURE:
<223> OTHER INFORMATION: Tag sequence T27

<400> SEQUENCE: 92
tggcaacatt tttcactggg tttatag                                       27

<210> SEQ ID NO 93
<211> LENGTH: 27
<212> TYPE: DNA
<213> ORGANISM: Artificial
<220> FEATURE:
<223> OTHER INFORMATION: Tag sequence T28

<400> SEQUENCE: 93
ggttagcttc caaccacgtg tagatca                                       27

<210> SEQ ID NO 94
<211> LENGTH: 25
<212> TYPE: DNA
<213> ORGANISM: Artificial
<220> FEATURE:
<223> OTHER INFORMATION: Tag sequence T29

<400> SEQUENCE: 94
cgcattgagc aagtgtacag agcat                                         25

<210> SEQ ID NO 95

```
<211> LENGTH: 20
<212> TYPE: DNA
<213> ORGANISM: Artificial
<220> FEATURE:
<223> OTHER INFORMATION: Primer Fwt

<400> SEQUENCE: 95
cacaccgcat atggtgcact                                              20

<210> SEQ ID NO 96
<211> LENGTH: 20
<212> TYPE: DNA
<213> ORGANISM: Artificial
<220> FEATURE:
<223> OTHER INFORMATION: Primer Rwt

<400> SEQUENCE: 96
ctatgcggca tcagagcaga                                              20

<210> SEQ ID NO 97
<211> LENGTH: 20
<212> TYPE: DNA
<213> ORGANISM: Artificial
<220> FEATURE:
<223> OTHER INFORMATION: Primer Rmt

<400> SEQUENCE: 97
ctatgcggca tcagagcagc                                              20

<210> SEQ ID NO 98
<211> LENGTH: 47
<212> TYPE: DNA
<213> ORGANISM: Artificial
<220> FEATURE:
<223> OTHER INFORMATION: Primer T27-X-Fwt
<220> FEATURE:
<221> NAME/KEY: misc_feature
<222> LOCATION: (27)..(28)
<223> OTHER INFORMATION: g at position 27 is jointed to c at position 28
      by azobenzene represented by Formula (23) of the specification.

<400> SEQUENCE: 98
tggcaacatt tttcactggg tttatagcac accgcatatg gtgcact                47

<210> SEQ ID NO 99
<211> LENGTH: 48
<212> TYPE: DNA
<213> ORGANISM: Artificial
<220> FEATURE:
<223> OTHER INFORMATION: Primer T28-X-Rwt
<220> FEATURE:
<221> NAME/KEY: misc_feature
<222> LOCATION: (27)..(28)
<223> OTHER INFORMATION: a at position 27 is jointed to t at position 28
      by azobenzene represented by Formula (23) of the specification.

<400> SEQUENCE: 99
ggttagcttc caaccacgtg tagatcatct atgcggcatc agagcaga               48

<210> SEQ ID NO 100
<211> LENGTH: 46
<212> TYPE: DNA
<213> ORGANISM: Artificial
<220> FEATURE:
<223> OTHER INFORMATION: Primer T29-X-Rmt
<220> FEATURE:
<221> NAME/KEY: misc_feature
<222> LOCATION: (25)..(26)
<223> OTHER INFORMATION: t at position 25 is jointed to t at position 26
``` by azobenzene represented by Formula (23) of the specification.

<400> SEQUENCE: 100
cgcattgagc aagtgtacag agcattctat gcggcatcag agcagc                46

<210> SEQ ID NO 101
<211> LENGTH: 27
<212> TYPE: DNA
<213> ORGANISM: Artificial
<220> FEATURE:
<223> OTHER INFORMATION: Probe 26
<220> FEATURE:
<221> NAME/KEY: modified_base
<222> LOCATION: (27)..(27)
<223> OTHER INFORMATION: modified with thiol group.

<400> SEQUENCE: 101
ctataaaccc agtgaaaaat gttgcca                                     27

<210> SEQ ID NO 102
<211> LENGTH: 27
<212> TYPE: DNA
<213> ORGANISM: Artificial
<220> FEATURE:
<223> OTHER INFORMATION: Probe 27
<220> FEATURE:
<221> NAME/KEY: modified_base
<222> LOCATION: (20)..(20)
<223> OTHER INFORMATION: modified with biotin.

<400> SEQUENCE: 102
gatcatacac gtggttggaa gctaacc                                     27

<210> SEQ ID NO 103
<211> LENGTH: 25
<212> TYPE: DNA
<213> ORGANISM: Artificial
<220> FEATURE:
<223> OTHER INFORMATION: Probe 28
<220> FEATURE:
<221> NAME/KEY: modified_base
<222> LOCATION: (25)..(25)
<223> OTHER INFORMATION: modified with biotin.

<400> SEQUENCE: 103
ttgctctgta cacttgctca atgcg                                       25

<210> SEQ ID NO 104
<211> LENGTH: 49
<212> TYPE: DNA
<213> ORGANISM: Artificial
<220> FEATURE:
<223> OTHER INFORMATION: Primer T7-X-Fwtr
<220> FEATURE:
<221> NAME/KEY: misc_feature
<222> LOCATION: (27)..(28)
<223> OTHER INFORMATION: g at position 27 is jointed to c at position 28
      by the 3'-3' and 5'-5' bind represented by Formula (1) of the
      specification.

<400> SEQUENCE: 104
tggcaacatt tttcactggg tttatagcat cacaatcaac ttatggtgg             49

<210> SEQ ID NO 105
<211> LENGTH: 48
<212> TYPE: DNA
<213> ORGANISM: Artificial
<220> FEATURE:
<223> OTHER INFORMATION: Primer T8-X-Rwtr

```
<220> FEATURE:
<221> NAME/KEY: misc_feature
<222> LOCATION: (27)..(28)
<223> OTHER INFORMATION: a at position 27 is jointed to t at position 28
      by the 3'-3' and 5'-5' bind represented by Formula (1) of the
      specification.

<400> SEQUENCE: 105
ggttagcttc caaccacgtg tagatcattt gggagttgag acgggtta                      48

<210> SEQ ID NO 106
<211> LENGTH: 46
<212> TYPE: DNA
<213> ORGANISM: Artificial
<220> FEATURE:
<223> OTHER INFORMATION: Primer T9-X-FFAG
<220> FEATURE:
<221> NAME/KEY: misc_feature
<222> LOCATION: (25)..(26)
<223> OTHER INFORMATION: t at position 25 is jointed to a at position 26
      by the 3'-3' and 5'-5' bind represented by Formula (1) of the
      specification.

<400> SEQUENCE: 106
cgcattgagc aagtgtacag agcataacgc cataaccagc ccgatt                        46

<210> SEQ ID NO 107
<211> LENGTH: 45
<212> TYPE: DNA
<213> ORGANISM: Artificial
<220> FEATURE:
<223> OTHER INFORMATION: Primer T10-X-RFAG
<220> FEATURE:
<221> NAME/KEY: misc_feature
<222> LOCATION: (25)..(26)
<223> OTHER INFORMATION: a at position 25 is jointed to c at position 26
      by the 3'-3' and 5'-5' bind represented by Formula (1) of the
      specification.

<400> SEQUENCE: 107
attatgcgtg gagaagcata tcatacctcc tgcctcccat tcttc                         45

<210> SEQ ID NO 108
<211> LENGTH: 44
<212> TYPE: DNA
<213> ORGANISM: Artificial
<220> FEATURE:
<223> OTHER INFORMATION: Primer T11-X-Fagg
<220> FEATURE:
<221> NAME/KEY: misc_feature
<222> LOCATION: (22)..(23)
<223> OTHER INFORMATION: a at position 22 is jointed to c at position 23
      by the 3'-3' and 5'-5' bind represented by Formula (1) of the
      specification.

<400> SEQUENCE: 108
aattgcgcat gtccatgtgt aacgaaggaa accccgcaat aaat                          44

<210> SEQ ID NO 109
<211> LENGTH: 44
<212> TYPE: DNA
<213> ORGANISM: Artificial
<220> FEATURE:
<223> OTHER INFORMATION: Primer T12-X-Ragg
<220> FEATURE:
<221> NAME/KEY: misc_feature
<222> LOCATION: (22)..(23)
<223> OTHER INFORMATION: g at position 22 is jointed to c at position 23
      by the 3'-3' and 5'-5' bind represented by Formula (1) of the
      specification.
```

<400> SEQUENCE: 109
tactttagag gaaactgctg agcgacgcta tttaccttgt tgag                44

<210> SEQ ID NO 110
<211> LENGTH: 27
<212> TYPE: DNA
<213> ORGANISM: Artificial
<220> FEATURE:
<223> OTHER INFORMATION: Probe 29
<220> FEATURE:
<221> NAME/KEY: modified_base
<222> LOCATION: (27)..(27)
<223> OTHER INFORMATION: modified with thiol group.

<400> SEQUENCE: 110
ctataaaccc agtgaaaaat gttgcca                                   27

<210> SEQ ID NO 111
<211> LENGTH: 25
<212> TYPE: DNA
<213> ORGANISM: Artificial
<220> FEATURE:
<223> OTHER INFORMATION: Probe 30
<220> FEATURE:
<221> NAME/KEY: modified_base
<222> LOCATION: (25)..(25)
<223> OTHER INFORMATION: modified with thiol group.

<400> SEQUENCE: 111
ttgctctgta cacttgctca atgcg                                     25

<210> SEQ ID NO 112
<211> LENGTH: 22
<212> TYPE: DNA
<213> ORGANISM: Artificial
<220> FEATURE:
<223> OTHER INFORMATION: Probe 31
<220> FEATURE:
<221> NAME/KEY: modified_base
<222> LOCATION: (22)..(22)
<223> OTHER INFORMATION: modified with thiol group.

<400> SEQUENCE: 112
ttacacatgg acatgcgcaa tt                                        22

<210> SEQ ID NO 113
<211> LENGTH: 1668
<212> TYPE: DNA
<213> ORGANISM: Artificial Sequence
<220> FEATURE:
<223> OTHER INFORMATION: Gene A

<400> SEQUENCE: 113
aaatgtgctg agcgtcccat ctggcctggt cctaggtacc tggtgtgccg gaagagccca      60
gcacgcactg aggcggccat gggactgctg atcggggatg ttctgggggcc cctggccata   120 gccgtggccc tcttcctgct cctggtggac cttctgcaca ggcgcagatt ctgggctgcc    180
cgcttcccgc caggccccat gccgctgccg ctgctgggca acctgctgca gatggacttc    240
caggacacgc tcttctactt cgaccggctg cggcgccgct cggggacgt gttcagcctg     300 cagctggcct ggacgcccgt ggtcgtgctc aacggcctgg aggccgtgcg cgaggcattg    360
gtttatcaca gcgaggacac tgccgaccgc ccacctatgc cgatctacga gcacctgggg    420
ttcgggccgc gctcccaagg ggtgttcatg gcgcgctacg ggcgcgagtg gcgcgagcag    480
cggcgcttcg ccttgtccac cctgcgcaac ttcggcctgg gcaagaagtc actggagcag    540

```
tgggtgaccg aggaggcctc gtgcctctgt gcagccttcg ccgaccatgc cggacgccct      600
tttagcccca aggcccttct gaataaagct gtgagcaacg tgatcacttc cctcacctac      660
gggcgccgct tcgggtacga cgacccgcgc ctccacaagc tgatagacgg agcactgaag      720
ggactgcagg aggacagcgg cttcgcgcgt gaggccctga actccatccc tgtgctcctg      780
cgcatcccgg gactggctga caaggtcttc tcaagccaga aggccttact gaccctcctg      840
aatgaactag tccaggagca caggatcacc cgggacccag cccagccacc caagacctg       900 actgacgcct tcctggatga aatagaaaag ctaggggga accccgagag cagcttcaat       960
gatgagaaca tgctcatggt gacagccgac ctgtttctgg ctgggatgct gtccacctca     1020
accacgctgg cctgggccct cctgctcatg atcttgcacc cggacgtgca gcgacgcgtc     1080
caacaggaga tagatgaagt gttagggccg gtgcagcgac cagcgatggc ggaccagacc     1140
cgcatgccct tcaccatggc cgtgatgcat gaggtacagc gctttgggga cctcgtccca     1200
ctgggcatgc cccacatgac atcccgagac attgaagtac agggctttct catccccaag     1260
gggacaacac ttatcaccaa cctatcgtca gtgctgaagg acaagacggt ctggaagaag     1320
cccttccgtt tccaccccga gcacttcctg gatgcccagg ccaattcgt caagcaggag      1380 gccttcatgc ccttctctgc aggccgccgc gtatgcctcg gggagcccct ggcccgcatg     1440
gagttcttcc tcttcttcac ctgtctgcta cagcgcttca gcttttccgt gcctgtgggg     1500
caaccccggc ccagcgacca tggtgtcttt tccttcctga tgatcccacc ccctaccag      1560 ctctgtgccg tgccccgcta ggaggaggaa ccagccccccc aactggctcc tcagcagggg    1620
ccctgatatg caataaacca gtttggcggt tccaaaaaaa aaaaaaaa                  1668

<210> SEQ ID NO 114
<211> LENGTH: 2686
<212> TYPE: DNA
<213> ORGANISM: Artificial Sequence
<220> FEATURE:
<223> OTHER INFORMATION: pUC19

<400> SEQUENCE: 114
gacgaaaggg cctcgtgata cgcctatttt tataggttaa tgtcatgata ataatggttt       60
cttagacgtc aggtggcact tttcggggaa atgtgcgcgg aaccccctatt tgtttatttt     120 tctaaataca ttcaaatatg tatccgctca tgagacaata accctgataa atgcttcaat     180
aatattgaaa aaggaagagt atgagtattc aacatttccg tgtcgccctt attccctttt     240
ttgcggcatt ttgccttcct gttttgctc acccagaaac gctggtgaaa gtaaagatg       300 ctgaagatca gttgggtgca cgagtgggtt acatcgaact ggatctcaac agcggtaaga    360
tccttgagag ttttcgcccc gaagaacgtt ttccaatgat gagcactttt aaagttctgc     420
tatgtggcgc ggtattatcc cgtattgacg ccgggcaaga gcaactcggt cgccgcatac     480
actattctca gaatgacttg gttgagtact caccagtcac agaaaagcat cttacggatg     540
gcatgacagt aagagaatta tgcagtgctg ccataaccat gagtgataac actgcggcca    600
acttacttct gacaacgatc ggaggaccga aggagctaac cgcttttttg cacaacatgg     660
gggatcatgt aactcgcctt gatcgttggg aaccggagct gaatgaagcc ataccaaacg     720
acgagcgtga caccacgatg cctgtagcaa tggcaacaac gttgcgcaaa ctattaactg     780
gcgaactact tactctagct tcccggcaac aattaataga ctggatggag gcggataaag     840
ttgcaggacc acttctgcgc tcggcccttc cggctggctg gtttattgct gataaatctg     900
```

```
gagccggtga gcgtgggtct cgcggtatca ttgcagcact ggggccagat ggtaagccct      960
cccgtatcgt agttatctac acgacgggga gtcaggcaac tatggatgaa cgaaatagac     1020
agatcgctga gataggtgcc tcactgatta agcattggta actgtcagac caagtttact     1080
catatatact ttagattgat ttaaaacttc attttaatt taaaaggatc taggtgaaga      1140 tccttttga taatctcatg accaaaatcc cttaacgtga gttttcgttc cactgagcgt      1200 cagacccgt agaaaagatc aaaggatctt cttgagatcc ttttttctg cgcgtaatct       1260 gctgcttgca acaaaaaaa ccaccgctac cagcggtggt ttgtttgccg gatcaagagc      1320
taccaactct ttttccgaag gtaactggct tcagcagagc gcagatacca aatactgttc     1380
ttctagtgta gccgtagtta ggccaccact tcaagaactc tgtagcaccg cctacatacc     1440
tcgctctgct aatcctgtta ccagtggctg ctgccagtgg cgataagtcg tgtcttaccg     1500
ggttggactc aagacgatag ttaccggata aggcgcagcg gtcgggctga acggggggtt     1560
cgtgcacaca gcccagcttg gagcgaacga cctacaccga actgagatac ctacagcgtg     1620
agctatgaga aagcgccacg cttcccgaag ggagaaaggc ggacaggtat ccggtaagcg     1680
gcagggtcgg aacaggagag cgcacgaggg agcttccagg gggaaacgcc tggtatcttt     1740
atagtcctgt cgggtttcgc cacctctgac ttgagcgtcg attttgtga tgctcgtcag      1800 gggggcggag cctatggaaa aacgccagca acgcggcctt tttacggttc ctggccttt      1860 gctggccttt tgctcacatg ttctttcctg cgttatcccc tgattctgtg ataaccgta      1920 ttaccgcctt tgagtgagct gataccgctc gccgcagccg aacgaccgag cgcagcgagt     1980
cagtgagcga ggaagcggaa gagcgcccaa tacgcaaacc gcctctcccc gcgcgttggc     2040
cgattcatta atgcagctgg cacgacaggt ttcccgactg gaaagcgggc agtgagcgca     2100
acgcaattaa tgtgagttag ctcactcatt aggcaccca ggctttacac tttatgcttc      2160
cggctcgtat gttgtgtgga attgtgagcg gataacaatt tcacacagga aacagctatg     2220
accatgatta cgccaagctt gcatgcctgc aggtcgactc tagaggatcc ccgggtaccg     2280
agctcgaatt cactggccgt cgttttacaa cgtcgtgact gggaaaaccc tggcgttacc     2340
caacttaatc gccttgcagc acatccccct ttcgccagct ggcgtaatag cgaagaggcc     2400
cgcaccgatc gcccttccca acagttgcgc agcctgaatg gcgaatggcg cctgatgcgg     2460
tattttctcc ttacgcatct gtgcggtatt tcacaccgca tatggtgcac tctcagtaca     2520
atctgctctg atgccgcata gttaagccag ccccgacacc cgccaacacc cgctgacgcg     2580
ccctgacggg cttgtctgct cccggcatcc gcttacagac aagctgtgac cgtctccggg     2640
agctgcatgt gtcagaggtt ttcaccgtca tcaccgaaac gcgcga                    2686
```

<210> SEQ ID NO 115
<211> LENGTH: 4360
<212> TYPE: DNA
<213> ORGANISM: Artificial Sequence
<220> FEATURE:
<223> OTHER INFORMATION: pUC19/Gene A

<400> SEQUENCE: 115

```
gacgaaaggg cctcgtgata cgcctatttt tataggttaa tgtcatgata ataatggttt       60
cttagacgtc aggtggcact tttcggggaa atgtgcgcgg aacccctatt tgtttatttt      120
tctaaataca ttcaaatatg tatccgctca tgagacaata accctgataa atgcttcaat     180
aatattgaaa aaggaagagt atgagtattc aacatttccg tgtcgccctt attcccttt      240 ttgcggcatt ttgccttcct gtttttgctc acccagaaac gctggtgaaa gtaaaagatg     300
```

```
ctgaagatca gttgggtgca cgagtgggtt acatcgaact ggatctcaac agcggtaaga      360
tccttgagag ttttcgcccc gaagaacgtt ttccaatgat gagcactttt aaagttctgc      420
tatgtggcgc ggtattatcc cgtattgacg ccgggcaaga gcaactcggt cgccgcatac      480
actattctca gaatgacttg gttgagtact caccagtcac agaaaagcat cttacggatg      540
gcatgacagt aagagaatta tgcagtgctg ccataaccat gagtgataac actgcggcca      600
acttacttct gacaacgatc ggaggaccga aggagctaac cgcttttttg cacaacatgg      660
gggatcatgt aactcgcctt gatcgttggg aaccggagct gaatgaagcc ataccaaacg      720
acgagcgtga caccacgatg cctgtagcaa tggcaacaac gttgcgcaaa ctattaactg      780
gcgaactact tactctagct tcccggcaac aattaataga ctggatggag gcggataaag      840
ttgcaggacc acttctgcgc tcggcccttc cggctggctg gtttattgct gataaatctg      900
gagccggtga gcgtgggtct cgcggtatca ttgcagcact ggggccagat ggtaagccct      960
cccgtatcgt agttatctac acgacgggga gtcaggcaac tatggatgaa cgaaatagac     1020
agatcgctga gataggtgcc tcactgatta agcattggta actgtcagac caagtttact     1080
catatatact ttagattgat ttaaaacttc atttttaatt taaaaggatc taggtgaaga     1140
tcctttttga taatctcatg accaaaatcc cttaacgtga gttttcgttc cactgagcgt     1200 cagacccccgt agaaaagatc aaaggatctt cttgagatcc ttttttttctg cgcgtaatct     1260
```

| | |
|---|---|
| cgatctacga gcacctgggg ttcgggccgc gctcccaagg ggtgttcatg gcgcgctacg | 2700 |
| ggcgcgagtg gcgcgagcag cggcgcttcg ccttgtccac cctgcgcaac ttcggcctgg | 2760 |
| gcaagaagtc actggagcag tgggtgaccg aggaggcctc gtgcctctgt gcagccttcg | 2820 |
| ccgaccatgc cggacgccct tttagcccca aggcccttct gaataaagct gtgagcaacg | 2880 |
| tgatcacttc cctcacctac gggcgccgct tcgggtacga cgacccgcgc ctccacaagc | 2940 |
| tgatagacgg agcactgaag ggactgcagg aggacagcgg cttcgcgcgt gaggccctga | 3000 |
| actccatccc tgtgctcctg cgcatcccgg gactggctga caaggtcttc tcaagccaga | 3060 |
| aggccttact gaccctcctg aatgaactag tccaggagca caggatcacc cgggacccag | 3120 |
| cccagccacc ccaagacctg actgacgcct tcctggatga aatagaaaag gctaggggga | 3180 |
| accccgagag cagcttcaat gatgagaaca tgctcatggt gacagccgac ctgtttctgg | 3240 |
| ctgggatgct gtccacctca accacgctgg cctgggccct cctgctcatg atcttgcacc | 3300 |
| cggacgtgca gcgacgcgtc caacaggaga tagatgaagt gttagggccg gtgcagcgac | 3360 |
| cagcgatggc ggaccagacc cgcatgccct tcaccatggc cgtgatgcat gaggtacagc | 3420 |
| gcttttgggga cctcgtccca ctgggcatgc cccacatgac atcccgagac attgaagtac | 3480 |
| agggctttct catccccaag gggacaacac ttatcaccaa cctatcgtca gtgctgaagg | 3540 |
| acaagacggt ctggaagaag cccttccgtt tccaccccga gcacttcctg gatgcccagg | 3600 |
| gccaattcgt caagcaggag gccttcatgc ccttctctgc aggccgccgc gtatgcctcg | 3660 |
| gggagcccct ggcccgcatg gagttcttcc tcttcttcac ctgtctgcta cagcgcttca | 3720 |
| gcttttccgt gcctgtgggg caaccccggc ccagcgacca tggtgtcttt tccttcctga | 3780 |
| tgatcccacc ccctaccag ctctgtgccg tgccccgcta ggaggaggaa ccagcccccc | 3840 |
| aactggctcc tcagcagggg ccctgatatg caataaacca gtttggcggt tccaaaaaaa | 3900 |
| aaaaaaaaaa gcttgcatgc ctgcaggtcg actctagagg atccccgggt accgagctcg | 3960 |
| aattcactgg ccgtcgtttt acaacgtcgt gactgggaaa accctggcgt tacccaactt | 4020 |
| aatcgccttg cagcacatcc ccctttcgcc agctggcgta atagcgaaga ggcccgcacc | 4080 |
| gatcgccctt cccaacagtt gcgcagcctg aatggcgaat ggcgcctgat gcggtatttt | 4140 |
| ctccttacgc atctgtgcgg tatttcacac cgcatatggt gcactctcag tacaatctgc | 4200 |
| tctgatgccg catagttaag ccagccccga cacccgccaa cacccgctga cgcgccctga | 4260 |
| cgggcttgtc tgctcccggc atccgcttac agacaagctg tgaccgtctc cgggagctgc | 4320 |
| atgtgtcaga ggttttcacc gtcatcaccg aaacgcgcga | 4360 |

<210> SEQ ID NO 116
<211> LENGTH: 20
<212> TYPE: DNA
<213> ORGANISM: Artificial Sequence
<220> FEATURE:
<223> OTHER INFORMATION: Primer F

<400> SEQUENCE: 116
ggaaacagct atgaccatga                                               20

<210> SEQ ID NO 117
<211> LENGTH: 20
<212> TYPE: DNA
<213> ORGANISM: Artificial Sequence
<220> FEATURE:
<223> OTHER INFORMATION: Primer R

<400> SEQUENCE: 117

```
tttcccagtc acgacgttgt                                              20

<210> SEQ ID NO 118
<211> LENGTH: 19
<212> TYPE: DNA
<213> ORGANISM: Artificial Sequence
<220> FEATURE:
<223> OTHER INFORMATION: Primer R-in

<400> SEQUENCE: 118
agtgcgtgct gggctcttc                                               19

<210> SEQ ID NO 119
<211> LENGTH: 47
<212> TYPE: DNA
<213> ORGANISM: Artificial Sequence
<220> FEATURE:
<223> OTHER INFORMATION: Primer T27-X-F
<220> FEATURE:
<221> NAME/KEY: misc_feature
<222> LOCATION: (27)..(28)
<223> OTHER INFORMATION: g at position 27 is jointed to g at position 28
      by the C6linker.

<400> SEQUENCE: 119
tggcaacatt tttcactggg tttataggga aacagctatg accatga                47

<210> SEQ ID NO 120
<211> LENGTH: 47
<212> TYPE: DNA
<213> ORGANISM: Artificial Sequence
<220> FEATURE:
<223> OTHER INFORMATION: Primer T28-X-R
<220> FEATURE:
<221> NAME/KEY: misc_feature
<222> LOCATION: (27)..(28)
<223> OTHER INFORMATION: a at position 27 is jointed to t at position 28
      by the C6linker.

<400> SEQUENCE: 120
ggttagcttc caaccacgtg tagatcattt cccagtcacg acgttgt                47

<210> SEQ ID NO 121
<211> LENGTH: 45
<212> TYPE: DNA
<213> ORGANISM: Artificial Sequence
<220> FEATURE:
<223> OTHER INFORMATION: Primer T27-X-F
<220> FEATURE:
<221> NAME/KEY: misc_feature
<222> LOCATION: (25)..(26)
<223> OTHER INFORMATION: t at position 25 is jointed to a at position 26
      by the C6linker.

<400> SEQUENCE: 121
cgcattgagc aagtgtacag agcatnagtg cgtgctgggc tcttc                  45
```

METHOD FOR AMPLIFYING NUCLEIC ACID AND METHOD FOR DETECTING AMPLIFIED NUCLEIC ACID

CROSS REFERENCE TO RELATED APPLICATIONS

This application is a National Phase filing under 35 U.S.C. §371 of PCT/JP2013/062488 filed on Apr. 26, 2013; and this application claims priority to Application No. 2012-103691 filed in Japan on Apr. 27, 2012. The entire content of each application is hereby incorporated by reference.

TECHNICAL FIELD

The present invention relates to a method for amplifying a nucleic acid and a method for detecting a nucleic acid amplified by this method.

BACKGROUND ART

Techniques for specifically amplifying a target nucleic acid sequence are very important for molecular biology research and clinical applications (e.g. genetic testing). An amplified product obtained by a nucleic acid amplification technique can be specifically detected, for example, by immobilizing a target sequence-containing nucleic acid fragment on a solid phase. In this method, the target nucleic acid is specifically immobilized on the solid phase, and non-specific nucleic acid sequences can then be easily removed by washing or the like. Thus, detection specificity can be enhanced.

In the method, the target nucleic acid may be captured on the solid phase by using an antigen-antibody or ligand-receptor pair capable of specifically binding together. For example, Non Patent Literature 1 discloses a method for detecting a PCR product amplified using a primer pair including a primer terminally modified with biotin and another primer modified with a fluorescent substance. This method includes contacting the PCR product with a streptavidin-agarose solid phase, forming a streptavidin-biotin complex to bond the PCR product to the solid phase, and measuring fluorescence of the complex, whereby the target amplified product can be detected.

Unfortunately, the number of antigen-antibody or ligand-receptor combinations usable for labeling is limited, which makes it substantially difficult to detect multiple target nucleic acids at one time. Another problem is the cost: fluorescently labeled nucleic acids are expensive.

Another method for capturing a target nucleic acid on a solid phase is to immobilize, on the solid phase, an oligonucleotide probe containing a sequence complementary to the target nucleic acid, and then indirectly immobilize the target nucleic acid on the solid phase through hybridization of the target nucleic acid and the probe. In this method, the intensity of a signal generated upon hybridization is detected. Such a nucleic acid analysis allows multiple target sequences to be analyzed at one time by using varied probe sequences.

In general, in order to hybridize an immobilized probe and a target nucleic acid on a solid phase, the double-stranded nucleic acid amplified by PCR needs to be denatured into single strands by heat treatment. Unfortunately, the heat treatment is troublesome and also has the problem of reduced hybridization efficiency due to reannealing. Another problem is that single-stranded DNA tends to easily curl into balls and is thus inferior in detection sensitivity. Patent Literature 1 discloses a method for amplifying a single-stranded nucleic acid using nuclease treatment without heat treatment; however, it is also troublesome to operate and has the problem of curling of single strands into balls.

The chromatography-based method disclosed in Patent Literature 2 is easy to operate and allows rapid and simple detection of target nucleic acids as compared to other nucleic acid detection methods. This is a gene detection method that includes the steps of: sampling genes from a cell, virus or bacterium, fragmenting the randomly sampled genes, and detecting a target gene, wherein these steps are continuously performed on a single device for detecting genes by transferring a liquid sample containing the randomly sampled genes or fragments thereof by capillary action. This method allows assessment of the presence of a target gene and identification of the type of gene. Still, Patent Literature 2 employs NASBA to amplify single-stranded nucleic acids. It has the problems associated with the use of single-stranded nucleic acids as described above.

In order to solve the above problems, Patent Literatures 3 and 4 propose the use of a primer region having on the 5' side a non-natural nucleic acid tag, a hairpin structure or a pseudoknot structure for inhibiting nucleic acid synthesis by DNA polymerase to leave a single-stranded region in one strand of a double-stranded nucleic acid after PCR reactions. This technique is advantageous in that an amplified double-stranded DNA product having a hybridizable single-stranded region at one end can be produced by only performing PCR reactions using such a special primer. However, it requires detection using fluorescent labeling or surface plasmon resonance imaging, which requires expensive special equipment. Thus, there are problems with speed and simplicity.

CITATION LIST

Patent Literature

Patent Literature 1: JP H05-252998 A
Patent Literature 2: JP 2006-201062 A
Patent Literature 3: WO 2006/095550
Patent Literature 4: JP 2009-296948 A Non Patent Literature Non Patent Literature 1: Analytical biochemistry, 193, 231-235, (1991)

SUMMARY OF INVENTION

Technical Problem

Genetic diagnosis or testing in clinical practice often requires the burdens of costs for patient testing and several hospital visits because it needs large-scale, expensive testing equipment and takes a long time for testing. In this context, there is a need for reducing the burdens on patients and testers while maintaining the accuracy of testing, and thus simple, rapid, highly-specific, and low-cost methods that do not require special equipment are being sought. The present invention was made to solve the above problems, and the present invention aims to provide a nucleic acid detection method which takes advantage of the high specificity of hybridization techniques, reduces the time length and the number of steps required for detection of PCR products, and allows simple and highly accurate detection by visual observation without the need of special equipment, as well as a providing nucleic acid detection device or kit. Meanwhile, conventional methods leave room for improvement in terms of time, effort and cost because they require the preparation of an expensive labeled tag for each target nucleic acid.

Solution to Problem

As a result of intensive studies to solve the above problems, the present inventors have independently found that the use of a set of primers each containing a tag region that is linked to the 5' end of the primer body and is not made double-stranded by a nucleic acid amplification reaction allows a target nucleic acid to be amplified into a double-stranded nucleic acid having a single-stranded region at each end thereof, and the thus amplified DNA fragment can be simply and accurately detected without the need of special equipment by binding the amplified fragment to a solid phase with an oligonucleotide probe capable of hybridizing to one of the single-stranded regions, and then detecting it. Thus, the present invention has been completed.

Specifically, the present invention relates to a method for amplifying a nucleic acid which includes performing a nucleic acid amplification reaction using primers whose 5' ends are each linked to a tag region that is not made double-stranded by the nucleic acid amplification reaction, thereby providing a nucleic acid having a single-stranded region at each end.

The tag region is preferably linked to the corresponding primer via a spacer.

The spacer preferably contains a nucleic acid derivative.

The nucleic acid derivative is preferably at least one selected from the group consisting of an L-nucleic acid, a 3-deoxy-2-hydroxy-dN, a nucleic acid containing a modified base, a nucleic acid containing a damaged base, a nucleic acid containing a modified phosphate linkage, an RNA, a 2'-OMe-N, and derivatives thereof.

The L-nucleic acid is preferably at least one selected from the group consisting of an L-DNA, an L-RNA, and derivatives thereof.

Preferably, the 3-deoxy-2-hydroxy-dN is linked to the primer via a 2'-5' linkage.

The nucleic acid containing a modified base preferably contains a chromophore or biotin.

The chromophore is preferably at least one selected from the group consisting of pyrene, etheno, pyrrolo, perylene, fluorescein, FITC, Cy3, Cy5, TAMRA, Dabcyl, and cyanine chromophores, and derivatives thereof.

The nucleic acid containing a damaged base is preferably at least one selected from the group consisting of an abasic nucleotide, a 5-hydroxymethyl-dN, and derivatives thereof.

The nucleic acid containing a modified phosphate linkage preferably contains a phosphorothioate or a derivative thereof.

The nucleic acid derivative is preferably linked to the primer via a 5'-5' linkage and to the tag region via a 3'-3' linkage.

The spacer preferably contains a non-nucleic acid derivative.

The non-nucleic acid derivative preferably has a D-threoninol scaffold.

Preferably, the D-threoninol scaffold incorporates at least one selected from the group consisting of azobenzene, biotin, EDTA, and a chromophore.

The chromophore is preferably at least one selected from the group consisting of pyrene, etheno, pyrrolo, perylene, fluorescein, FITC, Cy3, Cy5, TAMRA, Dabcyl, and cyanine chromophores, and derivatives thereof.

The non-nucleic acid derivative is preferably at least one selected from the group consisting of a carbon chain ($C_n$), a PEG chain (($CH_2CH_2O)_n$), a disulfide-containing chain ($C_nSSC_n$), and dithiol phosphoramidite.

The spacer preferably includes multiple types of spacers and/or multiple pieces of a spacer.

The present invention also relates to a method for detecting a nucleic acid which includes detecting a nucleic acid having a single-stranded region at each end amplified by the method for amplifying a nucleic acid.

The method preferably includes immobilizing a first oligonucleotide probe containing a sequence complementary to one of the single-stranded regions on a solid phase, and hybridizing the first oligonucleotide probe with the nucleic acid having a single-stranded region at each end.

The method preferably further includes bonding a second oligonucleotide probe containing a sequence complementary to the other single-stranded region to a labeling substance, and hybridizing the second oligonucleotide probe with the nucleic acid having a single-stranded region at each end.

The method preferably further includes identifying the nucleic acid by visual observation.

The labeling substance is preferably a colored carrier.

The method preferably includes detecting the nucleic acid having a single-stranded region at each end on a nucleic acid detection device.

The nucleic acid detection device is preferably an array or a chromatography device.

Advantageous Effects of Invention

Using tag regions that are not made double-stranded by nucleic acid amplification reactions, the present invention can provide nucleic acids that have a single-stranded region at each end and can be detected with high efficiency by hybridization.

Additionally, the present invention uses one of the single-stranded regions of such an amplified nucleic acid product to bind the amplified nucleic acid product in a specific manner to a solid phase, and further uses the other single-stranded region to form a complex with a labeling substance, thereby allowing simple and rapid assessment of the amplified nucleic acid product by visual observation without using special equipment. Moreover, the present invention improves detection sensitivity by detecting structurally stable double-stranded nucleic acids, as compared to detecting full-length single-stranded nucleic acids. Furthermore, the present invention allows simultaneous identification of two or more target nucleic acids in a sample by using multiple combinations of the single-stranded region of the amplified product to be bonded to the solid phase and an oligonucleotide probe on the solid phase that is complementary to the region. The present invention can add a single type of single-stranded region to any target nucleic acids via a low-cost joint primer, and the single type of single-stranded region enables detection using a single type of labeled tag and of device. In this case, it is not necessary to prepare an expensive labeled tag for each target nucleic acid, which leads to a great improvement in terms of time, effort and cost.

DESCRIPTION OF EMBODIMENTS

The present invention relates to a method for amplifying a nucleic acid which includes performing a nucleic acid amplification reaction using primers whose 5' ends are each linked to a tag region that is not made double-stranded by the nucleic acid amplification reaction, thereby providing a nucleic acid having a single-stranded region at each end. The nucleic acid may be a DNA or RNA, for example. The single-stranded regions at the respective ends of the amplified nucleic acid product each preferably contain natural nucleotides. The present invention also relates to a method for detecting a nucleic acid which includes detecting a nucleic acid having a single-stranded region at each end amplified by the above-mentioned method.

The nucleic acid having a single-stranded region at each end is obtained by a nucleic acid amplification reaction of a sample DNA (a template) using a certain set of primers. The nucleic acid having a single-stranded region at each end is preferably an amplified double-stranded DNA fragment having a single-stranded region at each end.

The sample DNA is not particularly limited and may be any DNA usable as a template in the nucleic acid amplification reaction. Specific examples include any DNAs derived from biological samples, such as blood, biological fluids, tissues, oral mucosa, hairs, nails, cultured cells, animals, plants, and microorganisms. The sample DNA may also be genomic DNA, cDNA, mitochondrial DNA, chloroplast DNA, or the like. Or, a cDNA synthesized from a RNA template by reverse transcription may be used. A suitable one may be appropriately selected from these DNAs according to the DNA fragment to be amplified. The sample DNA is not necessarily purified, and cells or a tissue containing the sample DNA can be used directly, without being purified, in the nucleic acid amplification reaction.

The amplified double-stranded DNA fragment having a single-stranded region at each end is preferably a product obtained by a nucleic acid amplification method using at least two primers each containing a tag region that is not made double-stranded by a nucleic acid amplification reaction. In this case, the single-stranded regions at the respective ends of the amplified double-stranded DNA fragment are derived from the tag regions that are not made double-stranded by a nucleic acid amplification reaction within the primers used in the nucleic acid amplification reaction.

Figure 1:
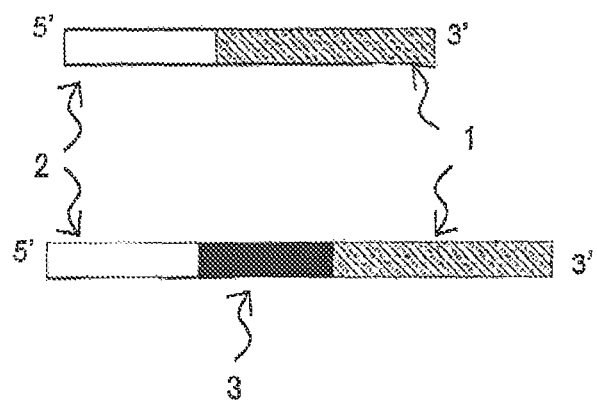
FIG. 1 is a schematic diagram of PCR primers in the present invention.

FIG. 1 shows primers for nucleic acid amplification. The primers contain a primer body region 1, and a tag region 2 which is located on the 5' side of the primer body and which is not made double-stranded by a nucleic acid amplification reaction. Optionally, a spacer region, which corresponds to a polymerase reaction inhibitory region 3, may be present between the primer body region and the tag region.

Figure 2:
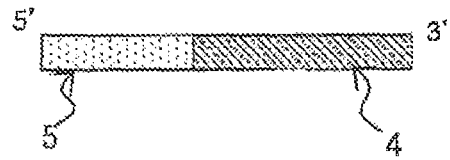
FIG. 2 is a schematic diagram of a first PCR primer in the present invention.
Figure 3:
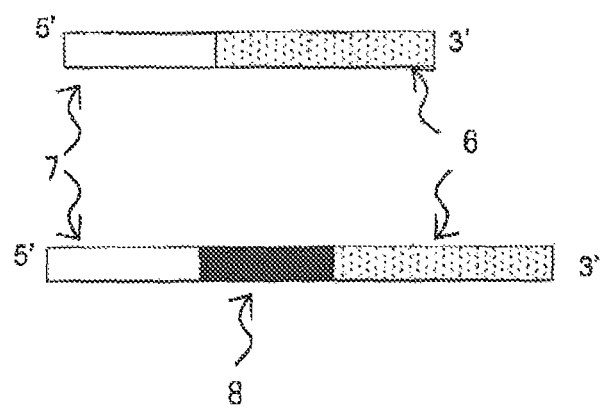
FIG. 3 is a schematic diagram of second PCR primers in the present invention.

The amplified double-stranded DNA fragment is also preferably a product obtained by a nucleic acid amplification method using a first primer set including primers each containing a sequence capable of hybridizing to the target nucleic acid template and a common sequence incapable of hybridizing to the template, and a second primer set including primers each containing a sequence capable of hybridizing to a sequence complementary to the common sequence and a tag region that is not made double-stranded by a nucleic acid amplification reaction. FIG. 2 shows a primer of the first PCR primer set. This first PCR primer (joint primer) is characterized by containing a primer body region 4 capable of hybridizing to the target nucleic acid template, and a common region 5 located on the 5' side of the primer body region and having a sequence common to a second primer. FIG. 3 shows primers of the second PCR primer set. The second primer is characterized by containing a primer body region 6 containing a sequence common to the first primer, and a tag region 7 which is located on the 5' side of the body region 6 and which is not made double-stranded by a nucleic acid amplification reaction. Optionally, a spacer region, which corresponds to a polymerase reaction inhibitory region 8, may be present between the second primer body region and the tag region.

The term "primer body region" refers to an oligonucleotide region having a base sequence capable of functioning as a primer in a nucleic acid amplification reaction. Specifically, this region is a base sequence capable of hybridizing to the 5' end or 3' end of a target base sequence of a target nucleic acid, and in general is a base sequence complementary to a base sequence at the 5' end or 3' end of the target base sequence. Such a primer body region may contain a base deletion or insertion, or a mismatch site as long as it is capable of specifically binding to the target nucleic acid. The primer body region preferably has a length of at least 8 bases, more preferably at least 12 bases, and still more preferably at least 15 bases. The maximum chain length of the primers is not particularly limited, and is generally at most 50 bases, and preferably at most 40 bases, from the viewpoint of their synthesis costs and other factors.

The tag regions of the primers each preferably contain natural nucleotides. The term "natural nucleotide" means a nucleotide composed of a natural base (adenine, thymine, guanine, cytosine, or uracil), a sugar moiety (deoxyribose or ribose), and a phosphate group, all of which are not artificially modified. The natural nucleotide may be a D-nucleotide or L-nucleotide. The term "D-nucleotide" refers to a nucleotide containing D-deoxyribose or D-ribose. Likewise, the term "L-nucleotide" refers to a nucleotide containing L-deoxyribose or L-ribose. The use of such a tag region containing natural nucleotides is effective for easy and low-cost synthesis. The proportion of natural nucleotides in the tag region of each primer is preferably at least 5%, more preferably at least 20%, still more preferably at least 50%, further more preferably at least 70%, and most preferably at least 90%. The length of the tag region is not particularly limited, and the tag region may be of any length sufficient to hybridize to a complementary nucleic acid strand. The length is generally 5 bases to 60 bases, and preferably 6 bases to 40 bases.

The tag regions of the primers each preferably have a nucleic acid sequence in the same orientation as the corresponding primer body region. The use of primers each containing a tag region having a nucleic acid sequence in the same orientation as the corresponding primer body region is effective for easy and low-cost synthesis. Even when the tag region and the primer body region are not directly linked to each other (e.g., when a non-natural compound such as azobenzene is inserted between the tag region and the primer body region), these regions preferably have sequences in the same orientation. The "nucleic acid sequence in same orientation" means that adjacent nucleotides are linked to each other via a phosphodiester bond between the 5' and 3' carbons, not between the 3' carbons or the 5' carbons, of the sugar moieties of the nucleotides. For example, in the case of a tag region where nucleotides are linked to one another via a phosphodiester bond between the 5' and 3' carbons of the sugar moieties, the nucleotides in the body region are also linked to one another between the 5' and 3' carbons of the sugar moieties.

The spacer region contains a spacer that inhibits an extension reaction catalyzed by polymerase, and the spacer can inhibit an extension reaction catalyzed by polymerase in the nucleic acid amplification reaction and maintain the single-stranded structure of the tag region. The structure of the spacer is not particularly limited, as long as the spacer can inhibit an extension reaction catalyzed by polymerase. The spacer preferably contains a nucleic acid derivative or a non-nucleic acid derivative.

The nucleic acid derivative is not particularly limited, provided that it can inhibit an extension reaction catalyzed by polymerase and maintain the single-stranded structure of the tag region. Examples of the nucleic acid derivatives include nucleic acids forming an inverted sequence structure, such as a 5'-5' linkage or a 3'-3' linkage, nucleic acids having a three-dimensional structure that inhibits the progress of polymerase, such as tight hairpin structures or pseudoknot structures, L-nucleic acids, 3-deoxy-2-hydroxy-dNs, nucleic acids containing modified bases, nucleic acids containing damaged bases, nucleic acids containing modified phosphate linkages, RNAs, 2'-OMe-Ns, BNAs (LNAs), and derivatives of these.

The terms "5'-5' linkage" and "3'-3' linkage" refer to a linkage between the 5' carbon of deoxyribose and the 5' carbon of the adjacent deoxyribose through a phosphate group, and a linkage between the 3' carbon of deoxyribose and the 3' carbon of the adjacent deoxyribose through a phosphate group, respectively, in a DNA as shown in the formula (1):

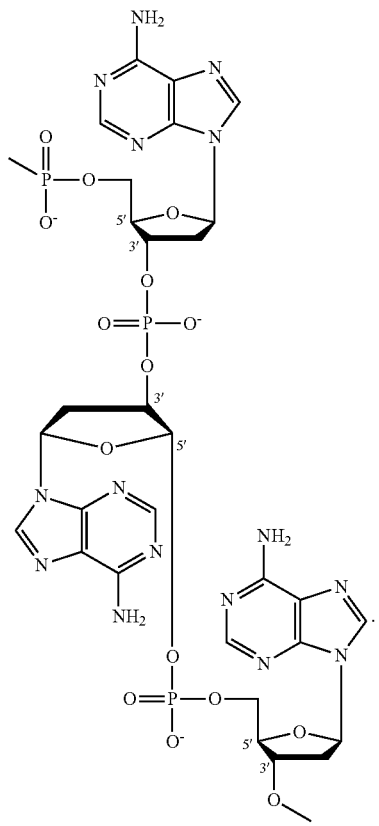

[Chem. 1]

These linkages are in an inverted orientation relative to the orientation of the normal 5'-3' linkage, and therefore are referred to as inverted sequence structures. Specific examples include a structure including two inverted structures so as to form a 5'-5' linkage between the 5' end of a primer body region and a spacer, and a 3'-3' linkage between the 3' end of a tag region and a spacer. The number of inverted structures is not particularly limited, as long as it is at least 1. The number is preferably even. When an even number of inverted structures are included, the tag region has a 5' free end as do normal primers. This makes it possible to in inhibit non-specific extension from the tag region and is also effective for detection. Moreover, when the spacer contains preferably 5 to 60 bases, unlike the single-base spacer as shown in the formula (1), it can serve as both a spacer and a tag.

The terms "hairpin structure" and "pseudoknot structure" refer to stable loop structures formed by pairing with another single-stranded region in the same molecule.

The term "L-nucleic acid" refers to L-DNA or L-RNA or a derivative thereof, in which the sugar of the nucleic acid, that is, deoxyribose or ribose is an optical isomer of the naturally-occurring D-form as shown in the formula (2):

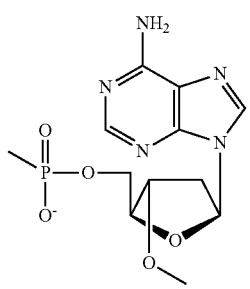

and the formula (3):

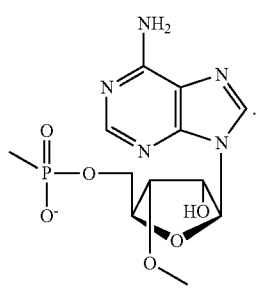

L-nucleic acids, which are not recognized by commonly used DNA polymerases, do not function as templates in extension reactions. L-DNA, which forms a left-handed double helix, will not hybridize to naturally-occurring D-nucleic acids but can hybridize only to nucleic acids of the same L-form.

3-Deoxy-2-hydroxy-dNs have a 2'-5' linkage between the 2' carbon of a deoxyribose that has no hydroxyl group at the 3' position and the 5' carbon of the adjacent deoxyribose as seen in a 3-deoxy-2-hydroxy-dA represented by the formula (4):

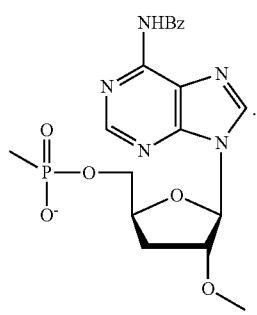

Thus, they are not recognized by DNA polymerases and do not function as templates in extension reactions. Preferably, in the present invention, the 3-deoxy-2-hydroxy-dN is linked to the primer via a 2'-5' linkage.

The term "nucleic acid containing a modified base" refers to a nucleic acid having a DNA base site modified with biotin, a chromophore, or the like. Examples of the chromophores include, but not limited to, pyrene, etheno, pyrrolo, perylene, fluorescein, FITC, Cy3, Cy5, TAMRA, Dabcyl, and cyanine chromophores. Examples of the nucleic acids containing a modified base include, but not limited to, amino C6-dA represented by the formula (5):

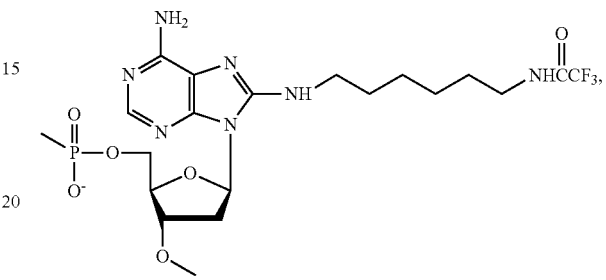

2-thio-dT represented by the formula (6):

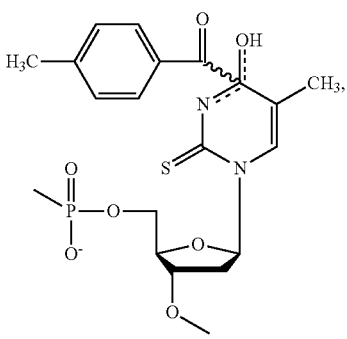

4-thio-dT represented by the formula (7):

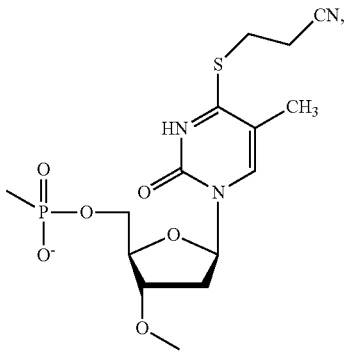

biotin-dT represented by the formula (8):
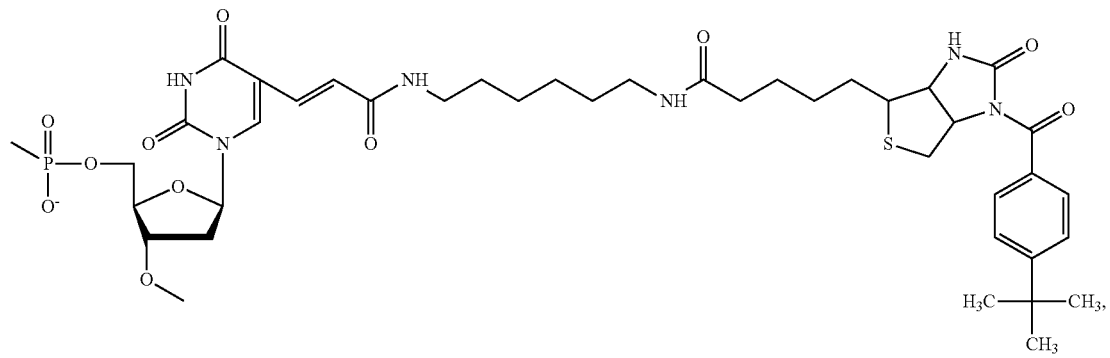 [SMILES: CO[C@@H]1C[C@H](n2cc(/C=C/C(=O)NCCCCCCNC(=O)CCCCC3SCC4C3NC(=O)N4C(=O)c3ccc(C(C)(C)C)cc3)c(=O)[nH]c2=O)O[C@@H]1COP(C)(=O)[O-]]
carboxy-dT represented by the formula (9):
[Chem. 9]
pyrene-dU represented by the formula (10):
[Chem. 10]
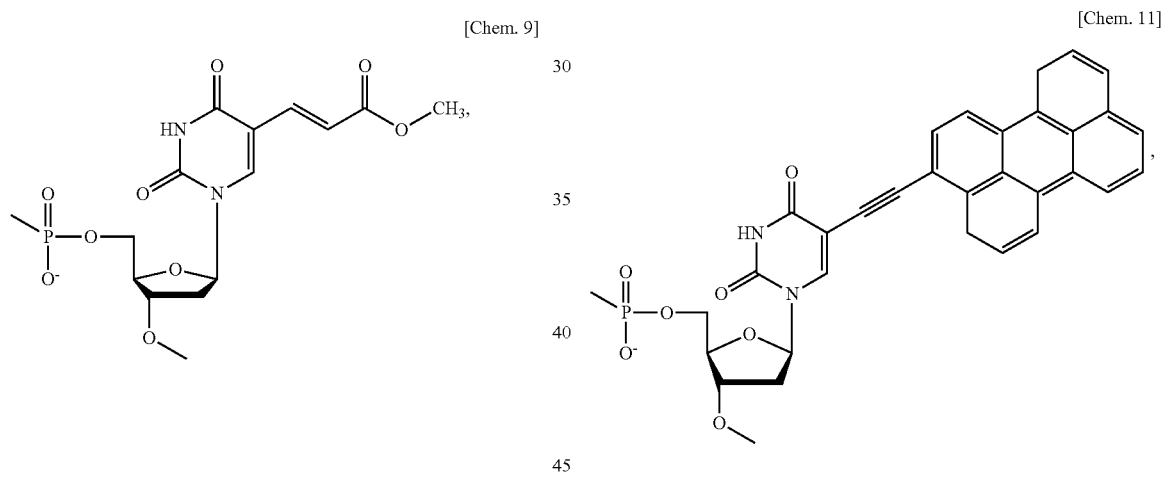
perylene-dU represented by the formula (11):
[Chem. 11]
pyrrolo-dC represented by the formula (12):
[Chem. 12]
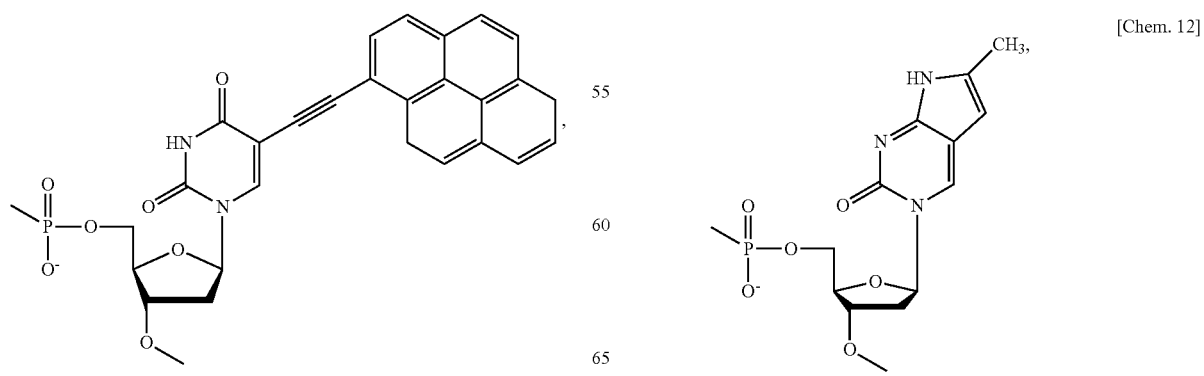

etheno-dA represented by the formula (13):
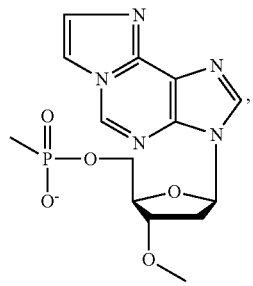
FITC-dT represented by the formula (14):
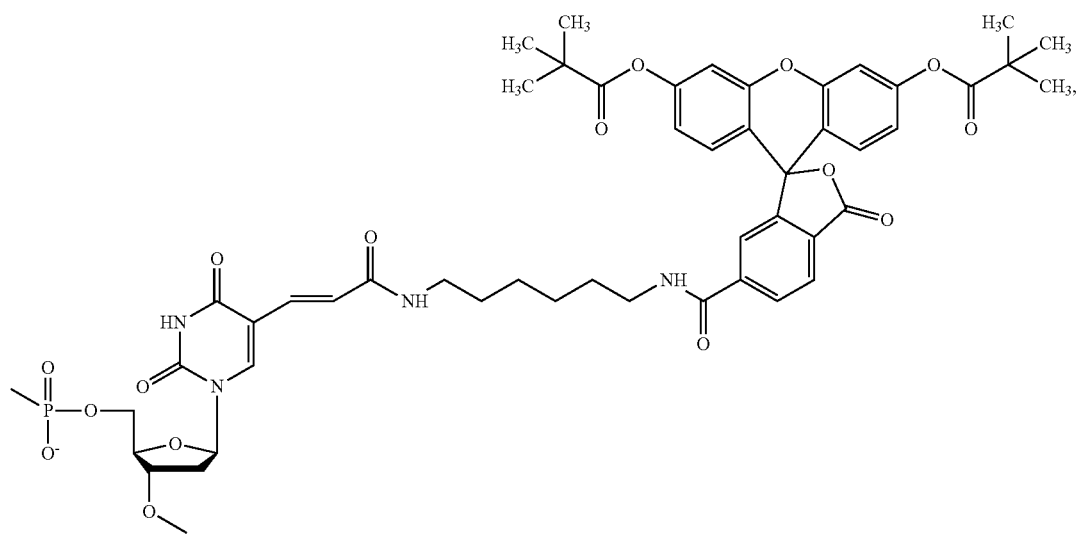
TAMRA-dT represented by the formula (15):
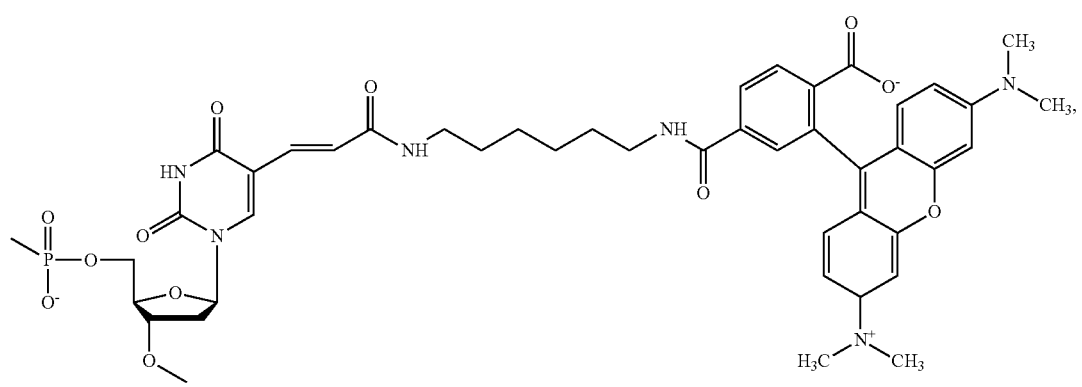

Dabcyl-dT represented by the formula (16):

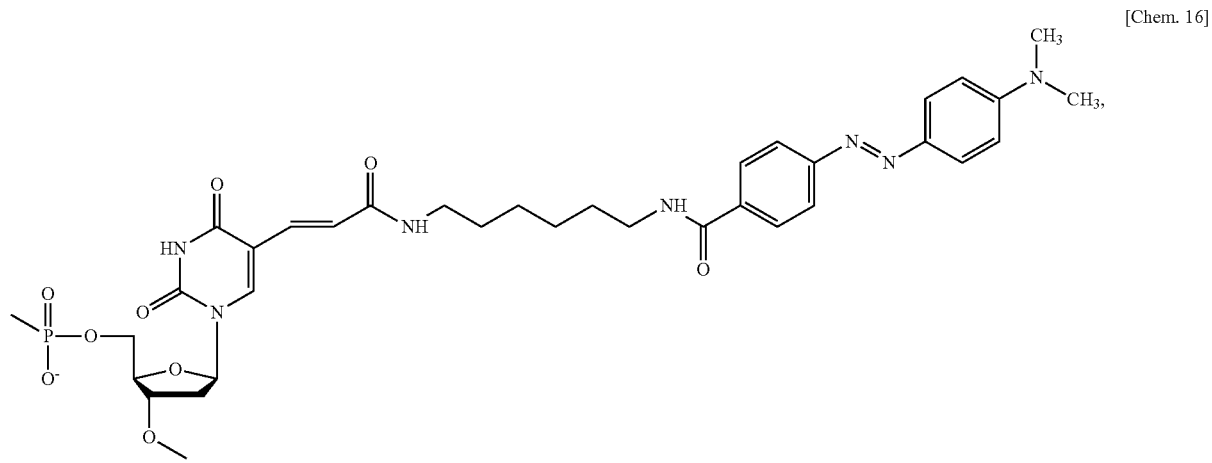

BHQ-1-dT, Cy3-dT, and Cy5-dT. These nucleic acids are not recognized by DNA polymerases because of the steric hindrance offered by the respective modifications in the base moiety, and thus do not function as templates in extension reactions.

The term "nucleic acid containing a damaged base" refers to an abasic nucleic acid or a nucleic acid containing a modified base, such as abasic nucleotides (AP site: apurinic base, apyrimidinic base), dSpacer as shown in the formula (17):

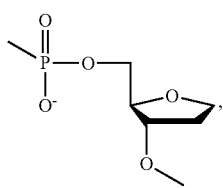

Abasic as shown in the formula (18):

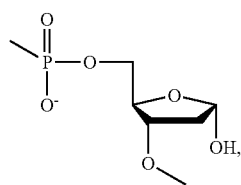

and 5-hydroxymethyl-dNs. These nucleic acids are not recognized by commonly used DNA polymerases, and thus do not function as templates in extension reactions.

The term "nucleic acid containing a modified phosphate linkage" refers to a nucleic acid whose phosphate groups are partially substituted with another atom or molecule, such as phosphorothioate (S-oligo) nucleic acids as represented by the formula (19):

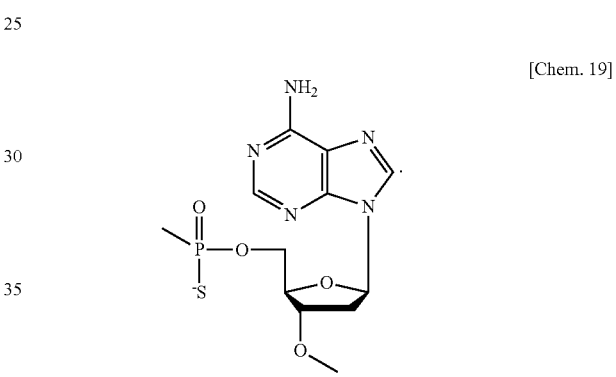

These nucleic acids do not function as templates in extension reactions because they are not recognized by DNA polymerases.

The term "RNA" refers to a nucleic acid whose sugar is ribose, as shown in the formula (20):

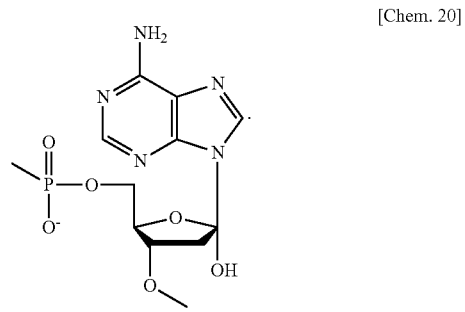

Such nucleic acids do not function as templates in extension reactions because they are not recognized by commonly used DNA polymerases.

The term "2'-OMe-N" refers to a nucleic acid whose sugar moiety is modified as seen in 2'-OMe-G represented by the formula (21):

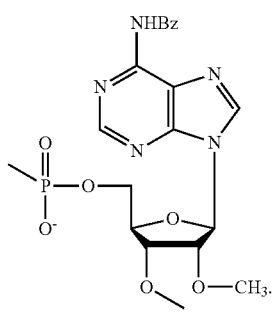

Such nucleic acids do not function as templates in extension reactions because they are not recognized by DNA polymerases.

As examples of non-nucleic acid derivatives that inhibit an extension reaction catalyzed by polymerase, there may be mentioned D-threoninol scaffolds, PCspacer, aliphatic chains such as a carbon chain ($C_a$), a PEG chain $(CH_2CH_2O)_n$, a disulfide-containing chain ($C_nSSC_n$), PNA, and derivatives of these. The non-nucleic acid derivative is not particularly limited as long as it can inhibit an extension reaction catalyzed by polymerase and maintain the single-stranded structure of the region. These non-nucleic acid molecules are not recognized by DNA polymerases because of their structures differing from nucleic acids, and thus do not function as templates in extension reactions.

The term "D-threoninol scaffold" refers to a structure linking nucleic acids via a threoninol bond as shown in the formula (22):

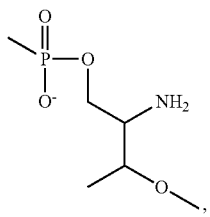

and various kinds of molecules can be inserted into the amino group of threoninol. Any molecule can be inserted as long as it can be coupled via an amino group. Examples of the molecules that may be inserted include chromophores such as pyrene, etheno, pyrrolo, perylene, fluorescein, FITC, TET, HEX, JOE, Cy3, Cy5, Dabcyl, cyanine, and BHQ chromophores, and biotin and EDTA, as well as azobenzene as shown in the formula (23):

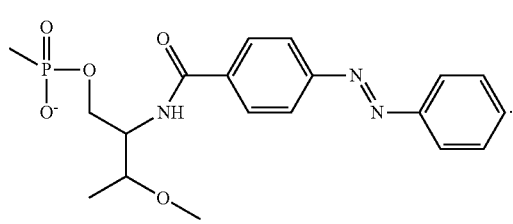

The term "aliphatic chain" refers to a continuous carbon chain represented by $C_n$, or a derivative thereof. The range of n is not particularly limited, and is preferably 1 to 45, and more preferably 2 to 18. Examples include C3 linker as shown in the formula (24):

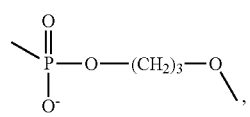

C6 linker, and C12 linker as shown in the formula (25):

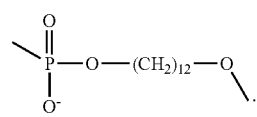

Examples of the derivatives also include PCspacer as shown in the formula (26):

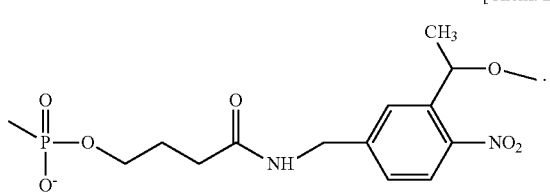

The term "PEG chain" refers to a structure in which polyethylene glycol units are linked as represented by $(CH_2CH_2O)_n$, or a derivative thereof. The range of n is not particularly limited, and is preferably 1 to 21, and more preferably 1 to 9. Examples include Spacer9 (triethyleneglycol spacer) as shown in the formula (27):

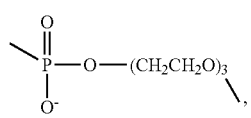

and Spacer18 (hexa-ethyleneglycol spacer) as shown in the formula (28):

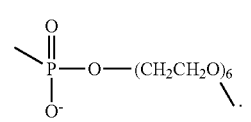

The term "disulfide-containing chain" refers to a structure containing a disulfide bond as represented by $C_nSSC_n$. The range of n is not particularly limited, and is preferably 1 to 20, and more preferably 1 to 12. Examples include a chain having three carbon atoms as shown in the formula (29):

[Chem. 29]

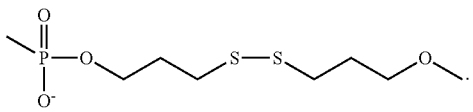

As long as the chain contains a disulfide bond, it may have an aliphatic chain, PEG chain or the like on each side of the disulfide bond. Other examples of the disulfide-containing chains include dithiol phosphoramidite as shown in the formula (30):

[Chem. 30]

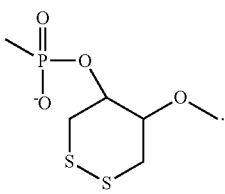

The term "PNA" refers to a molecule having a structure similar to DNA and RNA but having a peptide bond-containing backbone in which N-(2-aminoethyl)-glycine units are linked via an amide bond. Further, purine and pyrimidine rings, which correspond to nucleic acid bases, are linked to the backbone via a methylene group and a carbonyl group.

The term "BNA (LNA)" refers to a nucleic acid artificially synthesized by modifying the sugar moiety of DNA or RNA so as to form a bridge therewithin as shown in the formula (31):

[Chem. 31]

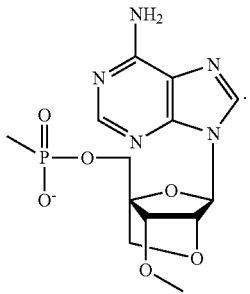

In the case of a tag region that consists only of natural nucleotides and has a nucleic acid sequence in the same orientation as the of the primer body region, a spacer that inhibits a polymerase reaction is usually necessary between the tag region and the primer region. On the other hand, in the case of a tag region that contains an L-nucleic acid, PNA, BNA, or the like and is incapable of functioning as a template in a reaction catalyzed by DNA polymerase and thus is not made double-stranded by a nucleic acid amplification reaction, the spacer that inhibits a polymerase reaction may be omitted. Moreover, the primers in the present invention may contain only one of the following: nucleic acid derivatives including stable loop structures (e.g. inverted structures, hairpin structures, pseudoknot structures), L-nucleic acids, 3-deoxy-2-hydroxy-dNs, nucleic acids containing a modified base, nucleic acids containing a damaged base, nucleic acids containing a modified phosphate linkage, RNAs, 2'-OMe-Ns, and BNAs (LNAs), and non-nucleic acid derivatives including carbon chains, PEG chains, disulfide-containing chains, and PNAs, and the like, or may contain two or more of these in combination.

The primers may be labeled with various molecules generally used for oligonucleotide labeling. Examples of such molecules include enzymes, magnetic particles, fluorescent pigments, and radioisotopes. These may be used alone, or two or more of these may be used in combination.

The primers thus designed may be prepared by any method, and known methods can be used. Specifically, the designed primers can be easily obtained with a DNA synthesizer or from a custom synthesis service.

The nucleic acid amplification method is not particularly limited, provided that it produces a nucleic acid having a single-stranded region at each end using the primers mentioned above. An example thereof is PCR. Alternatively, isothermal amplification techniques such as LAMP and ICAN may be used.

In the case where the nucleic acid amplification method is PCR using primers each linked to a tag region via a spacer, the pair of reverse and forward primers for the PCR reaction may be designed such that these two primers contain different spacers from each other, or such that one of them contains a spacer and the other incorporates no spacer but is modified with biotin or the like at the 5' end of the primer.

The PCR conditions are not particularly limited, provided that a target region of the above-described sample DNA is amplified by PCR using the sample DNA as a template and the primer set. The polymerase used in the PCR is not particularly limited, and is preferably a heat-stable DNA polymerase, and more preferably a heat-stable DNA polymerase that does not substantially have 3'-to-5' exonuclease activity. Examples of such heat-stable DNA polymerases include, but not limited to, Ex-Taq (Takara Bio, Inc.), KOD Plus (TOYOBO CO., LTD.), Phusion, PrimeSTAR, KOD FX, and Tks Gflex. Likewise, the PCR reaction conditions including temperature, time, and buffer composition are not particularly limited, and may be appropriately determined according to the DNA polymerase selected for use, the sequences of the primers, the length of the target sequence, and other factors. The length of the DNA to be amplified by the nucleic acid amplification reaction is preferably at least 20 bases, and more preferably at least 40 bases. If the length is less than 20 bases, the primers having sufficient specificity tend to be difficult to design, more likely resulting in non-specific amplification.

Figure 4:
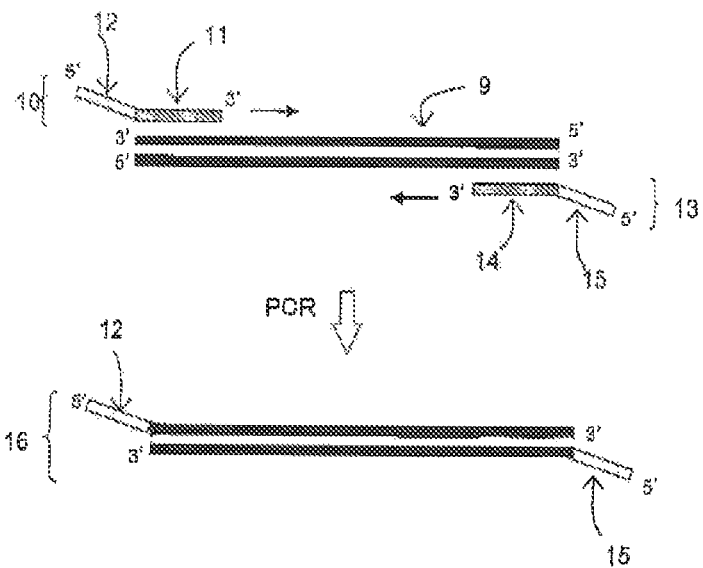
FIG. 4 is a schematic diagram illustrating the synthesis of a partially double-stranded nucleic acid in the present invention.

PCR can be carried out in a conventional manner using the primer set to provide an amplified product in which a single-stranded region is added to each end of the target nucleic acid sequence. FIG. 4 is a schematic diagram of an example of an amplification reaction using primers containing a primer body region and a tag region. The forward primer 10 contains a primer body region 11 having the same sequence as a 5' end portion of a target nucleic acid sequence 9, and a tag region 12 located towards the 5' end of the primer body region 11. The reverse primer 13 contains a primer body region 14 having a complementary sequence to a 3' end portion of the target nucleic acid sequence, and a tag region 15 located towards the 5' end of the primer body region 14. These two tag regions linked to the respective primers preferably have different sequences from each other. When PCR is performed with the primer set, the tag region added to each primer is not substantially involved in the PCR reaction, so that an amplified DNA product 16 having a single-stranded region at each end can be obtained. The amplified DNA fragment having a single-stranded region at each end refers to an amplified DNA product having a double-stranded DNA part that is the same as the target DNA region, and also having a single-stranded region as a 5' end tag part at each end of the double-stranded DNA part, as shown in FIG. 4. More specifically, the amplified DNA fragment is an amplified double-stranded DNA fragment having at each end thereof a single-stranded region that is formed of a non-modified nucleic acid, wherein the single-stranded regions at the respective ends have sequences in the same orientation as the respective adjacent DNA strands.

Figure 5:
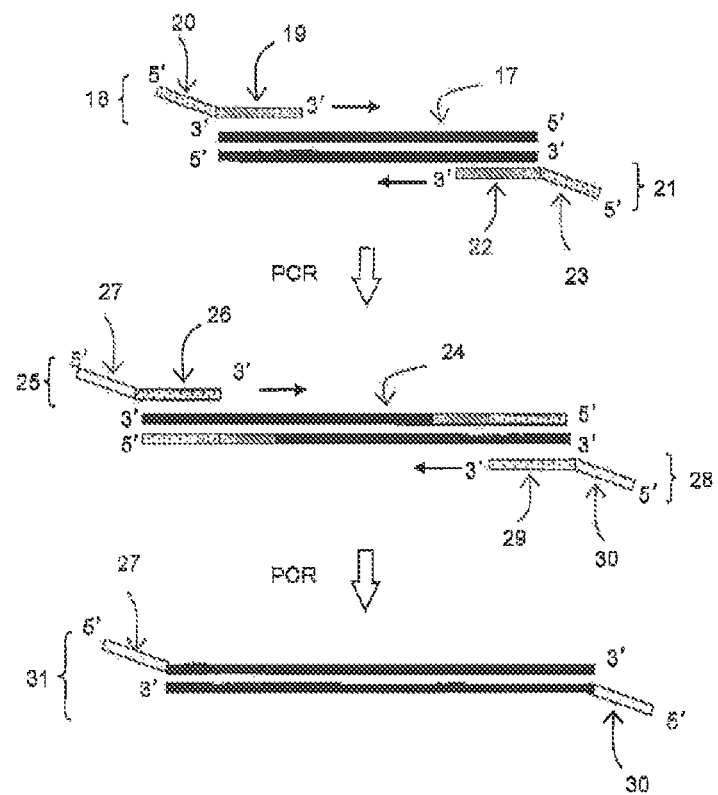
FIG. 5 is a schematic diagram illustrating another embodiment of the synthesis of a partially double-stranded nucleic acid in the present invention.

FIG. 5 is a schematic diagram of an example of an amplification reaction using a joint primer set including primers containing a primer body region and a common sequence region, and primers containing the common sequence region and a tag region. PCR can be carried out in a conventional manner using the first and second primer sets to provide an amplified product in which a single-stranded region is added to each end of a target nucleic acid sequence.

The first forward primer 18 contains a primer body region 19 having the same sequence as a 5' end portion of the target nucleic acid sequence 17, and a common sequence region 20 located towards the 5' end of the primer body region 19. The first reverse primer 21 contains a primer body region 22 having a complementary sequence to a 3' end portion of the target nucleic acid sequence, and a common sequence region 23 located towards the 5' end of the primer body region 22. These two common sequence regions added to the respective primers preferably have different sequences from each other. The PCR reaction using the first primer set produces an amplified double-stranded DNA product 24 containing the common regions.

Moreover, the second forward primer 25, which is shown around the common sequence region at either end of the amplified DNA product 24, contains a primer body region 26 having a sequence common to a 5' end portion of the amplified double-stranded DNA product 24 containing the common regions, and a tag region 27 located towards the 5' end of the primer body region 26. The second reverse primer 28 contains a primer body region 29 having a complementary sequence common to a 3' end portion of the amplified double-stranded DNA product 24 containing the common regions, and a tag region 30 located towards the 5' end of the primer body region 29. These two tag regions linked to the respective primers preferably have different sequences from each other. When PCR is performed with the primer set, the tag region added to each primer is not substantially involved in the PCR reaction, so that an amplified DNA product 31 having a single-stranded region at each end can be obtained. In this embodiment, the PCR reaction using the first primers and the PCR reaction using the second primers are sequentially carried out as shown in FIG. 5. With respect to the order, the first and second primers may be added at the same time or, alternatively, the second primers may be added later.

The amplified DNA fragment having a single-stranded region at each end refers to an amplified DNA product having a double-stranded DNA part that is the same as the target DNA region, and also having a single-stranded region as a 5' end tag part at each end of the double-stranded DNA part, as indicated by the reference 31 in FIG. 5.

In the case of using such first and second primer sets, a single set of second primers can be used for different target nucleic acids to provide the same single-stranded tag sequences, as long as these primer sets are designed to have the same common sequences. More specifically, the amplified DNA fragment is an amplified double-stranded DNA fragment having at each end thereof a single-stranded region that is formed of a non-modified nucleic acid, wherein the single-stranded regions at the respective ends have sequences in the same orientation as the respective adjacent DNA strands.

The single-stranded regions of the amplified product synthesized using the primers are used to form a hybridization complex. The term "hybridization" means that molecules containing nucleic acids complementarily form a complex (e.g. DNA/DNA, DNA/RNA, DNA/PNA, L-DNA/L-DNA). In the nucleic acid detection method of the present invention, the nucleic acid obtained after the nucleic acid amplification step can be used in a hybridization reaction without the need of any treatment for making the amplified product single-stranded (e.g. heat treatment) or other treatments because the nucleic acid contains the single-stranded regions.

The detection method allows a first oligonucleotide probe immobilized on a capture carrier (solid phase) to be hybridized with one of the single-stranded tag regions which contain natural nucleotides and are respectively located at the opposite ends of the amplified double-stranded DNA fragment. The detection method preferably further includes the step of hybridizing the other single-stranded region of the amplified double-stranded DNA fragment with a second oligonucleotide probe labeled directly or indirectly with a labeling substance. The formation of a ternary complex of the amplified double-stranded DNA fragment, the first oligonucleotide probe, and the second oligonucleotide probe is called "sandwich hybridization". The order of hybridization of the three molecules is not particularly limited.

The length of the first oligonucleotide probe is not particularly limited, as long as it is capable of hybridizing to one single-stranded region of the amplified double-stranded DNA fragment. The length is preferably 5 to 60 bases, and more preferably 10 to 40 bases.

The length of the second oligonucleotide probe is not particularly limited, as long as it is capable of hybridizing to the other single-stranded region of the amplified double-stranded DNA fragment. The length is preferably 5 to 60 bases, and more preferably 10 to 40 bases.

The labeling substance bound to the second oligonucleotide probe is not particularly limited, as long as it allows the amplified double-stranded DNA fragment to be detected. The labeling substance is preferably a colored carrier that allows the amplified double-stranded DNA fragment to be detected by visual observation. Examples of such colored carriers include colored particles and enzyme- or pigment-bound carriers. Preferred among these are colored particles.

Examples of the colored particles include colloidal particles of metals such as gold, silver, copper and platinum, colored latexes which are latexes colored with a pigment, a dye or the like, and silica nanoparticles which are silica (silicon dioxide) particles with pigment molecules immobilized therewithin. Preferred among these are colloidal gold particles and colored (e.g. blue, red) latex particles made of water-dispersible polymers. The use of such colored particles allows the amplified DNA fragment to be visually identified more easily. In particular, in the case of detecting multiple analytes at one time, differently colored particles are used for each analyte to allow the multiple analytes to be visually identified easily at one time.

In the case of using colored particles, the particle size is not particularly limited. Preferably, the particle size is determined such that the colored particles have less adverse effect on the formation of a sandwich hybridization complex and on the capturing of the target sequence-containing amplified product on the solid phase, and its color comes out very well in the detection. The particle size of colored particles is selected to be smaller than the pore size of a later-described chromatographic medium. Specifically, the particle size is typically not more than 500 nm, and in particular is preferably 0.1 nm to 100 nm, and more preferably 1 nm to 50 nm. The enzyme that may be used as the colored carrier refers to a protein that catalyzes a reaction of a substrate to develop a color or emit light. Examples include peroxidases, alkaline phosphatases, and luciferases. The enzyme is not limited to these examples, provided that it allows detection with the naked eye.

The conditions of the hybridization of the single-stranded region at either end of the amplified double-stranded DNA fragment and the first or second oligonucleotide probe are not particularly limited, provided that they can hybridize. Preferably, they are reacted at room temperature in 10 mM phosphate buffer. In this case, hybridization efficiency can be increased by adding a salt such as sodium chloride.

The presence of the target nucleic acid may be assessed by detecting the target substance in a sandwich hybridization complex formed in an identifiable zone on the capture carrier (solid phase). The detection is preferably determined by visual observation. Moreover, the detection is preferably accomplished under visible light. The term "visible light" refers to light particularly within the wavelength range of 380 to 800 nm. According to the detection method of the present invention, the amplified product obtained by the nucleic acid amplification reaction can be used directly in the hybridization reaction without the need of any treatment for making the amplified product single-stranded (e.g. heat denaturation). In addition, it is possible to simply and rapidly assess the presence of the target nucleic acid by visual observation without the need of special equipment.

The nucleic acid detection method involving the formation of a sandwich hybridization complex is preferably carried out on a nucleic acid detection device. The nucleic acid detection device is not particularly limited, and is preferably a device carrying a capture oligonucleotide probe having a sequence complementary to at least a part of the single-stranded tag region at the end of the amplified double-stranded DNA fragment. Examples include, but not limited to, chromatography devices, arrays, and beads.

Figure 6:
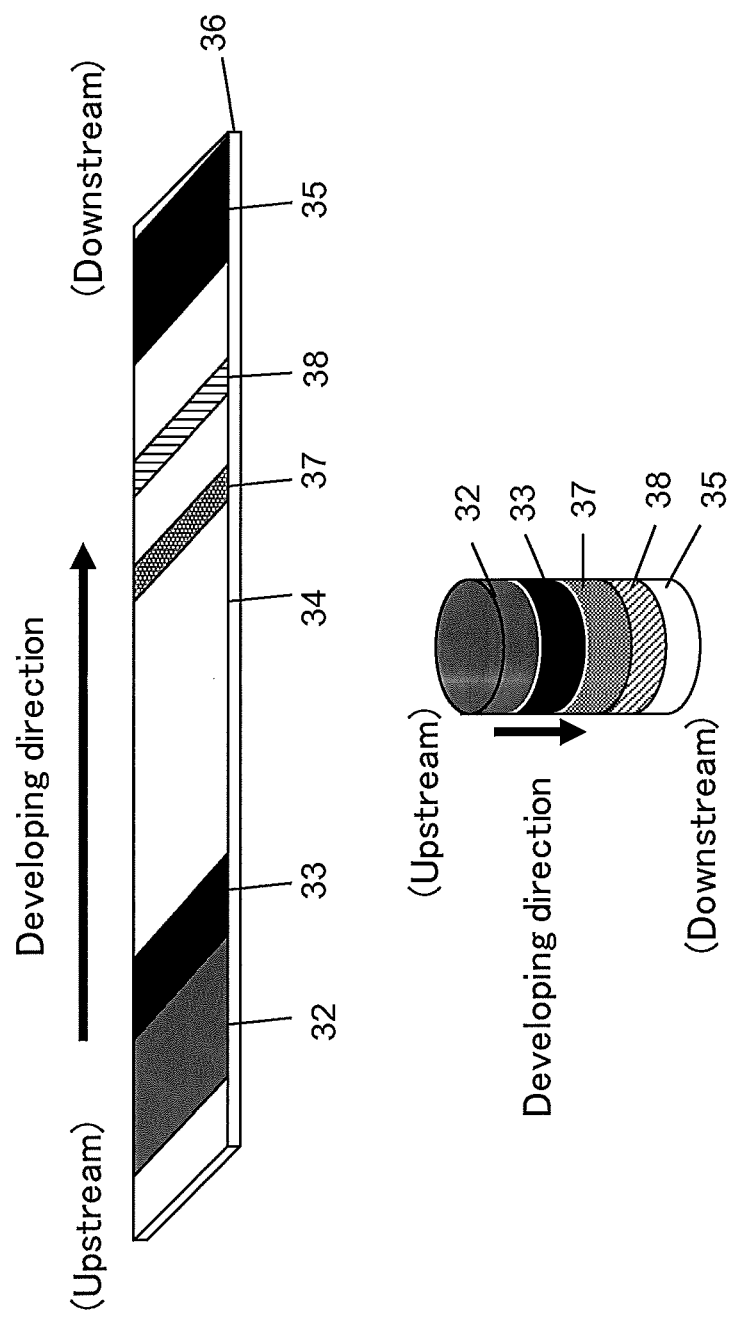
FIG. 6 is a schematic diagram of an example of a nucleic acid chromatography device of the present invention.

FIG. 6 shows a nucleic acid chromatography device that includes a sample pad 32 (a carrier to which an amplified DNA product is to be applied), a conjugate pad 33 (a carrier in which a colored carrier-bound oligonucleotide is placed), a carrier 34 carrying a capture oligonucleotide (a chromatographic medium), and an absorption pad 35, which members are attached onto a substrate member 36 with a pressure-sensitive adhesive or the like. The carrier 34 is provided with a test line 37 along which the capture oligonucleotide is applied, and a control line 38. In the case where the colored carrier-bound oligonucleotide is mixed with a developing solution, the conjugate pad 33 may not be used.

Preferably, chromatography is carried out by a method including the following steps (a) to (c) to detect an amplified double-stranded DNA fragment: (a) placing an amplified DNA fragment in a zone on the nucleic acid detection device which is different from a zone where the first oligonucleotide probe is immobilized; (b) diffusing the amplified DNA fragment on the device with a solvent towards the zone where the first oligonucleotide probe is immobilized; and (c) hybridizing the first oligonucleotide probe with the amplified DNA fragment in the zone where the first oligonucleotide probe is immobilized.

For example, in the nucleic acid chromatography device of FIG. 6, the amplified DNA fragment is placed on the sample pad 32 in the step (a). In the step (b), the amplified DNA fragment is diffused in the direction of the arrow. In the step (c), the amplified DNA fragment is hybridized with and captured by the first oligonucleotide probe immobilized on the test line 37.

Preferably, the detection method further includes the step of hybridizing the amplified DNA fragment with the second oligonucleotide probe labeled with a labeling substance before the step (c). For example, in the case of the nucleic acid chromatography device of FIG. 6, the amplified DNA fragment and the second oligonucleotide probe are hybridized on the conjugate pad 33.

Moreover, the chromatography is preferably carried out by the following steps (d) to (h): (d) placing the amplified DNA fragment and the second oligonucleotide probe labeled with a labeling substance, respectively, in discrete zones on the nucleic acid detection device which are different from the zone where the first oligonucleotide probe is immobilized; (e) diffusing the amplified DNA fragment with a solvent towards the zone where the second oligonucleotide probe labeled with a labeling substance is placed; (f) hybridizing the amplified DNA fragment with the second oligonucleotide probe labeled with a labeling substance in the zone where the second oligonucleotide probe labeled with a labeling substance is placed; (g) diffusing a hybridization complex obtained in the step (f) on a development medium towards the zone where the first oligonucleotide probe is placed; and (h) hybridizing the first oligonucleotide probe with the complex in the zone where the first oligonucleotide probe is immobilized.

For example, in the case of the nucleic acid chromatography device of FIG. 6, in the step (d), the amplified DNA fragment is placed on the sample pad 32, while the second oligonucleotide probe is placed on the conjugate pad 33. In the step (e), the amplified DNA fragment is diffused from the sample pad 32 in the direction of the arrow. In the step (f), the amplified DNA fragment and the second oligonucleotide probe are hybridized on the conjugate pad 33. In the step (g), the resulting hybridization complex of the amplified DNA fragment and the second oligonucleotide probe labeled with a labeling substance is diffused in the direction of the arrow. In the step (h), the first oligonucleotide probe and the complex are hybridized on the test line 37.

On the test line on the membrane, an oligonucleotide probe having a complementary sequence to one of the tag regions of the amplified DNA fragment is immobilized as the first capture oligonucleotide probe. The first capture oligonucleotide probe may be bound to the membrane directly or via a functional group or any substance. Examples of such mediating substances include, but are not limited to, peptides, proteins and nucleic acids. In the case where avidin is used as a mediating substance, the capture oligonucleotide should be modified with biotin.

On the control line on the membrane, an oligonucleotide probe for capturing a colored carrier is immobilized. The oligonucleotide probe for the control line has a complementary sequence to the second oligonucleotide probe labeled with a labeling substance so that it certainly captures the labeling substance when the sample solution is developed. The oligonucleotide probe for the control line may also be bound to the membrane directly or via a functional group or any substance as described above. Examples of mediating substances include, but are not limited to, peptides, proteins and nucleic acids. In the case where avidin is used as a mediating substance, the capture oligonucleotide should be modified with biotin.

The presence of the target nucleic acid in the sample can be assessed by visually observing a color on the test line. A color on the control line, on the other hand, can be visually observed to assess whether the development and the color reaction are normally carried out. The "visually observing" means observation with the naked eye to assess the color. The assessments are preferably accomplished under visible light. The term "visible light" refers to light particularly within the wavelength range of 380 to 800 nm.

Examples of the chromatographic media include paper filters such as qualitative filters, quantitative filters, phase separating filters, glass fiber filters, silica fiber filters, and bicomponent fiber filters. Other examples include filters made of celluloses (e.g. nitrocellulose), synthetic resin films such as polyethersulfone membranes, and porous gels such as silica gel, agarose, dextran, and gelatin. Nylon membranes can also be suitably used. In practical use, the form and size of the chromatographic medium are not particularly limited, and may be any suitable ones for operation and observation of the reaction results.

These carriers may be modified in various ways to improve hydrophilicity and affinity for compounds. In order to make the operation simpler, the back surface of the chromatographic medium whose opposite surface is provided with reaction sites is preferably provided with a supporting material made of plastic or the like.

The developing direction in the device is not particularly limited, and may be horizontal or vertical as shown in FIG. 6. The solvent used in the nucleic acid amplification reaction can serve as a developing solvent as well, and therefore the reaction solution obtained after the nucleic acid amplification reaction can be directly dropped to the sample pad 32 shown in FIG. 6. Alternatively, a separate developing solution may be added to the reaction solution obtained after the amplification reaction, followed by adding the mixture to the sample pad. Any developing solvent can be used, provided that it is liquid. Examples thereof include phosphate buffer and Good's buffers such as Tris buffer. Moreover, the solvent may contain a salt, surfactant, protein, or nucleic acid dissolved therein.

Figure 7:
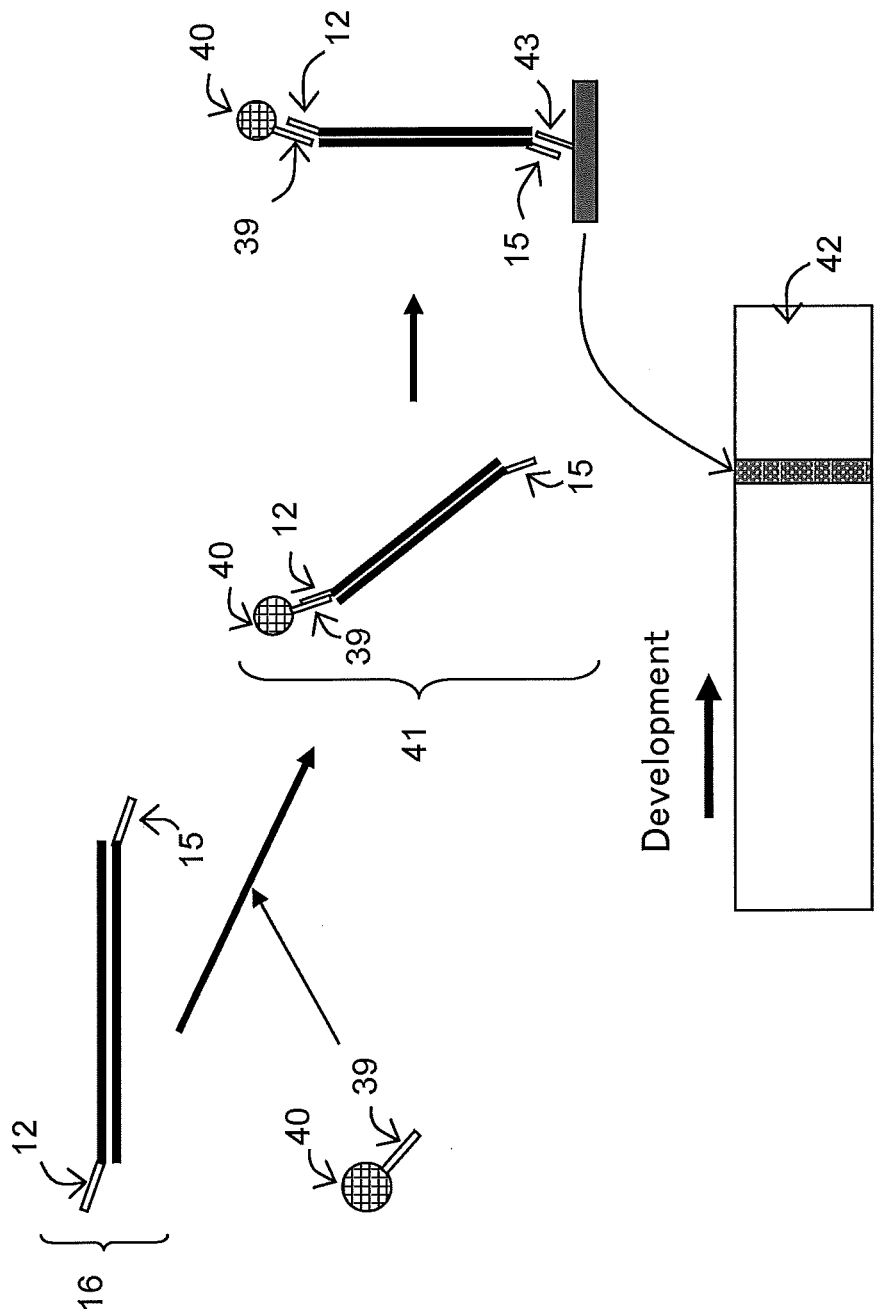
FIG. 7 is a schematic diagram of the principle of PCR product detection in the present invention.

With reference to FIG. 7, an exemplary embodiment of the present invention is described in which a sandwich hybridization complex is formed on a chromatographic carrier. An amplified DNA fragment 16 obtained in the nucleic acid amplification step is used in the subsequent complex formation step without performing any treatment for making the fragment single-stranded (e.g. heat treatment) or other treatments. The amplified DNA fragment 16 is hybridized with an oligonucleotide probe containing a colored carrier 40 and a nucleic acid sequence 39 capable of specifically binding to one tag region 12 of the DNA fragment, to form a first complex 41. The complex 41 may be formed prior to the application to the development medium, as formed for example in a PCR reaction vessel, or may be formed by applying the amplified DNA fragment to the carrier and allowing the amplified DNA fragment to move by capillary action to pass through the carrier that has been coated with the labeling molecule-bound oligonucleotide and dried.

The complex 41 comes, on the development medium, into contact with a capture oligonucleotide probe 43 that is already bound to an identifiable zone on a chromatographic medium 42 made of a porous membrane or the like. The capture oligonucleotide 43 has a sequence complementary to the other tag sequence 15 of the amplified DNA fragment, and thus hybridizes to the complex 41 to form a sandwich hybridization complex.

The order of procedures for forming such a sandwich hybridization complex is not particularly limited. Preferably, the amplified DNA fragment and the second oligonucleotide probe labeled with a labeling substance form a complex 41, and then the complex and the first capture oligonucleotide probe form a complex. Alternatively, a sandwich hybridization complex may be formed by enriching the amplified DNA fragment via the first capture oligonucleotide probe on the development medium, and then developing the second oligonucleotide labeled with a labeling substance.

Figure 8:
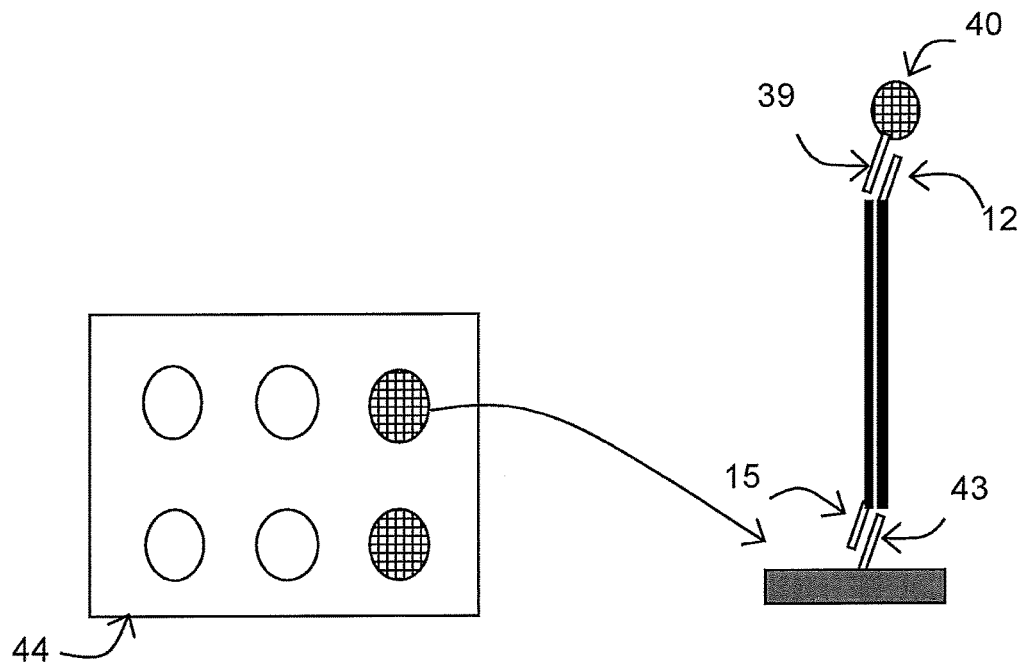
FIG. 8 is a schematic diagram of an example of a microarray (DNA chip) of the present invention.

Other embodiments of the nucleic acid detection device include arrays. Examples of such arrays include microarrays (DNA chips) as shown in FIG. 8. A ternary complex can be formed by sandwich hybridization in wells of the microarray 44 in which a capture oligonucleotide is immobilized.

Figure 9:
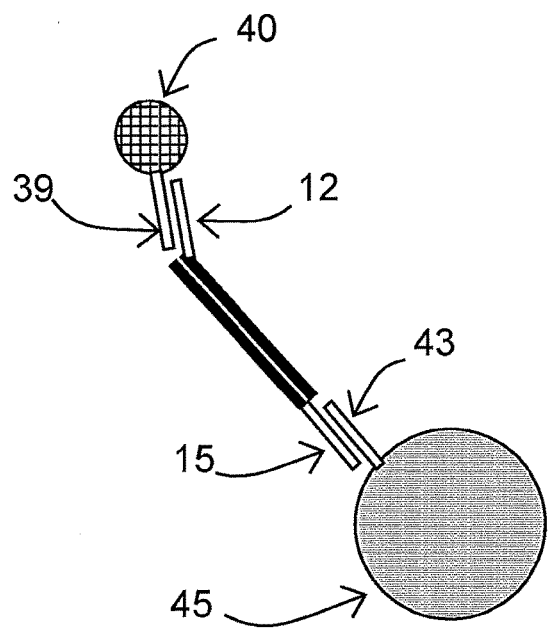
FIG. 9 is a schematic diagram of an example of a bead carrier of the present invention.

Alternatively, the device may be a bead form as shown in FIG. 9. A ternary complex can be formed by sandwich hybridization on the bead carrier 45 carrying a capture oligonucleotide.

The nucleic acid detection method and the nucleic acid detection device can be used in various technologies which involve detection of a nucleic acid (e.g. PCR product) obtained by a nucleic acid amplification method. Specifically, they can be used in, for example, molecular biology research, detection of pathogens, detection of contaminants such as allergens in foods, food quality control (inspection of mislabeled foods and genetically modified foods), livestock control, detection of mutations (e.g. single nucleotide polymorphisms (hereinafter also referred to as "SNPs"), insertions, deletions), detection of chromosomal deletion mutations, screening of diseases such as cancer, and so on. Accordingly, the present invention encompasses methods for detecting pathogenic infections, for detecting contaminants (e.g. allergens) in foods, for food quality control, for livestock control, and for detecting single nucleotide polymorphisms, and other methods which include the step of performing the nucleic acid detection method of the present invention.

As embodiments of application of the present invention, a pathogen detection method and an allergen detection method according to the present invention are described in detail below.

The pathogen detection method may be any method including the step of detecting a gene specific to a pathogen by the nucleic acid detection method of the present invention. The pathogen is not particularly limited, and specific examples include pathogenic bacteria, pathogenic viruses, food poisoning bacteria, and bacteria and viruses causing hospital infections. More specifically, there may be mentioned, for example, viruses such as hepatitis C virus (HCV), cytomegalovirus (CMV), Epstein-Barr virus (EBV), herpesviruses, and human immunodeficiency virus (HIV); bacteria such as *Escherichia coli* (e.g. O157), *Mycobacterium tuberculosis, Salmonella typhi*, salmonella bacteria, and *Vibrio parahaemolyticus*; and microorganisms such as *mycoplasma*.

More specifically, the pathogen detection method includes determining, by the nucleic acid detection method, whether a gene specific to a pathogen is present, for example, in a DNA sample prepared from a sample to be assessed for the presence of the pathogen. Alternatively, the sample to be assessed for the presence of the pathogen may be directly used for a template for nucleic acid amplification without preparing a DNA sample. For example, in the case where the pathogen to be detected is a bacterium such as *Escherichia coli*, a bacterial colony suspension can be used for a template. Then, if a gene specific to the pathogen is detected, the sample is determined to contain the pathogen. In this manner, it is possible to simply and highly accurately determine whether a sample contains a pathogen without the need of special equipment. Thus, the pathogen detection method according to the present invention can be used for the diagnosis of microbial infections.

The allergen detection method may be any method including the step of detecting a gene encoding an allergen by the nucleic acid detection method of the present invention. The allergen is not particularly limited, and specific examples include allergens contained in foods. More specifically, there may be mentioned, for example, egg albumen allergens, milk allergens, wheat allergens, buckwheat allergens, peanut allergens, and so on. More specifically, the allergen detection method includes determining, by the nucleic acid detection method, whether a gene encoding an allergen derived from egg, milk, wheat, buckwheat, peanut or the like is present, for example, in a DNA sample prepared from a food. Then, if such a gene is detected, the food is determined to contain an ingredient containing the allergen.

In this manner, it is possible to simply and highly accurately determine whether a sample prepared from a food or the like contains an allergen-containing ingredient without the need of special equipment. It should be noted that the allergen origin is not limited to those described above. For example, grains from which allergens may originate include any type of rice, corn, foxtail millet, proso millet, Japanese barnyard millet, buckwheat, or pulse. Since DNA is thermally stable, a trace amount of DNA can be detected even in processed foods. Thus, the allergen detection method provides data that can be used not only for food labeling and food allergen information but also for the detection of minute amounts of residual food additives (e.g. processing aids, carry-overs) and the detection of contaminants that are not intended by a manufacturer (e.g., the presence of cross-contamination between the manufacturing lines).

In addition to these applications, the nucleic acid detection method of the present invention is applicable to the determination of the parentage of a mammal including human, the identification of the pedigree of livestock, the identification of varieties of agricultural products, SNP detection, the detection of diseases (e.g. cancers) caused by gene mutations, and the like. More specifically, for example, in applications relating to livestock, the present invention can be used for pedigree registration, individual identification, parentage determination, removal of a carrier individual with a virulence gene, and the like. It should be noted that the present invention is not limited to the embodiments mentioned above and any modification may be made within the scope of the appended claims. Also, any appropriate combination of technical means disclosed in the different embodiments is included in the technical scope of the present invention.

EXAMPLES

The present invention is described in more detail below, referring to examples which are not to be construed as limiting the technical scope of the present invention.

Reference Example

Demonstration of Extension Inhibitory Effects of Various Spacers
(1) Synthesis of Various Primers In this reference example, a forward primer F and a reverse primer R were constructed to be able to amplify approximately 330 base pairs by PCR amplification using pUC19 (available from Takara Bio, Inc.) as a template.

Then, a tag sequence (Ta) and any of 31 types of spacers (Sx) were introduced to the 5' end of the primer F to construct tagged primers Ta-S1-F to Ta-S31-F.

The following forward primers free of spacers were constructed: a primer Ta-F only having the tag sequence (Ta) at the 5' end; a primer mTa-F modified with biotin at the 5' end; and a primer Ta-Fm modified with FITC at the 3' end. Table 1 shows the constructed forward primers.

TABLE 1

| Forward primer | Spacer (Sx) | Spacer structure | Addition of single-stranded tag to end (Reference Example) | Chromatographic detection (Example 1) | Array detection (Example 2) |
| --- | --- | --- | --- | --- | --- |
| Ta-F | — (D-DNA) | — | NO (Entirely double-stranded) | NO | NO |
| mTa-F | — (5'- Biotin) | — | NO (Entirely double-stranded) | NO | NO |
| Ta-Fm | — (3'-FITC) | — | NO (Not amplified) | NO | NO |
| Ta-S1-F | 5'-5' linkage + 3'-3' linkage | Formula (1) | YES | YES | YES |
| Ta-S2-F | L-DNA | Formula (2) | YES | YES | YES |
| Ta-S3-F | L-RNA | Formula (3) | YES | YES | YES |
| Ta-S4-F | 2'-5' linkage (3-deoxy-2-hydroxy-dA) | Formula (4) | YES | YES | YES |
| Ta-S5-F | Amino C6-dA | Formula (5) | YES | YES | YES |
| Ta-S6-F | 2-Thio-dT | Formula (6) | YES | YES | YES |
| Ta-S7-F | 4-Thio-dT | Formula (7) | YES | YES | YES |
| Ta-S8-F | Biotin-dT | Formula (8) | YES | YES | YES |
| Ta-S9-F | Carboxyl-dT | Formula (9) | YES | YES | YES |
| Ta-S10-F | Pyrene-dU | Formula (10) | YES | YES | YES |
| Ta-S11-F | Perylene-dU | Formula (11) | YES | YES | YES |
| Ta-S12-F | Pyrrolo-dC | Formula (12) | YES | YES | YES |
| Ta-S13-F | Etheno-dA | Formula (13) | YES | YES | YES |
| Ta-S14-F | FITC-dT | Formula (14) | YES | YES | YES |
| Ta-S15-F | TAMRA-dT | Formula (15) | YES | YES | YES |
| Ta-S16-F | Dabcyl-dT | Formula (16) | YES | YES | YES |
| Ta-S17-F | dSpacer | Formula (17) | YES | YES | YES |
| Ta-S18-F | Abasic | Formula (18) | YES | YES | YES |
| Ta-S19-F | Phosphorothioate | Formula (19) | YES | YES | YES |
| Ta-S20-F | RNA | Formula (20) | YES | YES | YES |

TABLE 1-continued

| Forward primer | Spacer (Sx) | Spacer structure | Addition of single-stranded tag to end (Reference Example) | Chromatographic detection (Example 1) | Array detection (Example 2) |
| --- | --- | --- | --- | --- | --- |
| Ta-S21-F | 2'-OMe-G | Formula (21) | YES | YES | YES |
| Ta-S22-F | D-threoninol | Formula (22) | YES | YES | YES |
| Ta-S23-F | D-threoninol + azobenzene | Formula (23) | YES | YES | YES |
| Ta-S24-F | C3 linker | Formula (24) | YES | YES | YES |
| Ta-S25-F | C12 linker | Formula (25) | YES | YES | YES |
| Ta-S26-F | PCspacer | Formula (26) | YES | YES | YES |
| Ta-S27-F | Spacer9 $(CH_2CH_2O)_3$ | Formula (27) | YES | YES | YES |
| Ta-S28-F | Spacer18 $(CH_2CH_2O)_6$ | Formula (28) | YES | YES | YES |
| Ta-S29-F | $C_3SSC_3$ | Formula (29) | YES | YES | YES |
| Ta-S30-F | Dithiol phosphoramidite (DTPA) | Formula (30) | YES | YES | YES |
| Ta-S31-F | BNA | Formula (31) | YES | YES | YES |

The structures of the spacers S1 to S31 in Table 1 correspond to those shown in the formulas (1) to (31), respectively. These tagged primers were purchased as products custom-synthesized by TSUKUBA OLIGO SERVICE CO., LTD. or by EUROGENTEC.

Forward primer F:
(SEQ ID NO: 1)
5'-$^D$d(GGAAACAGCTATGACCATGA)-3'

Reverse primer R:
(SEQ ID NO: 2)
5'-$^D$d(CTATGCGGCATCAGAGCAG)-3'

Tag sequence Ta:
(SEQ ID NO: 3)
5'-$^D$d(TGGCAACATTTTTCACTGGGTTTATAG)-3'

Primer Ta-Sx-F:
(SEQ ID NO: 4)
5'-$^D$d(TGGCAACATTTTTCACTGGGTTTATAG Sx

GGAAACAGCTATGACCATGA)-3'

Primer Ta-F:
(SEQ ID NO: 5)
5'-$^D$d(TGGCAACATTTTTCACTGGGTTTATAGGGAAACAGCTATGACCA

TGA)-3'

Primer mTa-F:
(SEQ ID NO: 6)
5'-Biotin-$^D$d(TGGCAACATTTTTCACTGGGTTTATAGGGAAACAGCT

ATGACCATGA)-3'

Primer Ta-Fm:
(SEQ ID NO: 7)
5'-$^D$d(TGGCAACATTTTTCACTGGGTTTATAGGGAAACAGCTATGACCA

TGA)-FITC-3'

(2) PCR Using Various Primer Sets

PCR was performed using the primers prepared in the above step (1). Specifically, 100 µl PCR mixtures were prepared by adding any of the forward primers Ta-S1-F to Ta-S31-F, Ta-F, mTa-F, and Ta-Fm (20 pmol), the reverse primer R (20 pmol) and pUC19 (10 pg) to 0.2-ml PCR tubes, and following the instruction manual of a PCR kit ExTaq (available from Takara Bio, Inc.). Thereafter, the tubes were set in a thermal cycler (GeneAmp PCR System, available from Applied Biosystems), and subjected to heat treatment at 95° C. for five minutes and then exposed to 35 cycles of 95° C. for 30 seconds, 55° C. for 30 seconds, and 72° C. for 30 seconds. In this manner, target nucleic acids of approximately 330 bp were amplified.

(3) Agarose Gel Electrophoresis

A 2% agarose gel was prepared from 1×TAE buffer (available from NIPPON GENE CO., LTD.) and agarose (available from Wako Pure Chemical Industries, Ltd.). The gel was placed in an electrophoresis chamber, and the chamber was filled with 1×TAE buffer. Subsequently, each of the PCR mixtures prepared in the step (2) (5 µl) was combined with a loading buffer (1 µl) and then applied to wells of the gel. A voltage of 100 V was applied to cause migration for 30 minutes, and the gel was then immersed and stained in an ethidium bromide solution (available from NACALAI TESQUE, INC.) for 15 minutes. After staining, a UV photography device was used to confirm the presence of amplified double-stranded DNA products by UV radiation at 254 nm.

This confirmed the presence of a single band of amplified product for each pair, but no amplified product was confirmed for the reaction using the forward primer Ta-Fm that was modified at the 3' end and was free of spacers.

(4) Modified Polyacrylamide Gel Electrophoresis (Denaturing PAGE)

The PCR mixtures prepared in the step (2) (7 µl each) were sampled in PCR tubes, and each combined with TBE-Urea sample buffer (available from Invitrogen) (7 µl). The mixtures were then heated at 70° C. for 3 minutes. In an electrophoresis chamber, 6% TBE-Urea Gel (available from Invitrogen) was set, and TBE buffer (1.08% (w/v) Tris, 0.55% (w/v) boric acid, 0.037% (w/v) EDTA2Na ($2H_2O$)) was then charged. The heat-treated amplified products were applied to wells.

Figure 10:
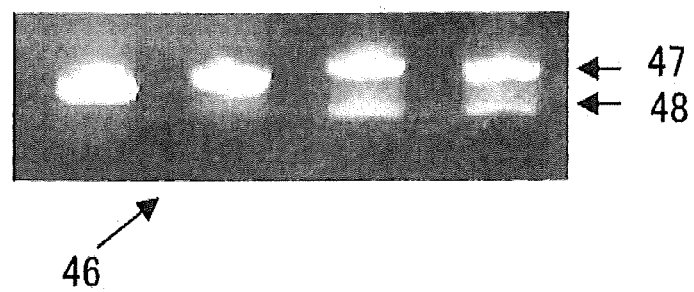
FIG. 10 shows an example of the results of denaturing PAGE in Reference Example.

Electrophoresis was carried out by applying 180 V for 60 minutes, and then the gel was immersed and stained in an ethidium bromide solution (available from NACALAI TESQUE, INC.) for 15 minutes. After staining, a UV photography device was used to confirm the presence of amplified products in a denatured single-stranded form by UV radiation at 254 nm. FIG. 10 shows, as typical examples, the results of electrophoresis of the PCR amplified products using (i) the primer Ta-F, (ii) the primer Ta-S1-F, (iii) the primer Ta-S20-F, and (iv) the primer Ta-S23-F as the forward primer.

The electrophoresis of the PCR amplified products by denaturing PAGE confirmed the presence of a single band for the PCR amplified products prepared using the forward primers free of spacers and two bands for the PCR amplified products prepared using the forward primers containing spacers.

The PCR amplified products for which a single band was confirmed by both agarose gel electrophoresis and denaturing PAGE were amplified products that were double-stranded entirely from one end to the other. The PCR products for which a single band was confirmed by agarose gel electrophoresis and two bands were confirmed by denaturing PAGE were determined to form a double strand consisting of single-stranded DNAs of different lengths associated with each other, and thus to be amplified double-stranded products having a single-stranded tag at the end as a result of the spacers inhibiting an extension reaction catalyzed by polymerase.

Table 1 shows the results of PCR using the forward primers containing spacers.

Example 1

Detection by Chromatography Using Various Spacer-Added Primer Sets (1) PCR Using Various Primer Sets PCR was performed in the same manner as in the step (1) of Reference Example, except that the reverse primer used was Tm-S1-R. Thus, target amplified products of 330 bp were amplified.

```
Tag sequence Tm:
                                         (SEQ ID NO: 8)
5'-Dd(GGTTAGCTTCCAACCACGTGTAGATCA)-3'

Primer Tm-S1-R:
                                         (SEQ ID NO: 9)
5'-Dd(GGTTAGCTTCCAACCACGTGTAGATCA S1
CTATGCGGCATCAGAGCAG)-3'
```

(2) Preparation of Gold Colloid-Bound Oligonucleotide Probe

Gold Colloid (40 nm, 9.0×10¹⁰ (particles/ml), available from British BioCell International) and a thiol group-containing oligonucleotide probe (SEQ ID NO:5, a strand complementary to the tag sequence Ta (SEQ ID NO:3)) were mixed and then incubated at 50° C. for 16 hours. The resulting mixture was centrifuged at 6000 rpm for 15 minutes, and the supernatant was removed. The residue was combined and mixed with 5 mM phosphate buffer (pH 7) containing 0.05 M sodium chloride, and then incubated again at 50° C. for 40 hours.

After incubation, the resulting mixture was centrifuged (6000 rpm, 15 minutes). The supernatant was removed, and the residue was combined with 5 mM phosphate buffer (pH 7). This buffer replacement procedure was performed again. The gold colloid solution thus prepared was uniformly applied to a glass fiber pad and dried in a vacuum oven. In this manner, a conjugate pad was prepared.

```
Oligonucleotide probe 1:
                                         (SEQ ID NO: 10)
5'-Dd(CTATAAACCCAGTGAAAAATGTTGCCA)-SH-3'
```

(3) Immobilization of Oligonucleotide Probe on Solid Phase

A 3'-biotin-modified oligonucleotide probe having a sequence (SEQ ID NO:11) complementary to SEQ ID NO:8 was mixed with streptavidin. The mixture was applied along a line on a nitrocellulose membrane (product name: Hi-Flow 180, available from Millipore) with a dispenser, and air-dried at 40° C. for 30 minutes.

```
Oligonucleotide probe 2:
                                         (SEQ ID NO: 11)
5'-Dd(GATCATACACGTGGTTGGAAGCTAACC)-Biotin-3'
```

(4) Preparation of Nucleic Acid Chromatography-Like Test Strip

A test strip to be used for the detection of the PCR products amplified using the tagged primer sets was prepared by attaching a chromatographic medium consisting of the nitrocellulose membrane prepared above, the conjugate pad prepared above, a general sample pad as a sample application zone, and an absorption pad for absorbing a developed sample and a labeling substance to a substrate consisting of a backing sheet as shown in FIG. 6.

(5) Detection of PCR Products Using Test Strip

The PCR products obtained in the step (1) were immediately applied, without being denatured, to the sample application zone on the test strip prepared in the step (4) to perform detection by chromatography. The detection by chromatography took a short time (5 to 15 minutes).

Figure 11:
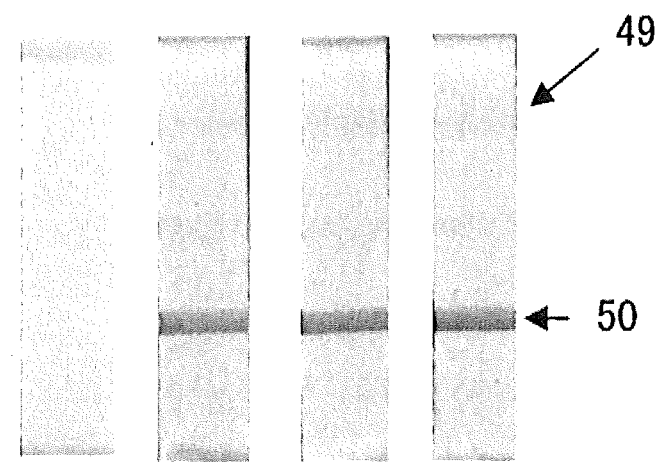
FIG. 11 shows examples of the results of the detection of PCR amplified products by a nucleic acid chromatography-like strip of Example 1.

Table 1 shows the results. In Table 1, "YES" was given to primers that resulted in the detection of a colored line specific to the target nucleic acid on the test strip when it was used in PCR with pUC19 as an analyte in the step (1) and resulted in the detection of no colored line when it was used with water as a negative control. FIG. 11 shows, as typical examples, the results of the chromatography-like test strip-based detection of the PCR products amplified using (i) the primer Ta-F, (ii) the primer Ta-S1-F, (iii) the primer Ta-S20-F, and (iv) the primer Ta-S23-F as the forward primer.

Example 2

Detection with Array Using Various Spacer-Added Primer Sets (1) Immobilization of Oligonucleotide Probe on Solid Phase A 3'-biotin-modified oligonucleotide probe having a sequence (SEQ ID NO:11) complementary to SEQ ID NO:8 was mixed with streptavidin. A 1 μl portion of the mixture was spotted on a nitrocellulose membrane (product name: Hi-Flow 180, available from Millipore), and air-dried at 40° C. for 30 minutes. This probe-immobilized membrane was used as an array to detect the PCR products amplified using the various tagged primer sets.

(2) Detection of PCR Products by Dot Blotting

Each of the PCR products obtained in the step (1) of Example 1 was immediately applied, without being denatured, to the array prepared in the step (1), and the gold colloidal solution prepared in the step (2) of Example 1 was then added dropwise, followed by leaving the mixture standing for 15 to 20 minutes to perform detection with the array. The detection by dot blotting using the array took a short time (15 to 20 minutes).

Table 1 shows the results. In Table 1, "YES" was given to primers that resulted in the detection of a colored spot specific to the target nucleic acid on the array when it was used with the analyte pUC19, and resulted in the detection of no colored spot when it was used with water as a negative control.

Example 3

Experiment Using Various PCR Kits

The same experiments as in Reference Example and Examples 1 and 2 were performed using PCR kits other than EX Taq, including KOD plus, Phusion, PrimeSTAR, KOD FX, and Tks Gflex, as a result of which the same results as when EX Taq PCR was used were demonstrated.

Example 4

(1) Synthesis of L-DNA-Tagged Primers

In this example, a forward primer (F) and a reverse primer (R) were constructed in the same manner as in Reference Example to be able to amplify approximately 330 base pairs by PCR amplification using pUC19 (available from Takara Bio, Inc.) as a template. Then, tag sequences T1 and T2 including non-natural (L-) DNA strands were respectively introduced to the 5' ends of these primers to construct L-DNA-tagged primers T1-F and T2-R. The synthesis of these L-DNA-tagged primers was accomplished by a general phosphoramidite method using a DNA automatic synthesizer (H-8-SE: Gene World) with a 0.2 µM column.

The following shows the primer set prepared in this study.

```
Tag sequence T1:
                                            (SEQ ID NO: 12)
5'-Ld(GACAACGGAGACAGAGCCAA)-3'

Tag sequence T2:
                                            (SEQ ID NO: 13)
5'-Ld(ATGCTACCGTATGCCCAGTG)-3'

Primer T1-F:
                                            (SEQ ID NO: 14)
5'-Ld(GACAACGGAGACAGAGCCAA)-

Dd(GGAAACAGCTATGACCATGA)-3'

Primer T2-R:
                                            (SEQ ID NO: 15)
5'-Ld(ATGCTACCGTATGCCCAGTG)-

Dd(CTATGCGGCATCAGAGCAG)-3'
```

(2) PCR Using L-DNA-Tagged Primer Set

PCR was performed using the primer set prepared in the above step (1). Specifically, a 100 µl PCR mixture was prepared by adding the primer T1-F and the primer T2-R (15 pmol each) and pUC19 (10 ng) to a 0.2-ml PCR tube, and following the instruction manual of a PCR device ExTaq (available from Takara Bio, Inc.). Thereafter, the tube was set in a thermal cycler (GeneAmp PCR System, available from Applied Biosystems), and subjected to heat treatment at 95° C. for five minutes and then exposed to 35 cycles of 95° C. for 30 seconds, 55° C. for 30 seconds, and 72° C. for 30 seconds. In this manner, a target product of approximately 330 bp was amplified. Separately, the same reaction procedure was carried out but in the absence of pUC19 as a negative control.

(3) Preparation of Latex-Bound L-Oligonucleotide Probe

A carboxyl group-containing polystyrene latex (solids content: 10% (w/w), available from Bangs Laboratories, Inc.) and an amino group-containing L-oligonucleotide probe (SEQ ID NO:16, a strand complementary to SEQ ID NO:12) were bonded by mixing them in MES buffer containing a necessary amount of a water-soluble carbodiimide, and the resulting product was blocked with monoethanolamine. The reaction solution was centrifuged, and the supernatant was then removed. The precipitate thus obtained was washed with water. After washing, the precipitate was resuspended in HEPES buffer containing a surfactant. The suspension was uniformly applied to a glass fiber pad, and dried in a vacuum oven. In this manner, a conjugate pad was prepared.

```
Nucleotide probe 3:
                                            (SEQ ID NO: 16)
5'-Ld(TTGGCTCTGTCTCCGTTGTC)-NH2-3'
```

(4) Immobilization of L-Oligonucleotide Probe on Solid Phase

A carboxyl group-modified nylon membrane (available from Pall Corporation, 6 mm×60 mm) was treated with a water-soluble carbodiimide, and washed with deionized water. An amino group-containing L-oligonucleotide probe having a sequence (SEQ ID NO:17) complementary to SEQ ID NO:13 was applied to the activated membrane with a dispenser along a line drawn 30 mm from one end of the membrane, and then air-dried for 15 minutes. Subsequently, the membrane was treated with Tris buffer and blocked, and then washed with water and dried.

```
Nucleotide probe 4:
                                            (SEQ ID NO: 17)
5'-Ld(CACTGGGCATACGGTAGCAT)-NH2-3'
```

(5) Preparation of Nucleic Acid Chromatography-Like Test Strip

A test strip to be used for the detection of the PCR product amplified using the L-DNA-tagged primer set was prepared by attaching a chromatographic medium consisting of the nylon membrane prepared above, the conjugate pad prepared above, a general sample pad as a sample application zone, and an absorption pad for absorbing a developed sample and a labeling substance to a substrate consisting of a backing sheet as shown in FIG. 6.

(6) Detection of PCR Product Using Test Strip

The PCR product obtained in the step (2) was immediately applied, without being denatured, to the sample application zone on the test strip prepared in the step (5) to perform detection by chromatography. A colored line specific to the target nucleic acid was detected along the test line for the sample prepared using pUC19 as an analyte in the step (2). In contrast, there was no line detected for the negative control prepared using water instead. The detection by chromatography took a short time (10 to 15 minutes).

Example 5

(1) Synthesis of Hairpin-Tagged Primers

In the same manner as in the step (1) of Reference Example, a forward primer (F) and a reverse primer (R) were constructed to be able to amplify approximately 330 base pairs by PCR amplification using pUC19 (available from Takara Bio, Inc.) as a template. Then, a polymerase reaction inhibitory region (H) having a hairpin structure and a tag sequence T3 or T4 were introduced to the 5' end of each primer to synthesize tagged primers T3-H-F and T4-H-R.

The following shows the primer set prepared in this study. Polymerase reaction inhibitory sequence H:

```
                                            (SEQ ID NO: 18)
5'-Dd(AGGCGAGGTCGCGAGCGCACATGTGCGCTCGCGACCTCGCC

T)-3'

Tag sequence T3:
                                            (SEQ ID NO: 19)
5'-Dd(TATGATATGCTTCTCCACGCATAAT)-3'
```

-continued

```
Tag sequence T4:
                                          (SEQ ID NO: 20)
5'-Dd(TGCTCTGTACACTTGCTCAAT)-3'

Primer T3-H-F:
                                          (SEQ ID NO: 21)
5'-Dd(TATGATATGCTTCTCCACGCATAATAGGCGAGGTCGCGAGCGCA

CATGTGCGCTCGCGACCTCGCCTGGAAACAGCTATGACCATGA)-3'

Primer T4-H-R:
                                          (SEQ ID NO: 22)
5'-Dd(TGCTCTGTACACTTGCTCAATAGGCGAGGTCGCGAGCGCACATG

TGCGCTCGCGACCTCGCCTCTATGCGGCATCAGAGCAG)-3'
```

(2) PCR Using Hairpin-Tagged Primer Set

PCR was performed using the primer set prepared in the above step (1). Specifically, a 100 µl PCR mixture was prepared by adding the primer F and the primer R (15 pmol each), and pUC19 (10 ng) to a 0.2-ml PCR tube, and following the instruction manual of a PCR device ExTaq (available from Takara Bio, Inc.). Thereafter, the tube was set in a thermal cycler (GeneAmp PCR System, available from Applied Biosystems), and subjected to heat treatment at 95° C. for five minutes and then exposed to 35 cycles of 95° C. for 30 seconds, 55° C. for 30 seconds, and 72° C. for 30 seconds. In this manner, a target product of approximately 330 bp was amplified. Separately, the same reaction procedure was carried out but in the absence of pUC19 as a negative control.

(3) Preparation of Latex-Bound Oligonucleotide Probe

A carboxyl group-containing polystyrene latex (solids content: 10% (w/w), available from Bangs Laboratories, Inc.) and an amino group-containing oligonucleotide probe (SEQ ID NO:23), a strand complementary to SEQ ID NO:19) were bonded by mixing them in MES buffer containing a necessary amount of a water-soluble carbodiimide, and the resulting product was blocked with monoethanolamine. The reaction solution was centrifuged, and the supernatant was then removed. The precipitate thus obtained was washed with water. After washing, the precipitate was resuspended in HEPES buffer containing a surfactant. The suspension was uniformly applied to a glass fiber pad, and dried in a vacuum oven. In this manner, a conjugate pad was prepared.

```
Oligonucleotide probe 5:
                                          (SEQ ID NO: 23)
5'-Dd(ATTATGCGTGGAGAAGCATATCATA)-NH2-3'
```

(4) Immobilization of Oligonucleotide Probe on Solid Phase

A carboxyl group-modified nylon membrane (available from Pall Corporation, 6 mm×60 mm) was treated with a water-soluble carbodiimide, and washed with deionized water. An amino group-containing L-oligonucleotide probe having a sequence (SEQ ID NO:24) complementary to SEQ ID NO:20 was applied to the activated membrane with a dispenser along a line drawn 30 mm from one end of the membrane, and then air-dried for 15 minutes. Subsequently, the membrane was treated with Tris buffer and blocked, and then washed with water and dried.

```
Oligonucleotide probe 6:
                                          (SEQ ID NO: 24)
5'-Dd(ATTGAGCAAGTGTACAGAGCA)-NH2-3'
```

(5) Preparation of Nucleic Acid Chromatography-Like Test Strip

A test strip to be used for the detection of the PCR product amplified using the hairpin-tagged primer set was prepared by attaching a chromatographic medium consisting of the nylon membrane prepared above, the conjugate pad prepared above, a general sample pad as a sample application zone, and an absorption pad for absorbing a developed sample and a labeling substance to a substrate consisting of a backing sheet as shown in FIG. 6.

(6) Detection of PCR Product Using Test Strip

The PCR product obtained in the step (2) was immediately applied, without being denatured, to the sample application zone on the test strip prepared in the step (5) to perform detection by chromatography. A colored line specific to the target nucleic acid was detected along the test line for the sample prepared using pUC19 as an analyte in the step (2). In contrast, there was no line detected for the negative control prepared using water instead. The detection by chromatography took a short time (10 to 15 minutes).

Example 6

(1) Synthesis of Artificial Nucleic Acid (Azobenzene)-Inserted Primers

In the same manner as in the step (1) of Reference Example, a forward primer (F) and a reverse primer (R) were constructed to be able to amplify approximately 330 base pairs by PCR amplification using pUC19 (available from Takara Bio, Inc.) as a template. A polymerase reaction inhibitory region (X) containing azobenzene (artificial nucleic acid) and a tag sequence T5 or T6 were introduced to the 5' end of each primer to synthesize tagged primers T5-X-F and T6-X-R. These two azobenzene-inserted primers were purchased as products custom-synthesized by TSUKUBA OLIGO SERVICE CO., LTD. The following shows the primer set prepared in this study.

```
Tag sequence T5:
                                          (SEQ ID NO: 25)
5'-Dd(TGGCAACATTTTTCACTGGGTTTATAG)-3'

Tag sequence T6:
                                          (SEQ ID NO: 26)
5'-Dd(GGTTAGCTTCCAACCACGTGTAGATCA)-3'

Primer T5-X-F:
                                          (SEQ ID NO: 27)
5'-Dd(TGGCAACATTTTTCACTGGGTTTATAG X

GGAAACAGCTATGACCATGA)-3'

Primer T6-X-R:
                                          (SEQ ID NO: 28)
5'-Dd(GGTTAGCTTCCAACCACGTGTAGATCA X

TCTATGCGGCATCAGAGCAG)-3'
```

The azobenzene inserted into the primers is shown in the above formula (23).

(2) PCR Using Azobenzene-Inserted Primer Set

PCR was performed using the primer set prepared in the above step (1). Specifically, a 100 µl PCR mixture was prepared by adding the primer T5-X-F and the primer T6-X-R (15 pmol each) and pUC19 (10 ng) to a 0.2-ml PCR tube, and following the instruction manual of a PCR device ExTaq (available from Takara Bio, Inc.). Thereafter, the tube was set in a thermal cycler (GeneAmp PCR System, available from Applied Biosystems), and subjected to heat treatment at 95° C. for five minutes and then exposed to 35 cycles of 95° C. for 30 seconds, 55° C. for 30 seconds, and 72° C. for 30 seconds. In this manner, a target product of approximately 330 bp was amplified. Separately, the same reaction procedure was carried out but in the absence of pUC19 as a negative control.

(3) Preparation of Latex-Bound Oligonucleotide Probe

A carboxyl group-containing polystyrene latex (solids content: 10% (w/w), available from Bangs Laboratories, Inc.) and an amino group-containing oligonucleotide probe (SEQ ID NO:29, a strand complementary to SEQ ID NO:25) were bonded by mixing them in MES buffer containing a necessary amount of a water-soluble carbodiimide, and the resulting product was blocked with monoethanolamine. The reaction solution was centrifuged, and the supernatant was then removed. The precipitate thus obtained was washed with water. After washing, the precipitate was resuspended in HEPES buffer containing a surfactant. The suspension was uniformly applied to a glass fiber pad, and dried in a vacuum oven. In this manner, a conjugate pad was prepared.

Oligonucleotide probe 7:
(SEQ ID NO: 29)
5'-$^D$d(CTATAAACCCAGTGAAAAATGTTGCCA)-NH$_2$-3'

(4) Immobilization of Oligonucleotide Probe on Solid Phase

A carboxyl group-modified nylon membrane (available from Pall Corporation, 6 mm×60 mm) was treated with a water-soluble carbodiimide, and washed with deionized water. An amino group-containing D-oligonucleotide probe having a sequence (SEQ ID NO:30) complementary to SEQ ID NO:26 was applied to the activated membrane with a dispenser along a line drawn 30 mm from one end of the membrane, and then air-dried for 15 minutes. Subsequently, the membrane was treated with Tris buffer and blocked, and then washed with water and dried.

Oligonucleotide probe 8:
(SEQ ID NO: 30)
5'-$^D$d(GATCATACACGTGGTTGGAAGCTAACC)-NH$_2$-3'

(5) Preparation of Nucleic Acid Chromatography-Like Test Strip

A test strip to be used for the detection of the PCR product amplified using the azobenzene-inserted primer set was prepared by attaching a chromatographic medium consisting of the nylon membrane prepared above, the conjugate pad prepared above, a general sample pad as a sample application zone, and an absorption pad for absorbing a developed sample and a labeling substance to a substrate consisting of a backing sheet as shown in FIG. 6.

(6) Detection of PCR Product Using Test Strip

The PCR product obtained in the step (2) was immediately applied, without being denatured, to the sample application zone on the test strip prepared in the step (5) to perform detection by chromatography. A colored line specific to the target nucleic acid was detected along the test line for the sample prepared using pUC19 as an analyte in the step (2). In contrast, there was no line detected for the negative control prepared using water instead. The detection by chromatography took a short time (10 to 15 minutes).

Example 7

(1) Preparation of Gold Colloid-Bound Oligonucleotide Probe

Gold Colloid (40 nm, 9.0×10$^{10}$ (particles/ml), available from British BioCell International) and a thiol group-containing oligonucleotide probe (SEQ ID NO: 31, a strand complementary to SEQ ID NO: 25) were mixed and incubated at 50° C. for 16 hours. The resulting mixture was centrifuged at 6000 rpm for 15 minutes, and the supernatant was removed. The residue was combined and mixed with 0.05 M sodium chloride and 5 mM phosphate buffer (pH 7), and then incubated again at 50° C. for 40 hours.

After incubation, the resulting mixture was centrifuged (6000 rpm, 15 minutes). The supernatant was removed, and the residue was combined with 5 mM phosphate buffer (pH 7). This buffer replacement procedure was performed again.

The gold colloid solution thus prepared was uniformly applied to a glass fiber pad, and dried in a vacuum oven. In this manner, a conjugate pad was prepared.

Oligonucleotide probe 7:
(SEQ ID NO: 31)
5'-$^D$d(CTATAAACCCAGTGAAAAATGTTGCCA)-SH-3'

(2) Immobilization of Oligonucleotide Probe on Solid Phase

A 3'-biotin-modified oligonucleotide probe having a sequence (SEQ ID NO:31) complementary to SEQ ID NO:26 was mixed with streptavidin. The mixture was applied along a line on a nitrocellulose membrane (product name: Hi-Flow 180, available from Millipore) with a dispenser, and then air-dried at 40° C. for 30 minutes.

Oligonucleotide probe 10:
(SEQ ID NO: 32)
5'-$^D$d(GATCATACACGTGGTTGGAAGCTAACC)-Biotin-3'

(3) Preparation of Nucleic Acid Chromatography-Like Test Strip

A test strip to be used for the detection of the PCR product amplified using the azobenzene-inserted primer set was prepared by attaching a chromatographic medium consisting of the nitrocellulose membrane prepared above, the conjugate pad prepared above, a general sample pad as a sample application zone, and an absorption pad for absorbing a developed sample and a labeling substance to a substrate consisting of a backing sheet as shown in FIG. 6.

(4) Detection of PCR Product Using Test Strip

The PCR product obtained in the step (2) of Example 6 was immediately applied, without being denatured, to the sample application zone on the test strip prepared in the step (3) to perform detection by chromatography. A colored line specific to the target nucleic acid was detected along the test line for the sample prepared using pUC19 as an analyte in the step (2) of Example 6. In contrast, there was no line detected for the negative control prepared using water instead. The detection by chromatography took a short time (10 to 15 minutes).

Example 8

(1) Immobilization of Oligonucleotide Probe on Solid Phase

An oligonucleotide probe having a sequence (SEQ ID NO:33) complementary to SEQ ID NO:26 was applied along a line on an UltraBind affinity membrane (available from Pall Corporation) with a dispenser, and then air-dried at 80° C. for one hour.

Oligonucleotide probe 11:
(SEQ ID NO: 33)
5'-$^D$d(GATCATACACGTGGTTGGAAGOTAACC)-3'

(2) Preparation of Nucleic Acid Chromatography-Like Test Strip

A test strip to be used for the detection of the PCR product amplified using the azobenzene-inserted primer set was prepared by attaching a chromatographic medium consisting of the UltraBind affinity membrane prepared above, the conjugate pad prepared above, a general sample pad as a sample application zone, and an absorption pad for absorbing a developed sample and a labeling substance to a substrate consisting of a backing sheet as shown in FIG. 6.

(3) Detection of PCR Product Using Test Strip

The PCR product obtained in the step (2) of Example 6 was immediately applied, without being denatured, to the sample application zone on the test strip prepared in the step (2) to perform detection by chromatography. A colored line specific to the target nucleic acid was detected along the test line for the sample prepared using pUC19 as an analyte in the step (2) of Example 6. In contrast, there was no line detected for the negative control prepared using water instead. The detection by chromatography took a short time (10 to 15 minutes).

Example 9

(1) Synthesis of Artificial Nucleic Acid (Azobenzene)-Inserted Primers

Three pairs of primers, a forward primer (F1) and a reverse primer (R1), a forward primer (F2) and a reverse primer (R2), and a forward primer (F3) and a reverse primer (R3), were constructed to be able to amplify approximately 330 base pairs, approximately 200 base pairs, and approximately 100 base pairs, respectively, by PCR amplification using as a target nucleic acid template three genes, pUC19 (available from Takara Bio, Inc.), an EcoRI methylase gene, and a BamHI methylase gene, respectively. A polymerase reaction inhibitory region (X) containing azobenzene (artificial nucleic acid) and a tag sequence T7 or T8, or a tag sequence T9 or T10, or a tag sequence T11 or T12 were introduced to the 5' end of each primer to synthesize tagged primers T7-X-F1 and T8-X-R1, T9-X-F2 and T10-X-R2, and T11-X-F3 and T12-X-R3. These six azobenzene-inserted primers were purchased as products custom-synthesized by TSUKUBA OLIGO SERVICE CO., LTD.

The following shows the three primer sets prepared in this study.

```
Tag sequence T7:
                                        (SEQ ID NO: 34)
5'-Dd(TGGCAACATTTTTCACTGGGTTTATAG)-3'

Tag sequence T8:
                                        (SEQ ID NO: 35)
5'-Dd(GGTTAGCTTCCAACCACGTGTAGATCA)-3'

Primer T7-X-F1:
                                        (SEQ ID NO: 36)
5'-Dd(TGGCAACATTTTTCACTGGGTTTATAG X

GGAAACAGCTATGACCATGA)-3'

Primer T8-X-R1:
                                        (SEQ ID NO: 37)
5'-Dd(GGTTAGCTTCCAACCACGTGTAGATCA X

TCTATGCGGCATCAGAGCAG)-3'

Tag sequence T9:
                                        (SEQ ID NO: 38)
5'-Dd(CGCATTGAGCAAGTGTACAGAGCAT)-3'

Tag sequence T10:
                                        (SEQ ID NO: 39)
5'-Dd(ATTATGCGTGGAGAAGCATATCATA)-3'

Primer T9-X-F2:
                                        (SEQ ID NO: 40)
5'-Dd(CGCATTGAGCAAGTGTACAGAGCAT X

AGCATTATGAATTATATGGT)-3'

Primer T10-X-R2:
                                        (SEQ ID NO: 41)
5'-Dd(ATTATGCGTGGAGAAGCATATCATA X

TTGTTTACATTTATAGCATC)-3'

Tag sequence T11:
                                        (SEQ ID NO: 42)
5'-Dd(AATTGCGCATGTCCATGTGTAA)-3'

Tag sequence T12:
                                        (SEQ ID NO: 43)
5'-Dd(TACTTTAGAGGAAACTGCTGAG)-3'

Primer T11-X-F3:
                                        (SEQ ID NO: 44)
5'-Dd(AATTGCGCATGTCCATGTGTAA X

TGGTTTTAAAACTCTGATAC)-3'

Primer T12-X-R3:
                                        (SEQ ID NO: 45)
5'-Dd(TACTTTAGAGGAAACTGCTGAG X

AGTATGATGAGGGTGTAACA)-3'
```

(2) PCR Using Three Azobenzene-Inserted Primer Sets

PCR was performed using the three primer sets prepared in the above step (1). Specifically, 100 μl PCR mixtures were prepared by adding the primer T7-X-F1 and the primer T8-X-R1, the primer T9-X-F2 and the primer T10-X-R2, and the primer T11-X-F3 and the primer T12-X-R3 (15 pmol each) and templates (10 ng each) to 0.2-ml PCR tubes, and following the instruction manual of a PCR device ExTaq (available from Takara Bio, Inc.). The following five PCR mixtures were prepared:

(i) a PCR mixture containing pUC19 (available from Takara Bio, Inc.) as a template;

(ii) a PCR mixture containing the EcoRI methylase gene as a template;

(iii) a PCR mixture containing the BamHI methylase gene as a template;

(iv) a PCR mixture containing all the three templates, pUC19 (available from Takara Bio, Inc.), EcoRI methylase gene, and BamHI methylase gene; and (v) a PCR mixture containing no template.

After these PCR mixtures were prepared, the tubes were set in a thermal cycler (GeneAmp PCR System, available from Applied Biosystems), and subjected to heat treatment at 95° C. for five minutes and then exposed to 30 cycles of 95° C. for 30 seconds, 55° C. for 30 seconds, and 72° C. for 30 seconds. Then, the following respective DNA fragments having the target sequences were amplified: (i) a DNA fragment of approximately 330 bp; (ii) a DNA fragment of approximately 200 bp; (iii) a DNA fragment of approximately 100 bp; (iv) three DNA fragments of approximately 330 bp, approximately 200 bp, and approximately 100 bp; and (v) no amplified DNA fragment (negative control).

(3) Preparation of Latex-Bound Oligonucleotide Probes

A pair of a carboxyl group-containing polystyrene latex (blue) (solids content: 10% (w/w), available from Bangs Laboratories, Inc.) and an amino group-containing oligonucleotide probe 12 (SEQ ID NO:46, a strand complementary to SEQ ID NO:34), of a carboxyl group-containing polystyrene latex (orange) (solids content: 10% (w/w), available from Bangs Laboratories, Inc.) and an amino group-containing oligonucleotide probe 13 (SEQ ID NO:47, a strand complementary to SEQ ID NO: 38), or of a carboxyl group-containing polystyrene latex (green) (solids content: 10% (w/w), available from Bangs Laboratories, Inc.) and an amino group-containing oligonucleotide probe 14 (SEQ ID NO:48, a strand complementary to SEQ ID NO:42) was bonded to each other by mixing them in MES buffer containing a necessary amount of a water-soluble carbodiimide, and the resulting products were blocked with monoethanolamine. The reaction solutions were centrifuged, their supernatants were then removed, and the precipitates thus obtained were washed with water. After washing, each precipitate was resuspended in HEPES buffer containing a surfactant to prepare an oligonucleotide probe 12-bound latex (blue), an oligonucleotide probe 13-bound latex (orange), and an oligonucleotide probe 14-bound latex (green).

These three latexes were uniformly applied to a glass fiber pad, and dried in a vacuum oven. In this manner, a conjugate pad was prepared.

```
Oligonucleotide probe 12:
                                    (SEQ ID NO: 46)
5'-Dd(CTATAAACCCAGTGAAAAATGTTGCCA)-NH2-3'

Oligonucleotide probe 13:
                                    (SEQ ID NO: 47)
5'-Dd(TTGCTCTGTACACTTGCTCAATGCG)-NH2-3'

Oligonucleotide probe 14:
                                    (SEQ ID NO: 48)
5'-Dd(TTACACATGGACATGCGCAATT)-NH2-3'
```

(4) Immobilization of Three Oligonucleotide Probes on Solid Phase

A 3'-biotin-modified oligonucleotide probe 15 having a sequence (SEQ ID NO:49) complementary to SEQ ID NO:35, a 3'-biotin-modified oligonucleotide probe 16 having a sequence (SEQ ID NO:50) complementary to SEQ ID NO:39, and a 3'-biotin-modified oligonucleotide probe 17 having a sequence (SEQ ID NO:51) complementary to SEQ ID NO:43 were each mixed with streptavidin. The mixtures were applied with dispensers to a nitrocellulose membrane (product name: Hi-Flow 135, available from Millipore) respectively along three separated lines on the membrane in the order from the upstream, and then air-dried at 40° C. for 30 minutes. In this manner, three detection lines were formed.

```
Oligonucleotide probe 15:
                                    (SEQ ID NO: 49)
5'-Dd(GATCATACACGTGGTTGGAAGCTAACC)-Biotin-3'

Oligonucleotide probe 16:
                                    (SEQ ID NO: 50)
5'-Dd(TATGATATGCTTCTCCACGCATAAT)-Biotin-3'

Oligonucleotide probe 17:
                                    (SEQ ID NO: 51)
5'-Dd(CTCAGCAGTTTCCTCTAAAGTA)-Biotin-3'
```

(5) Preparation of Nucleic Acid Chromatography-Like Test Strip

A test strip to be used for the detection of the PCR products amplified using the azobenzene-inserted primer sets was prepared by attaching a chromatographic medium consisting of the nitrocellulose membrane prepared above, the conjugate pad prepared in the step (3), a general sample pad as a sample application zone, and an absorption pad for absorbing a developed sample and a labeling substances to a substrate consisting of a backing sheet as shown in FIG. 6.

(6) Detection of PCR Products Using Test Strip

The PCR products prepared from (i) to (v) in the step (2) were each immediately applied, without being denatured, to the sample application zone on the test strip prepared in the step (5) to perform detection by chromatography. The results are shown below.

(i): Only the first detection line turned blue.

(ii): Only the second detection line turned orange.

(iii): Only the third detection line turned green.

(iv): The first, second, and third detection lines turned blue, orange, and green, respectively.

(v): No color change was observed for all the detection lines.

The results confirmed that this test strip allows specific detection of the target genes and also allows the three types of genes to be detected at one time.

The detection by chromatography took a short time (10 to 15 minutes).

Example 10

(1) Synthesis of Joint Primers

Three pairs of primers, a forward primer (Fj1) and a reverse primer (Rj1), a forward primer (Fj2) and a reverse primer (Rj2), and a forward primer (Fj3) and a reverse primer (Rj3), were constructed to be able to amplify approximately 330 base pairs, approximately 200 base pairs, and approximately 100 base pairs, respectively, by PCR amplification using as a target nucleic acid template three genes, pUC19 (available from Takara Bio, Inc.), an EcoRI methylase gene, and a BamHI methylase gene, respectively. Common sequences KF1 and KR1, common sequences KF2 and KR2, or common sequences KF3 and KR3 were respectively introduced to the 5' ends of each pair to synthesize common sequence-added primers KF1-Fj1 and KR1-Rj1, KF2-Fj2 and KR2-Rj2, and KF3-Fj3 and KR3-Rj3. These six common sequence-added primers (joint primers) were purchased as products custom-synthesized by TSUKUBA OLIGO SERVICE CO., LTD.

The following shows the three primer sets prepared in this study.

```
Common sequence KF1:
                                    (SEQ ID NO: 52)
5'-Dd(TGGGCTGACCTAGAGGTCTT)-3'

Common sequence KR1:
                                    (SEQ ID NO: 53)
5'-Dd(ATGAAATGCAGGCCATTCGG)-3'

Primer KF1-Fj1:
                                    (SEQ ID NO: 54)
5'-Dd(TGGGCTGACCTAGAGGTCTTGGAAACAGCTATGACCATGA)-3'

Primer KR1-Rj1:
                                    (SEQ ID NO: 55)
5'-Dd(ATGAAATGCAGGCCATTCGGTCTATGCGGCATCAGAGCAG)-3'

Common sequence KF2:
                                    (SEQ ID NO: 56)
5'-Dd(CCGGAACAGACACCAGGTTT)-3'
```

```
Common sequence KR2:
                                         (SEQ ID NO: 57)
5'-Pd(GAAGCTGTACCGTCACATGA)-3'

Primer KF2-Fj2:
                                         (SEQ ID NO: 58)
5'-Pd(CCGGAACAGACACCAGGTTTAGCATTATGAATTATATGGT)-3'

Primer KR2-Rj2:
                                         (SEQ ID NO: 59)
5'-Pd(GAAGCTGTACCGTCACATGATTGTTTACATTTATAGCATC)-3'

Common sequence KF3:
                                         (SEQ ID NO: 60)
5'-Pd(ATACCGATGAGTGTGCTACC)-3'

Common sequence KR3:
                                         (SEQ ID NO: 61)
5'-Pd(TGGCCTGTGTGACACTATGC)-3'

Primer KF3-Fj3:
                                         (SEQ ID NO: 62)
5'-Pd(ATACCGATGAGTGTGCTACCTGGTTTTAAAACTCTGATAC)-3'

Primer KR3-Rj3:
                                         (SEQ ID NO: 63)
5'-Pd(TGGCCTGTGTGACACTATGCAGTATGATGAGGGTGTAACA)-3'
```

(2) Synthesis of Artificial Nucleic Acid (Azobenzene)-Inserted Primers

Three pairs of primers were constructed to respectively contain the same common sequences as those of the joint primers prepared in the step (1) and thereby to be able to respectively bind to three PCR fragments amplified using the joint primer sets. A polymerase reaction inhibitory region (X) containing azobenzene (artificial nucleic acid) and a tag sequence T16 or T17, or a tag sequence T18 or T19, or a tag sequence T20 or T21 were introduced to the 5' end of each primer to synthesize tagged primers T16-X-KF1 and T17-X-KR1, T18-X-KF2 and T19-X-KR2, and T20-X-KF3 and T21-X-KR3. These six azobenzene-inserted primers were purchased as products custom-synthesized by TSUKUBA OLIGO SERVICE CO., LTD.

The following shows the three primer sets prepared in this study.

```
Tag sequence T16:
                                         (SEQ ID NO: 64)
5'-Pd(TGGCAACATTTTTCACTGGGTTTATAG)-3'

Tag sequence T17:
                                         (SEQ ID NO: 65)
5'-Pd(GGTTAGCTTCCAACCACGTGTAGATCA)-3'

Primer T16-X-KF1:
                                         (SEQ ID NO: 66)
5'-Pd(TGGCAACATTTTTCACTGGGTTTATAG X TGGGCTGACCTA
GAGGTCTT)-3'

Primer T17-X-KR1:
                                         (SEQ ID NO: 67)
5'-Pd(GGTTAGCTTCCAACCACGTGTAGATCA X ATGAAATGCAGG
CCATTCGG)-3'

Tag sequence T18:
                                         (SEQ ID NO: 68)
5'-Pd(CGCATTGAGCAAGTGTACAGAGCAT)-3'

Tag sequence T19:
                                         (SEQ ID NO: 69)
5'-Pd(ATTATGCGTGGAGAAGCATATCATA)-3'

Primer T18-X-KF2:
                                         (SEQ ID NO: 70)
5'-Pd(CGCATTGAGCAAGTGTACAGAGCAT X CCGGAACAGACA
CCAGGTTT)-3'

Primer T19-X-KR2:
                                         (SEQ ID NO: 71)
5'-Pd(ATTATGCGTGGAGAAGCATATCATA X GAAGCTGTACCGT
CACATGA)-3'

Tag sequence T20:
                                         (SEQ ID NO: 72)
5'-Pd(AATTGCGCATGTCCATGTGTAA)-3'

Tag sequence T21:
                                         (SEQ ID NO: 73)
5'-Pd(TACTTTAGAGGAAACTGCTGAG)-3'

Primer T20-X-KF3:
                                         (SEQ ID NO: 74)
5'-Pdd(AATTGCGCATGTCCATGTGTAA X ATACCGATGAGTGTGC
TACC)-3'

Primer T21-X-KR3:
                                         (SEQ ID NO: 75)
5'-Pd(TACTTTAGAGGAAACTGCTGAG X TGGCCTGTGTGACAC
TATGC)-3'
```

(3) PCR Using Joint Primers and Azobenzene-Inserted Primers

PCR was performed using the six primer sets prepared in the above-described steps (1) and (2). Specifically, 100 μl PCR mixtures were prepared by adding the primer KF1-Fj1, the primer KR1-Rj1, the primer KF2-Fj2, the primer KR2-Rj2, the primer KF3-Fj3, the primer KR3-Rj3, the primer T16-X-KF1, the primer T17-X-KR1, the primer T18-X-KF2, the primer T19-X-KR2, the primer T20-X-KF3, and the primer T21-X-KR3 (8 pmol each), and templates (10 ng each) to 0.2-ml PCR tubes, and following the instruction manual of a PCR device ExTaq (available from Takara Bio, Inc.).

The following five types of PCR mixtures were prepared:
(i) a PCR mixture containing pUC19 (available from Takara Bio, Inc.) as a template;
(ii) a PCR mixture containing the EcoRI methylase gene as a template;
(iii) a PCR mixture containing the BamHI methylase gene as a template;
(iv) a PCR mixture containing all the three templates, pUC19 (available from Takara Bio, Inc.), EcoRI methylase gene, and BamHI methylase gene; and
(v) a PCR mixture containing no template.

After these PCR mixtures were prepared, the tubes were set in a thermal cycler (GeneAmp PCR System, available from Applied Biosystems), and subjected to heat treatment at 95° C. for five minutes and then exposed to 30 cycles of 95° C. for 30 seconds, 55° C. for 30 seconds, and 72° C. for 30 seconds. Then, the following respective DNA fragments having the target sequences were amplified: (i) a DNA fragment of approximately 360 bp; (ii) a DNA fragment of approximately 230 bp; (iii) a DNA fragment of approximately 130 bp; (iv) three DNA fragments of approximately 360 bp, approximately 230 bp, and approximately 130 bp; and (v) no amplified DNA fragment (negative control).

(4) Preparation of Latex-Bound Oligonucleotide Probes

A pair of a carboxyl group-containing polystyrene latex (blue) (solids content: 10% (w/w), available from Bangs Laboratories, Inc.) and an amino group-containing oligonucleotide probe 18 (SEQ ID NO:76, a strand complementary to SEQ ID NO:64), of a carboxyl group-containing polystyrene latex (orange) (solids content: 10% (w/w), available from Bangs Laboratories, Inc.) and an amino group-containing oligonucleotide probe 19 (SEQ ID NO:77, a strand complementary to SEQ ID NO: 68), or of a carboxyl group-containing polystyrene latex (green) (solids content: 10% (w/w), available from Bangs Laboratories, Inc.) and an amino group-containing oligonucleotide probe 20 (SEQ ID NO:78, a strand complementary to SEQ ID NO:72) was bonded to each other by mixing them in MES buffer containing a necessary amount of a water-soluble carbodiimide, and the resulting products were blocked with monoethanolamine. The reaction solutions were centrifuged, their supernatants were then removed, and the precipitates thus obtained were washed with water. After washing, each precipitate was resuspended in HEPES buffer containing a surfactant to prepare an oligonucleotide probe 18-bound latex (blue), an oligonucleotide probe 19-bound latex (orange), and an oligonucleotide probe 20-bound latex (green).

These three latexes were uniformly applied to a glass fiber pad, and dried in a vacuum oven. In this manner, a conjugate pad was prepared.

```
Oligonucleotide probe 18:
                                       (SEQ ID NO: 76)
5'-Pd(CTATAAACCCAGTGAAAAATGTTGCCA)-NH2-3'

Oligonucleotide probe 19:
                                       (SEQ ID NO: 77)
5' -Pd(TTGCTCTGTACACTTGCTCAATGCG)-NH2-3'

Oligonucleotide probe 20:
                                       (SEQ ID NO: 78)
5'-Pd(TTACACATGGACATGCGCAATT)-NH2-3'
```

(5) Immobilization of Three Oligonucleotide Probes on Solid Phase

A 3'-biotin-modified oligonucleotide probe 21 having a sequence (SEQ ID NO:79) complementary to SEQ ID NO: 65, a 3'-biotin-modified oligonucleotide probe 22 having a sequence (SEQ ID NO:80) complementary to SEQ ID NO:69, and a 3'-biotin-modified oligonucleotide probe 23 having a sequence (SEQ ID NO:81) complementary to SEQ ID NO:73 were each mixed with streptavidin. The mixtures were applied with dispensers to a nitrocellulose membrane (product name: Hi-Flow 135, available from Millipore) respectively along three separated lines on the membrane in the order from the upstream, and then air-dried at 40° C. for 30 minutes. In this manner, three detection lines were formed.

```
oligonucleotide probe 21:
                                       (SEQ ID NO: 79)
5'-Pd(GATCATACACGTGGTTGGAAGCTAACC)-Biotin-3'

Oligonucleotide probe 22:
                                       (SEQ ID NO: 80)
5'-Pd(TATGATATGCTTCTCCACGCATAAT)-Biotin-3'

Oligonucleotide probe 23:
                                       (SEQ ID NO: 81)
5'-Pd(CTCAGCAGTTTCCTCTAAAGTA)-Biotin-3'
```

(6) Preparation of Nucleic Acid Chromatography-Like Test Strip

A test strip to be used for the detection of the PCR products amplified using the azobenzene-inserted primer sets was prepared by attaching a chromatographic medium consisting of the nitrocellulose membrane prepared above, the conjugate pad prepared in the step (4), a general sample pad as a sample application zone, and an absorption pad for absorbing a developed sample and a labeling substances to a substrate consisting of a backing sheet as shown in FIG. 6.

(7) Detection of PCR Products Using Test Strip

The PCR amplified products prepared from (i) to (v) in the step (3) were immediately applied, without being denatured, to the sample application zone on the test strip prepared in the step (6) to perform detection by chromatography.

The results are shown below.

(i): Only the first detection line turned blue.

(ii): Only the second detection line turned orange.

(iii): Only the third detection line turned green.

(iv): The first, second, and third detection lines turned blue, orange, and green, respectively.

(v): No color change was observed for all the detection lines.

The results confirmed that this test strip allows specific detection of the target genes and also allows the three types of genes to be detected. The detection by chromatography took a short time (10 to 15 minutes).

Example 11

(1) Synthesis of Artificial Nucleic Acid (Azobenzene)-Inserted Primers

In this example, *Escherichia coli* (*E. coli* DH5α) transfected with the plasmid pUC19 as a target was used. A forward primer (F) and a reverse primer (R) were constructed to be able to amplify approximately 330 base pairs by PCR amplification using pUC19 as a template. A polymerase reaction inhibitory region (X) containing azobenzene (artificial nucleic acid) and a tag sequence T25 or T26 were introduced to the 5' end of each primer to synthesize tagged primers T25-X-F and T26-X-R. These two azobenzene-inserted primers were purchased as products custom-synthesized by TSUKUBA OLIGO SERVICE CO, LTD.

The following shows the primer sets prepared in this study.

```
Tag sequence T25:
                                       (SEQ ID NO: 82)
5'-Pd(TGGCAACATTTTTCACTGGGTTTATAG)-3'

Tag sequence T26:
                                       (SEQ ID NO: 83)
5'-Pd(GGTTAGCTTCCAACCACGTGTAGATCA)-3'

Primer F:
                                       (SEQ ID NO: 84)
5'-Pd(GGAAACAGCTATGACCATGA)-3'

Primer R:
                                       (SEQ ID NO: 85)
5'-Pd(TCTATGCGGCATCAGAGCAG)-3'

Primer T25-X-F:
                                       (SEQ ID NO: 86)
5'-Pd(TGGCAACATTTTTCACTGGGTTTATAG X GGAAACAGCTA
TGACCATGA)-3'

Primer T26-X-R:
                                       (SEQ ID NO: 87)
5'-Pd(GGTTAGCTTCCAACCACGTGTAGATCA X TCTATGCGGCA
TCAGAGCAG)-3'
```

(2) PCR Using Azobenzene-Inserted Primer Set

A colony of *Escherichia coli* (*E. coli* DH5α) cells transfected with the plasmid pUC19 was collected and mixed in 1 ml of water, and then was subjected to PCR using the primer set prepared in the above step (1). Specifically, a 25 μl PCR mixture was prepared by adding the primer F and the primer R (5 pmol each) and the *Escherichia coli* suspension (1 µl) to a 0.2-ml PCR tube, and following the instruction manual of a PCR device ExTaq (available from Takara Bio, Inc.). Subsequently, the tube was set in a thermal cycler (GeneAmp PCR System, available from Applied Biosystems), and subjected to heat treatment at 95° C. for five minutes and then exposed to 30 cycles of 95° C. for 30 seconds, 55° C. for 30 seconds, and 72° C. for 30 seconds. In this manner, a target product of approximately 330 bp was amplified. Separately, the same reaction procedure was carried out but in the absence of the suspension as a negative control.

(3) Preparation of Gold Colloid-Bound Oligonucleotide Probe

Gold Colloid (10 nm, 5.7×10$^{12}$ (particles/ml), available from British BioCell International) and an anti-FITC antibody solution (5 mM phosphate buffer, pH 7) were mixed and left standing for 20 minutes at room temperature. One half volume of a solution containing 1% BSA and 0.1% PEG was added, and the resulting mixture was centrifuged at 10000 rpm for 25 minutes. After removing the supernatant, the residue was combined and mixed with the solution containing 1% BSA and 0.1% PEG, and the mixture was then centrifuged at 10000 rpm for 25 minutes. After the centrifugation, the supernatant was removed and the residue was combined with 5 mM phosphate buffer (pH 7). This buffer replacement procedure was performed again.

The gold colloid solution thus prepared was mixed with a 3'-FITC-modified oligonucleotide probe 24 (SEQ ID NO:88, a strand complementary to SEQ ID NO:82). The mixture was uniformly applied to a glass fiber pad, and dried in a vacuum oven. In this manner, a conjugate pad was prepared.

```
Oligonucleotide probe 24:
                                    (SEQ ID NO: 88)
5'-Dd(CTATAAACCCAGTGAAAAATGTTGCCA)-FITC-3'
```

(4) Immobilization of Oligonucleotide Probe on Solid Phase

A 3'-biotin-modified oligonucleotide probe 25 having a sequence (SEQ ID NO:89) complementary to SEQ ID NO:83 was mixed with streptavidin. The mixture was applied with a dispenser along a line on a nitrocellulose membrane (product name: Hi-Flow 180, available from Millipore), and then air-dried at 40° C. for 30 minutes.

```
Oligonucleotide probe 25:
                                    (SEQ ID NO: 89)
5'-Dd(GATCATACACGTGGTTGGAAGCTAACC)-Biotin-3'
```

(5) Preparation of Nucleic Acid Chromatography-Like Test Strip

A test strip to be used for the detection of the PCR product amplified using the azobenzene-inserted primer set was prepared by attaching a chromatographic medium consisting of the nitrocellulose membrane prepared above, the conjugate pad prepared above, a general sample pad as a sample application zone, and an absorption pad for absorbing a developed sample and a labeling substance to a substrate consisting of a backing sheet as shown in FIG. 6.

(6) Detection of PCR Product Using Test Strip

The PCR product obtained in the step (2) was immediately applied, without being denatured, to the sample application zone on the test strip prepared in the step (5) to perform detection by chromatography. A colored line specific to the target nucleic acid was detected along the test line for the sample prepared using *Escherichia coli* cells as an analyte in the step (2). In contrast, there was no line detected for the negative control prepared without using *Escherichia coli* cells. The detection by chromatography took a short time (10 to 15 minutes).

Example 12

(1) Synthesis of SNP Target

In this example, two types of synthetic 50-bp DNAs were prepared as targets. These two DNAs only contain a difference in a single base at position 20 from the end and thus contain single nucleotide polymorphisms (SNPs). An SNP detection test was performed based assuming that Target 1 was wild-type (WT) and Target 2 was mutant (MT).

The following shows the sequence of a single strand of the double-stranded DNA of Target 1 or Target 2. The underlined indicates a difference in a single base.

```
Target 1 (WT):
                                    (SEQ ID NO: 90)
CACACCGCATATGGTGCACTCTCAGTACAATCTGCTCTGATGCCGCATAG Target 2 (MT):
                                    (SEQ ID NO: 91)
CACACCGCATATGGTGCACTCTCAGTACAAGCTGCTCTGATGCCGCATAG
```

(2) Synthesis of Artificial Nucleic Acid (Azobenzene)-Inserted Primers

A forward primer (Fwt), a reverse primer (Rwt), and a reverse primer (Rmt) were constructed to be able to amplify approximately 50 base pairs by PCR amplification using Target 1 or Target 2 synthesized in the step (1) as a template. A polymerase reaction inhibitory region (X) containing azobenzene (artificial nucleic acid) and a tag sequence T27, T28 or T29 were introduced to the 5' end of each primer to synthesize tagged primers T27-X-Fwt, T28-X-Rwt, and T29-X-Rmt. These three azobenzene-inserted primers were purchased as products custom-synthesized by TSUKUBA OLIGO SERVICE CO., LTD.

The following shows the primer sets prepared in this study.

```
Tag sequence T27:
                                    (SEQ ID NO: 92)
5'-Dd(TGGCAACATTTTTCACTGGGTTTATAG)-3'

Tag sequence T28:
                                    (SEQ ID NO: 93)
5'-Dd(GGTTAGCTTCCAACCACGTGTAGATCA)-3'

Tag sequence T29:
                                    (SEQ ID NO: 94)
5'-Dd(CGCATTGAGCAAGTGTACAGAGCAT)-3'

Primer Fwt:
                                    (SEQ ID NO: 95)
5'-Dd(CACACCGCATATGGTGCACT)-3'

Primer Rwt:
                                    (SEQ ID NO: 96)
5'-Dd(CTATGCGGCATCAGAGCAGA)-3'

Primer Rmt:
                                    (SEQ ID NO: 97)
5'-Dd(CTATGCGGCATCAGAGCAGC)-3'

Primer T27-X-Fwt:
                                    (SEQ ID NO: 98)
5'-Dd(TGGCAACATTTTTCACTGGGTTTATAG X CACACCGCATAT
GGTGCACT)-3'
```

-continued

Primer T28-X-Rwt:
(SEQ ID NO: 99)
5'-$^D$d(GGTTAGCTTCCAACCACGTGTAGATCA X TCTATGCGGCAT CAGAGCAGA)-3'

Primer T29-X-Rmt:
(SEQ ID NO: 100)
5'-$^D$d(CGCATTGAGCAAGTGTACAGAGCAT X TCTATGCGGCATC AGAGCAGC)-3'

(3) PCR Using Azobenzene-Inserted Primer Set

PCR was carried out using the sample solutions containing Target 1 or Target 2 prepared in the step (1) and the three primers synthesized in the step (2). Specifically, 100 μl PCR mixtures were prepared by adding the primer T27-X-Fwt, the primer T28-X-Rwt, and the primer T29-X-Rmt (5 pmol each), and templates (1 fmol each) to 0.2-ml PCR tubes, and following the instruction manual of a PCR kit ExTaq (available from Takara Bio, Inc.).

The following four types of templates were used to prepare the PCR mixtures:
(i) Target 1 used as template (homozygous type);
(ii) Target 1 and Target 2 used as templates (heterozygous type);
(iii) Target 2 used as template (homozygous type); and
(iv) no target (but with water).

After these PCR mixtures were prepared, the tubes were set in a thermal cycler (GeneAmp PCR System, available from Applied Biosystems), and subjected to heat treatment at 95° C. for five minutes and then exposed to 30 cycles of 95° C. for 10 seconds, 55° C. for 30 seconds, and 72° C. for 10 seconds. Then, the following respective DNA fragments having the target sequences were amplified: (i) a DNA fragment of approximately 50 bp; (ii) a DNA fragment of approximately 50 bp; (iii) a DNA fragment of approximately 50 bp; and (iv) no amplified DNA fragment (negative control).

(4) Preparation of Gold Colloid-Bound Oligonucleotide Probe

Gold Colloid (40 nm, 9.0×10$^{10}$ (particles/ml), available from British BioCell International) and a thiol group-containing oligonucleotide probe 26 (SEQ ID NO:101, a strand complementary to SEQ ID NO:92) were mixed and then incubated at 50° C. for 16 hours. The resulting mixture was centrifuged at 6000 rpm for 15 minutes, and the supernatant was removed. The residue was combined and mixed with 5 mM phosphate buffer (pH 7) containing 0.05 M sodium chloride. Then, the mixture was incubated again at 50° C. for 40 hours. After incubation, the resulting mixture was centrifuged (6000 rpm, 15 minutes), the supernatant was removed, and the residue was combined with 5 mM phosphate buffer (pH 7). This buffer replacement procedure was performed again.

The gold colloid solution thus prepared was uniformly applied to a glass fiber pad, and dried in a vacuum oven. In this manner, a conjugate pad was prepared.

Oligonucleotide probe 26:
(SEQ ID NO: 101)
5'-$^D$d(CTATAAACCCAGTGAAAAATGTTGCCA)-SH-3'

(5) Immobilization of Two Oligonucleotide Probes on Solid Phase

A 3'-biotin-modified oligonucleotide probe 27 having a sequence (SEQ ID NO:102) complementary to SEQ ID NO:93 and a 3'-biotin-modified oligonucleotide probe 28 having a sequence (SEQ ID NO:103) complementary to SEQ ID NO:94 were each mixed with streptavidin. The mixtures were applied with dispensers at two positions apart from each other on a nitrocellulose membrane (product name: Hi-Flow 135, available from Millipore) in the order from the upstream, and then air-dried at 40° C. for 30 minutes. Thus, two detection lines were prepared.

Oligonucleotide probe 27:
(SEQ ID NO: 102)
5'-$^D$d(GATCATACACGTGGTTGGAAGCTAACC)-Biotin-3'

Oligonucleotide probe 28:
(SEQ ID NO: 103)
5'-$^D$d(TTGCTCTGTACACTTGCTCAATGCG)-Biotin-3'

(6) Preparation of Nucleic Acid Chromatography-Like Test Strip

A test strip to be used for the detection of the PCR products amplified using the spacer (azobenzene)-inserted primer set was prepared by attaching a chromatographic medium consisting of the nitrocellulose membrane prepared in the step (5), the conjugate pad prepared in the step (4), a general sample pad as a sample application zone, and an absorption pad for absorbing a developed sample and a labeling substance to a substrate consisting of a backing sheet as shown in FIG. 6.

(7) Detection of PCR Products Using Test Strip

The PCR products prepared from (i) to (iv) in the step (3) were immediately applied, without being denatured, to the sample application zone on the test strip prepared in the step (6) to perform detection by chromatography.

The results are shown below.
(i): Only the first detection line was colored.
(ii): Both the first and second detection lines were colored.
(iii): Only the second detection line was colored.
(iv): Neither of the detection lines was colored.

The results confirmed that this test strip allows specific detection of the target genes and also allows the homozygous and heterozygous SNPs to be identified at one time. The detection by chromatography took a short time (5 to 15 minutes).

Example 13

(1) Synthesis of Spacer (5'-5' Linkage+3'-3' Linkage)-Inserted Primers

In this example, the following three kinds of samples were used: soft flour (available from Nisshin Seifun Group Inc.); buckwheat flour (available from OBINATA Co., Ltd.); and peanut (available from Le-Monde-Alico Co. LTD). Three pairs of primers, a forward primer (Fwtr) and a reverse primer (Rwtr), a forward primer (FFAG) and a reverse primer (RFAG), and a forward primer (Fagg) and a reverse primer (Ragg), were constructed to be able to amplify an approximately 141-bp DNA, an approximately 127-bp DNA, and an approximately 95-bp DNA by PCR amplification of the samples, respectively. A polymerase reaction inhibitory region (X) containing a structure of (5'-5' linkage+dA+3'-3' linkage) and a tag sequence T7 or T8, or a tag sequence T9 or T10, or a tag sequence T11 or T12 were introduced to the 5' end of each primer to synthesize tagged spacer-inserted primers T7-X-Fwtr and T8-X-Rwtr, T9-X-FFAG and T10-X-RFAG, and T11-X-Fagg and T12-X-Ragg. These six tag spacer-inserted primers were purchased as products custom-synthesized by TSUKUBA OLIGO SERVICE CO., LTD.

The following shows the three primer sets prepared in this study.

```
Primer T7-X-Fwtr:
                                    (SEQ ID NO: 104)
5'-Dd(TGGCAACATTTTTCACTGGGTTTATAG X CATCACAATCAA

CTTATGGTGG)-3'

Primer T8-X-Rwtr:
                                    (SEQ ID NO: 105)
5'-Dd(GGTTAGCTTCCAACCACGTGTAGATCA X TTTGGGAGTTGA

GACGGGTTA)-3'

Primer T9-X-FFAG:
                                    (SEQ ID NO: 106)
5'-Dd(CGCATTGAGCAAGTGTACAGAGCAT X AACGCCATAACCAG

CCCGATT)-3'

Primer T10-X-RFAG:
                                    (SEQ ID NO: 107)
5'-Dd(ATTATGCGTGGAGAAGCATATCATA X CCTCCTGCCTCCCA

TTCTTC)-3'

Primer T11-X-Fagg:
                                    (SEQ ID NO: 108)
5'-Dd(AATTGCGCATGTCCATGTGTAA X CGAAGGAAACCCCGCAA

TAAAT)-3'

Primer T12-X-Ragg:
                                    (SEQ ID NO: 109)
5'-Dd(TACTTTAGAGGAAACTGCTGAG X CGACGCTATTTACCTTG

TTGAG)-3'
```

(2) Purification of Genomic DNAs from Samples

The genomic DNAs were purified from the respective samples: soft flour, buckwheat flour, and ground peanut (2 g each). First, a portion of each sample was weighed into a centrifuge tube (volume: 50 mL), combined with 15 mL of CTAB buffer, and mixed with a homogenizer. Each of the mixtures was combined with 30 mL of CTAB buffer, tumbled and mixed, and then heated at 55° C. for 30 minutes. After heating, the solutions were stirred to be homogeneous, and 600 μL portions were then sampled from the respective solutions into microtubes (volume: 1.5 mL).

Extraction of nucleic acids from these homogeneous solutions was carried out as follows. To each of these homogeneous solutions was added 500 μL of a phenol/chloroform mixture (a 1:1 (v/v) mixture of 1 M Tris-HCl (pH 8.0) saturated phenol and chloroform/isoamyl alcohol), and the resulting mixtures were tumbled and mixed, and then gently suspended with a vortex mixer. After suspension, centrifugation was performed at room temperature at 7,500×g for 15 minutes, and the aqueous phase (upper layer) thus separated was transferred into another microtube. The aqueous phase was combined with 500 μL of a chloroform/isoamyl alcohol mixture (a 24:1 (v/v) mixture of chloroform and isoamyl alcohol) again, tumbled and mixed, and then gently suspended with a vortex mixer. Centrifugation was performed at room temperature at 7,500×g for 15 minutes, and the aqueous phase (upper layer) thus separated was transferred into another microtube. The separated aqueous phase was combined with the same volume of isopropyl alcohol, tumbled and mixed, and then centrifuged at room temperature at 7,500×g for 15 minutes. The supernatant was removed by decantation. Next, 500 μL of 70% ethanol was added slowly down the wall, and then centrifuged at room temperature at 7,500×g for 1 minute. After centrifugation, ethanol was sucked and discharged as much as possible without touching the sediment. The nucleic acid sediment left in each tube was dried by vacuum drying with an aspirator for 2 to 3 minutes. At this time, care was taken not to dry the sediments completely. Each residue was combined with 50 μL of TE buffer (10 mM Tris-HCl (pH 8.0), 1 mM EDTA (pH 8.0)) and they were mixed well, and then left standing at room temperature for 15 minutes. In this period, the mixtures were tumbled and mixed several times to accelerate dissolving the sediments completely. After the sediments were completely dissolved, the respective solutions were used as DNA sample stock solutions.

The CTAB buffer was prepared as follows: 8 mL of 0.5 mM EDTA (pH 8.0), 20 mL of 1 M Tris-HCl (pH 8.0), and 56 mL of a 5 M NaCl aqueous solution were weighed into a beaker and mixed, and then combined with water to a volume of approximately 150 mL. Then, 4 g of cetyltrimethylammonium bromide (CTAB) was added to the mixture under stirring and completely dissolved. Water was further added to a total volume of 200 mL, and the solution was sterilized in an autoclave.

(3) PCR Using Three Spacer (5'-5' Linkage+3'-3' Linkage)-Inserted Primer Sets

PCR was performed using the three primer sets prepared in the step (1). Specifically, 100 μl PCR mixtures were prepared by adding the primer T7-X-Fwtr, the primer T8-X-Rwtr, the primer T9-X-FFAG, the primer T10-X-RFAG, the primer T11-X-Fagg, and the primer T12-X-Ragg (15 pmol each), and the DNA sample stock solutions to 0.2-ml PCR tubes, and following the instruction manual of a PCR device ExTaq (available from Takara Bio, Inc.).

The following five types of DNA sample stock solutions were used to prepare the PCR mixtures:
(i) the DNA sample stock solution of soft flour used as a template;
(ii) the DNA sample stock solution of buckwheat flour used as a template;
(iii) the DNA sample stock solution of peanut used as a template;
(iv) All the three DNA sample stock solutions of soft flour, buckwheat flour, and peanut used as template; and
(v) No template used.

After these PCR mixtures were prepared, the tubes were set in a thermal cycler (GeneAmp PCR System, available from Applied Biosystems), and subjected to heat treatment at 95° C. for five minutes and then exposed to 30 cycles of 95° C. for 30 seconds, 55° C. for 30 seconds, and 72° C. for 30 seconds. Then, the following respective DNA fragments having the target sequences were amplified: (i) a DNA fragment of approximately 141 bp; (ii) a DNA fragment of approximately 127 bp; (iii) a DNA fragment of approximately 95 bp; (iv) three DNA fragments of approximately 141 bp, approximately 127 bp, and approximately 95 bp; and (v) no amplified DNA fragment (negative control).

(4) Preparation of Gold Colloid-Bound Oligonucleotide Probes

Gold Colloid (40 nm, $9.0 \times 10^{10}$ (particles/ml), available from British BioCell International) was mixed with a thiol group-containing oligonucleotide probe 29 (SEQ ID NO:110, a strand complementary to SEQ ID NO: 34), a thiol group-containing oligonucleotide probe 30 (SEQ ID NO: 111, a strand complementary to SEQ ID NO:38), or a thiol group-containing oligonucleotide probe 31 (SEQ ID NO: 112, a strand complementary to SEQ ID NO: 42), and incubated at 50° C. for 16 hours. Centrifugation was performed at 6000 rpm for 15 minutes, and the supernatant was removed. Each residue was combined and mixed with 5 mM phosphate buffer (pH 7) containing 0.05 M sodium chloride, and then incubated again at 50° C. for 40 hours. After incubation, the resulting mixtures were centrifuged (6000 rpm, 15 minutes), their supernatants were removed, and the residues were combined with 5 mM phosphate buffer (pH 7). This buffer replacement procedure was performed again.

The gold colloid solutions thus prepared were uniformly applied to a glass fiber pad, and dried in a vacuum oven. In this manner, a conjugate pad was prepared.

```
Oligonucleotide probe 29:
                                        (SEQ ID NO: 110)
5'-Dd(CTATAAACCCAGTGAAAAATGTTGCCA)-SH-3'

Oligonucleotide probe 30:
                                        (SEQ ID NO: 111)
5'-Dd(TTGCTCTGTACACTTGCTCAATGCG)-SH-3'

Oligonucleotide probe 31:
                                        (SEQ ID NO: 112)
5'-Dd(TTACACATGGACATGCGCAATT)-SH-3')
```

(5) Immobilization of Three Oligonucleotide Probes on Solid Phase

The oligonucleotide probes 15, 16, and 17 were applied along lines in the same manner as in the step (4) of Example 9, and then dried and immobilized on the nitrocellulose membrane.

(6) Preparation of Nucleic Acid Chromatography-Like Test Strip

A test strip to be used for the detection of the PCR products amplified using the spacer (5'-5' linkage+3'-3' linkage)-inserted primer sets was prepared by attaching a chromatographic medium consisting of the nitrocellulose membrane prepared in the step (5), the conjugate pad prepared in the step (4), a general sample pad as a sample application zone, and an absorption pad for absorbing a developed sample and a labeling substance to a substrate consisting of a backing sheet as shown in FIG. 6.

(7) Detection of PCR Products Using Test Strip

The PCR products prepared from (i) to (iv) in the step (3) were immediately applied, without being denatured, to the sample application zone on the test strip prepared in the step (6) to perform detection by chromatography.

Figure 12:
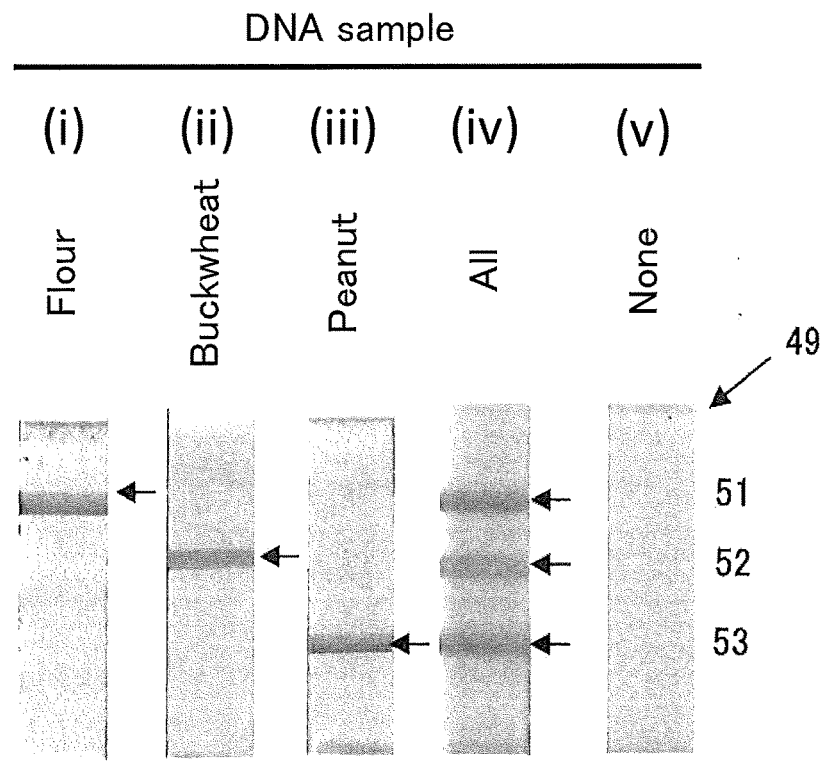
FIG. 12 shows examples of the results of the detection of PCR amplified products by a chromatography-like strip of Example 13.

The results are shown in (i) to (v) below and in FIG. 12.
(i): Only the first detection line was colored.
(ii): Only the second detection line was colored.
(iii): Only the third detection line was colored.
(iv): All the first, second and third detection lines were colored.
(v): No color change was observed for all the detection lines.

These results confirmed that this test strip allows specific detection of the target genes and also allows the three types of samples to be detected at one time. The detection by chromatography took a short time (5 to 15 minutes).

Example 14

Detection of Presence of pUC19 Insert
(1) Preparation of Target DNAs (pUC19 and Insert-Containing pUC19)

Figure 13:
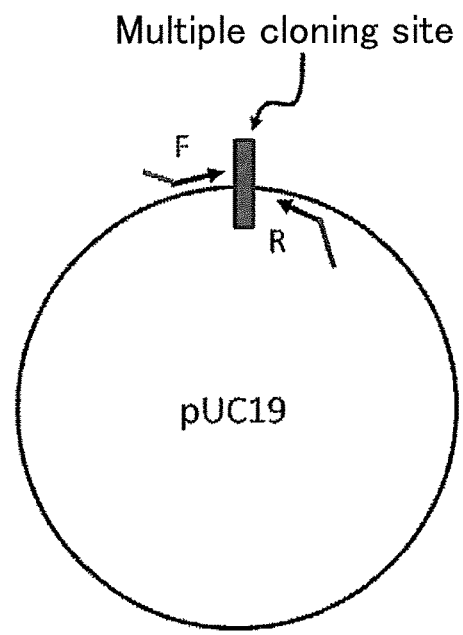
FIG. 13 is a schematic diagram of Target 1 used in Example 14.
Figure 14:
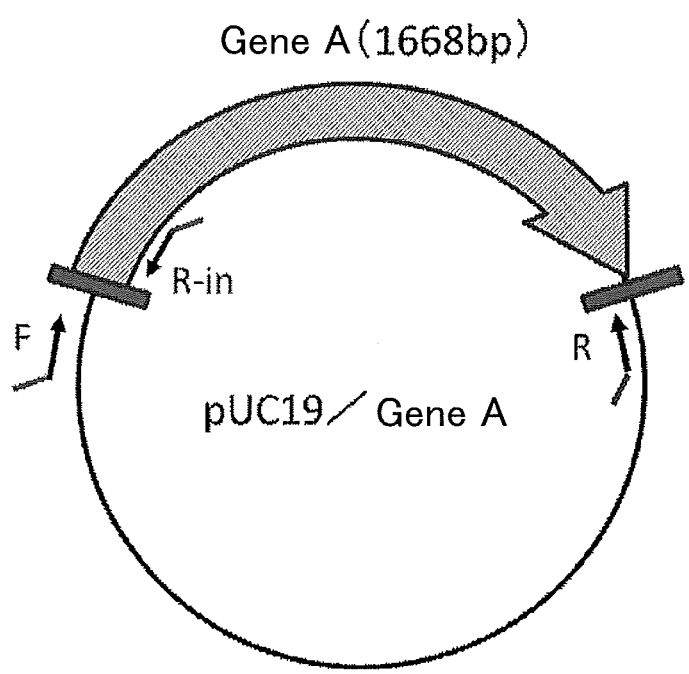
FIG. 14 is a schematic diagram of Target 2 used in Example 14.

In this example, two plasmid DNAs were prepared as targets. FIGS. 13 and 14 are schematic maps of the targets. Target 1 was the plasmid pUC19 DNA (available from Takara Bio, Inc.), and Target 2 was a plasmid (pUC19/Gene A) in which Gene A (1668 bp) was inserted at the multiple cloning site of pUC19 as an insert.

Gene A sequence (SEQ ID NO:113)
Target 1: pUC19 sequence (SEQ ID NO:114)
Target 2: pUC19 sequence/Gene A (SEQ ID NO:115)
(2) Synthesis of C6 Linker-Inserted Primers As shown in FIGS. 13 and 14, a forward primer (F) and a reverse primer (R) were constructed to respectively correspond to the sites of the pUC19 sequence between which the multiple cloning site was located, and a reverse primer (R-in) was constructed to correspond to a part of the insert gene A sequence. When PCR is performed using the forward primer F and the reverse primer R, a 118-bp amplified product will be obtained for pUC19 (Target 1), and a 1768-bp amplified product for pUC19/Gene A (insert-containing Target 2). Also, when PCR is performed using the forward primer F and the reverse primer R-in, a 101-bp amplified product will be generated for (insert-containing) Target 2. A polymerase reaction inhibitory region (X) containing a C6 linker and a tag sequence T27, T28, or T29 as described in Example 12 were introduced to the 5' end of each primer to synthesize tagged primers T27-X-F, T28-X-R, and T29-X-R-in. These three C6 linker-inserted primers were purchased as products custom-synthesized by TSUKUBA OLIGO SERVICE CO., LTD.

The following shows the primer sets prepared in this study.

```
Primer F:
                                        (SEQ ID NO: 116)
5'-Dd(GGAAACAGCTATGACCATGA)-3'

Primer R:
                                        (SEQ ID NO: 117)
5'-Dd(TTTCCCAGTCACGACGTTGT)-3'

Primer R-in:
                                        (SEQ ID NO: 118)
5'-Dd(AGTGCGTGCTGGGCTCTTC)-3'

Primer T27-X-F:
                                        (SEQ ID NO: 119)
5'-Dd(TGGCAACATTTTTCACTGGGTTTATAG X GGAAACAGCTAT
GACCATGA)-3'

Primer T28-X-R:
                                        (SEQ ID NO: 120)
5'-Dd(GGTTAGCTTCCAACCACGTGTAGATCA X TTTCCCAGTCAC
GACGTTGT)-3'

Primer T29-X-R-in:
                                        (SEQ ID NO: 121)
5'-Dd(CGCATTGAGCAAGTGTACAGAGCAT X AGTGCGTGCTGGGC
TCTTC)-3'
```

(3) PCR Using C6 Linker-Inserted Primer Sets

PCR was performed using a solution of Target 1 or Target 2 prepared in the step (1) and the three types of primers synthesized in the step (2). Specifically, 100 µl PCR mixtures were prepared by adding the primer T27-X-F, the primer T28-X-R, and the primer T29-X-R-in (5 pmol each), and templates (1 fmol each) to 0.2-ml PCR tubes, and following the instruction manual of a PCR kit ExTaq (available from Takara Bio, Inc.).

The following four types of templates were used to prepare the PCR mixtures:
(i) Target 1 used as a template;
(ii) Target 1 and Target 2 used as templates;
(iii) Target 2 used as a template; and
(iv) no target (but with water).

After these PCR mixtures were prepared, the tubes were set in a thermal cycler (GeneAmp PCR System, available from Applied Biosystems), and subjected to heat treatment at 95° C. for five minutes and then exposed to 30 cycles of 95° C. for 10 seconds, 55° C. for 30 seconds, and 72° C. for 5 seconds. As to these PCR reaction conditions, the reason why the extension reaction period was set as short as 5 seconds is to only allow selective amplification of short fragments. Under this reaction conditions in the presence of insert-containing Target 2 as a template, a combination of the primer T27-X-F and the primer T28-X-R does not allow the amplification of the 1786-bp fragment, and only the 101-bp amplified fragment is generated with a combination of the primer T27-X-F and the primer T29-X-R-in. Thus, the following respective DNA fragments having the target sequences were amplified: (i) a DNA fragment of 118 bp; (ii) DNA fragments of 118 bp and 101 bp; (iii) a DNA fragment of 101 bp; and (iv) no amplified DNA fragment (negative control).

(4) Preparation of Nucleic Acid Chromatography-Like Test Strip

A test strip to be used for the detection of the PCR products amplified using the spacer-inserted primer sets was prepared in the same manner as in the steps (4) to (6) of Example 13.

(5) Detection of PCR Products Using Test Strip

The PCR products prepared from (i) to (iv) in the step (3) were immediately applied, without being denatured, to the sample application zone on the test strip prepared in the step (4) to perform detection by chromatography.

The results are shown below.
(i): Only the first detection line was colored.
(ii): Both the first and second detection lines were colored.
(iii): Only the second detection line was colored.
(iv): Neither of the detection lines was colored.

The results show that this test strip allowed specific detection of the target plasmids and thus could determine the presence or absence of the insert in the plasmids. The detection by chromatography took a short time (5 to 15 minutes).

Thus, this technique allows determination of the present or absence of genes in plasmids, and by using similar techniques, it is possible to simply detect gene mutations such as insertions or deletions in genomes.

REFERENCE SIGNS LIST

1. Primer region
2. Tag region
3. Polymerase reaction inhibitory region (spacer region)
4. Primer region of first primer (joint primer)
5. Common region of first primer (joint primer)
6. Common region of second primer
7. Tag region of second primer
8. Polymerase reaction inhibitory region (spacer region) of second primer
9. Target nucleic acid sequence
10. Forward primer
11. Primer region of forward primer
12. Tag region of forward primer
13. Reverse primer
14. Primer region of reverse primer
15. Tag region of reverse primer
16. Amplified DNA product having single-stranded region at each end
17. Target nucleic acid sequence
18. First forward primer
19. Primer region of first forward primer
20. Tag region of first forward primer
21. First reverse primer
22. Primer region of first reverse primer
23. Tag region of first reverse primer
24. Double-stranded PCR product amplified using first primers
25. Second forward primer
26. Primer region of second forward primer
27. Tag region of second forward primer
28. Second reverse primer
29. Primer region of second reverse primer
30. Tag region of second reverse primer
31. Amplified DNA product having single-stranded region at each end
32. Sample pad
33. Conjugate pad
34. Carrier carrying capture oligonucleotide
35. Absorption pad
36. Substrate
37. Test line
38. Control line
39. Oligonucleotide to be bonded to labeling molecule
40. Labeling molecule
41. PCR product-labeling molecule complex
42. Porous membrane
43. Capture oligonucleotide
44. Carrier (microarray) with wells carrying capture oligonucleotide
45. Bead carrier carrying capture oligonucleotide
46. Polyacrylamide gel after denaturing PAGE and staining
47. Approximately 360-mer single strand
48. Approximately 330-mer single strand
49. Chromatography-like strip
50. Test line
51. Test line 1
52. Test line 2
53. Test line 3

The invention claimed is:

1. A method for amplifying and detecting comprising (A) amplifying a nucleic acid using primers comprising (i) a 3' nucleic acid hybridizing region that hybridizes to the nucleic acid, (ii) a linker and (iii) a 5' tag region that is linked to the 3' nucleic acid hybridizing region, wherein the amplifying produces an amplicon comprising tag regions that are single-stranded after amplifying and (B) detecting the amplicon comprising steps (1) to (4), wherein the nucleic acid is a double-stranded nucleic acid having a single-stranded region at each end:

(1) dropping a liquid comprising the nucleic acid having a single-stranded region at each end onto an application zone on a chromatographic carrier, (2) diffusing the liquid comprising the nucleic acid having a single-stranded region at each end on the chromatographic carrier with a solvent towards a zone where a first oligonucleotide probe is immobilized, and allowing the nucleic acid having a single-stranded region at each end to hybridize with the first oligonucleotide probe immobilized on a zone different from the application zone on the chromatographic carrier, wherein the diffusing and the allowing the nucleic acid having a single-stranded region at each end to hybridize is performed at room temperature, (3) bonding a second oligonucleotide probe containing a sequence complementary to the other single-stranded region to a labeling substance; and (4) hybridizing the second oligonucleotide probe with the nucleic acid having a single-stranded region at each end.

2. The method for detecting a nucleic acid according to claim 1, further comprising identifying the nucleic acid by visual observation.

3. The method for detecting a nucleic acid according to claim 1, wherein the labeling substance is a colored carrier.

4. The method for detecting a nucleic acid according to claim 1,
wherein in the nucleic acid amplification reaction, a first primer set and a second primer set are used,
wherein the first primer set including primers each containing a sequence capable of hybridizing to the target nucleic acid template and a common sequence incapable of hybridizing to the template, and
the second primer set including primers each containing a sequence capable of hybridizing to a sequence complementary to the common sequence and a tag region that is not made double-stranded by a nucleic acid amplification reaction.

5. The method for amplifying a nucleic acid according to claim 1, wherein the tag region is linked to a corresponding primer via a spacer.

6. The method for amplifying a target nucleic acid according to claim 5, wherein the spacer comprises a nucleic acid derivative.

7. The method for amplifying a nucleic acid according to claim 6, wherein the nucleic acid derivative is at least one member selected from the group consisting of a L-nucleic acid, a 3-deoxy-2-hydroxy-dN, a nucleic acid containing a modified base, a nucleic acid containing a damaged base, a nucleic acid containing a modified phosphate linkage, a RNA, a 2'-OMe-N, and derivatives thereof.

8. The method for amplifying a nucleic acid according to claim 7, wherein the L-nucleic acid is at least one member selected from the group consisting of a L-DNA, a L-RNA, and derivatives thereof.

9. The method for amplifying a nucleic acid according to claim 7, wherein the 3-deoxy-2-hydroxy-dN is linked to the primer via a 2'-5' linkage.

10. The method for amplifying a nucleic acid according to claim 7, wherein the nucleic acid containing a modified base comprises a chromophore or biotin.

11. The method for amplifying a nucleic acid according to claim 10, wherein the chromophore is at least one member selected from the group consisting of pyrene, etheno, pyrrolo, perylene, fluorescein, FITC, Cy3, Cy5, TAMRA, Dabcyl, and derivatives thereof.

12. The method for amplifying a nucleic acid according to claim 7, wherein the nucleic acid containing a damaged base is at least one member selected from the group consisting of abasic nucleotide, a 5-hydroxymethyl-dN, and derivatives thereof.

13. The method for amplifying a nucleic acid according to claim 7, wherein the nucleic acid containing a modified phosphate linkage comprises a phosphorothioate or a derivative thereof.

14. The method for amplifying a nucleic acid according claim 6, wherein the nucleic acid derivative is linked to the primer via a 5'-5' linkage and to the tag region via a 3'-3' linkage.

15. The method for amplifying a target nucleic acid according to claim 5, wherein the spacer comprises a non-nucleic acid derivative.

16. The method for amplifying a nucleic acid according to claim 15, wherein the non-nucleic acid derivative comprises a D-threoninol scaffold.

17. The method for amplifying a nucleic acid according to claim 16, wherein the D-threoninol scaffold incorporates at least one member selected from the group consisting of azobenzene, biotin, EDTA, and a chromophore.

18. The method for amplifying a nucleic acid according to claim 17, wherein the chromophore is at least one member selected from the group consisting of pyrene, etheno, pyrrolo, perylene, fluorescein, FITC, Cy3, Cy5, TAMRA, Dabcyl, and derivatives thereof.

19. The method for amplifying a nucleic acid according to claim 14, wherein the non-nucleic acid derivative is at least one member selected from the group consisting of a carbon chain (Cn), a PEG chain ((CH2CH2O)n), a disulfide-containing chain (CnSSCn), and dithiol phosphoramidite.

20. The method for amplifying a nucleic acid according to claim 5, wherein the spacer comprises multiple spacers.

21. The method for amplifying and detecting according to claim 1, wherein multiple nucleic acids are detected at one time by:

(A) amplifying multiple nucleic acids using multiple sets of primers comprising (i) a 3' nucleic acid hybridizing region that hybridizes to the nucleic acid, (ii) a linker and (iii) a 5' tag region that is linked to the 3' nucleic acid hybridizing region, wherein the amplifying produces multiple amplicons comprising tag regions that are single-stranded after amplifying and (B) detecting the amplicons comprising steps (1) to (4), wherein the nucleic acids are double-stranded nucleic acids having a single-stranded region at each end:

(1) dropping a liquid comprising the nucleic acid having a single-stranded region at each end onto an application zone on a chromatographic carrier, (2) diffusing the liquid comprising the nucleic acid having a single-stranded region at each end on the chromatographic carrier with a solvent towards zones where multiple first oligonucleotide probes are respectively immobilized, and allowing the nucleic acids having a single-stranded region at each end to hybridize with corresponding first oligonucleotide probe immobilized on a zones different from the application zones on the chromatographic carrier, wherein the diffusing and the allowing the nucleic acids having a single-stranded region at each end to hybridize is performed at room temperature, (3) bonding multiple second oligonucleotide probes containing sequences complementary to the other single-stranded region to a labeling substances; and (4) hybridizing the second oligonucleotide probes with the nucleic acids having a single-stranded region at each end.

* * * * *